(12) United States Patent
Balaganesan et al.

(10) Patent No.: US 8,592,055 B2
(45) Date of Patent: *Nov. 26, 2013

(54) COMPOUND FOR ORGANIC ELECTROLUMINESCENT DEVICE AND ORGANIC ELECTROLUMINESCENT DEVICE HAVING THE SAME

(75) Inventors: Banumathy Balaganesan, Taoyuan (TW); Yi-Huan Fu, Taoyuan (TW); Huang-Ming Guo, Taoyuan (TW)

(73) Assignee: E-Ray Optoelectronics Technology Co., Ltd., Chung-Li (TW)

( * ) Notice: Subject to any disclaimer, the term of this patent is extended or adjusted under 35 U.S.C. 154(b) by 136 days.

This patent is subject to a terminal disclaimer.

(21) Appl. No.: 13/161,687

(22) Filed: Jun. 16, 2011

(65) Prior Publication Data
US 2011/0309345 A1    Dec. 22, 2011

Related U.S. Application Data

(60) Provisional application No. 60/355,782, filed on Jun. 17, 2010.

(51) Int. Cl.
*H01L 51/54*    (2006.01)

(52) U.S. Cl.
USPC ........... 428/690; 428/917; 313/504; 313/505; 313/506; 257/40; 257/E51.05; 257/E51.026; 257/E51.032; 548/418; 548/440; 544/234

(58) Field of Classification Search
USPC .................. 428/690, 917; 313/504, 505, 506; 257/40, E51.05, E51.026, E51.032; 548/440, 418; 544/234
See application file for complete search history.

(56) References Cited

U.S. PATENT DOCUMENTS

2011/0168992 A1 *    7/2011    Bae et al. ........................ 257/40

FOREIGN PATENT DOCUMENTS

JP    2009-021336    *    1/2009    ............. H01L 51/50

* cited by examiner

*Primary Examiner* — Gregory Clark
(74) *Attorney, Agent, or Firm* — Turocy & Watson, LLP

(57) ABSTRACT

The present invention provides a compound of formula (I) for an organic electroluminescent device:

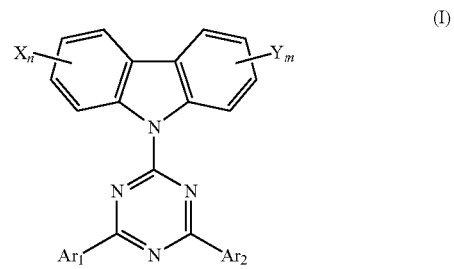

wherein X and Y are each independently selected for the group consisting of an alkyl substituted, aryl substituted or unsubstituted carbazole, indolocarbazole, triphenylsilyl and diphenylphosphine oxide represented by formula (A), (B), (C), (D) or (E).

16 Claims, 13 Drawing Sheets

COMPOUND FOR ORGANIC ELECTROLUMINESCENT DEVICE AND ORGANIC ELECTROLUMINESCENT DEVICE HAVING THE SAME

CROSS-REFERENCE TO RELATED APPLICATION

This application is based upon and claims the benefit of priority from U.S. provisional application 61/355,782 filed on Jun. 17, 2010, the entire contents of which are incorporated herein by reference.

BACKGROUND OF THE INVENTION

1. Field of the Invention

The present invention relates to a compound for organic electroluminescent (EL) devices and an organic electroluminescent device using the same, and more particularly, to a compound for organic electroluminescent devices and an electroluminescent device using the same with a high luminous efficiency, reduced driving voltage, high thermal resistance and long lifetime.

2. Description of Related Art

There has been an increasing interest in developing novel organic materials that cater to organic light emitting device (OLED) applications. Such devices are commercially attractive because they offer the cost-advantageous fabrication of high density pixeled displays exhibiting brilliant luminance with long life times, high efficiency, low driving voltages and wide color range.

A typical OLED comprises at least one organic emissive layer sandwiched between an anode and a cathode. When a current is applied, the anode injects holes and the cathode injects electrons into the organic layer(s). The injected holes and electrons each migrate toward the oppositely charged electrode. When an electron and hole localize on the same molecule, an "exciton" which is a localized electron-hole pair having an excited energy state is formed. Light is emitted when the exciton relaxes through a photoemissive mechanism. To improve the charge transport capabilities and also the luminous efficiency of such devices, additional layers around the emissive layer, such as an electron transport layer and/or a hole transport layer, or an electron blocking and/or hole blocking layer(s) have been incorporated. Doping the host material with another material (guest) has been well demonstrated in literature to enhance the device performance and to tune the chromaticity.

The initial OLEDs used emissive materials that emitted light from their singlet states, termed as "fluorescence". Fluorescent emission generally occurs in a time frame of less than 10 nanoseconds. Several OLED materials and device configurations utilizing fluorescence are described in U.S. Pat. No. 4,769,292, U.S. Pat. No. 5,844,363, and U.S. Pat. No. 5,707,745, which are incorporated herein by reference in their entirety.

More recently, OLEDs having emissive materials that emit light from triplet states (phosphorescence) have been demonstrated in literature, Nature, 1998, No. 395, p. 151 and Appl. Phys. Lett., 1999, No. 3, p. 4, and U.S. Pat. No. 7,279,704, which are incorporated herein by reference in their entirety.

Selection of a host material in phosphorescent OLED's is difficult especially since the non-emissive triplet excited state of the host material must be higher than that of the guest phosphor (dopant). In addition, a host material must have good charge transport properties for an efficient organic EL device.

JP2001-313178 disclosed CBP (4,4'-bis(N-carbazolyl)-1,1'-biphenyl) as the host material, which is characterized by having a good hole transport property but poor electron transporting. Hence the use of CBP as a host material for tris(2-phenylpyridine) iridium (hereinafter referred to as Ir(ppy)$_3$), a green phosphorescent emitter, disturbs balanced injection of electrical charges, causing excess holes to flow towards the electron transporting layer, thereby decreasing the luminous efficiency. Moreover, due to its low molecular weight, it tends to crystallize and thus is not suitable for OLED devices.

One of the means to solve the above problem is to introduce a hole blocking layer between the light emitting layer and the electron transporting layer as described in JP2002-305083. This hole blocking layer accumulates holes efficiently in the light emitting layer and contributes to increase the probability of recombination of holes and electrons and thus enhances the luminous efficiency. Currently, the hole-blocking materials in general use include 2,9-dimethyl-4,7-diphenyl-1,10-phenanthroline (hereinafter referred to as BCP) and phenylphenolato-bis(2-methyl-8-quinolinator-N1,O8)aluminum (hereinafter referred to as BAlq). However, BCP tends to crystallize even at room temperature and lacks reliability as a hole blocking material and the life of the device is extremely short; whereas BAlq has insufficient hole blocking ability.

For a high luminous and efficient OLED's, a host material must have non-emissive high triplet energy and a balanced electrical charge (hole/electron) injection/transport characteristics. Moreover, the host material should also possess good electrochemical stability, high thermal resistance and excellent thin film stability. However, compound capable of satisfying all the said properties from practical considerations have not been known till date.

Attempts have been made to introduce molecular moiety that has an excellent hole transport property as represented by a carbazole or triarylamine and another moiety that has an excellent electron transport property as represented by pyrimidine or triazine into one and the same molecular skeleton, as phosphorescent host materials, as disclosed in the patent documents WO2003-78451, WO2005-76668, US2006-51616, JP2008-280330, WO2008-123189 and JP 2009-21336.

When a plurality of skeletons differing from one another in the electrical charge transport properties are introduced into one and the same molecule, the molecule may undergo large changes in the balance of electrical charges, leading to higher driving voltages, reduced lifetime and low efficiency.

Hence, there is a need to develop a material for an organic electroluminescent device for producing an organic electroluminescent device with a high luminous efficiency, reduced driving voltage, high thermal resistance and long lifetime.

SUMMARY OF THE INVENTION

It is an aspect of the present invention to provide a compound of formula (I) for an organic electroluminescent device:

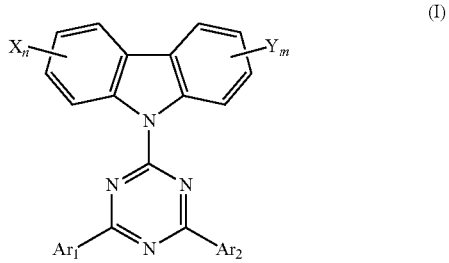

wherein X and Y are each independently selected for the group consisting of an alkyl substituted, aryl substituted or unsubstituted carbazole, indolocarbazole, triphenylsilyl and diphenylphosphine oxide represented by formula (A), (B), (C), (D) or (E),

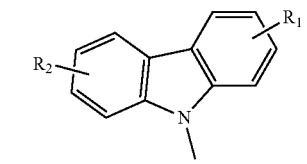

(A)

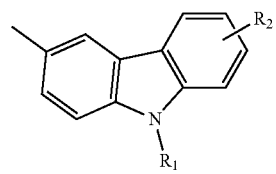

(B)

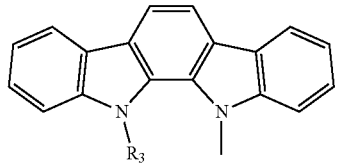

(C)

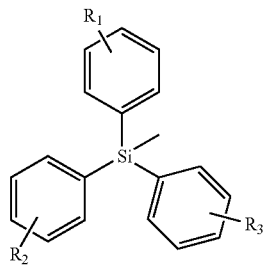

(D)

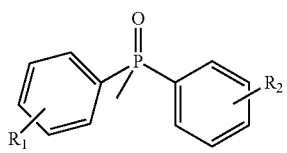

(E)

in which $R_1$, $R_2$, and $R_3$ are each independently selected from the group consisting of a hydrogen, an alkyl having carbons from 1 to 15, an aryl group having carbons from 6 to 15, an alkyl substituted, an aryl substituted or unsubstituted triphenylsilyl, and a diphenylphosphine oxide represented by the formula (D) or (E); m and n are each independently 0 or 1, provided that m+n is 1 or more; and $Ar_1$ and $Ar_2$ are each independently selected from the group consisting of an alkyl substituted, aryl substituted or unsubstituted phenyl, tolyl, naphthyl, fluorenyl, anthracenyl, and phenanthryl.

Preferably, the compound of formula (I) may be one of compounds represented by formulae (II) to (XIII):

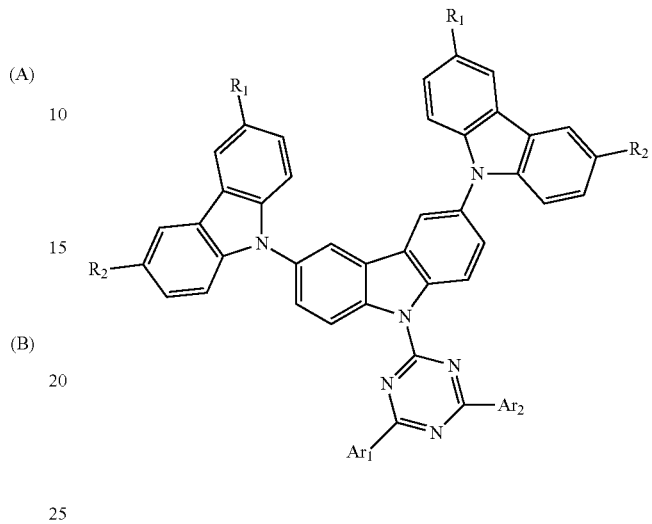

(II)

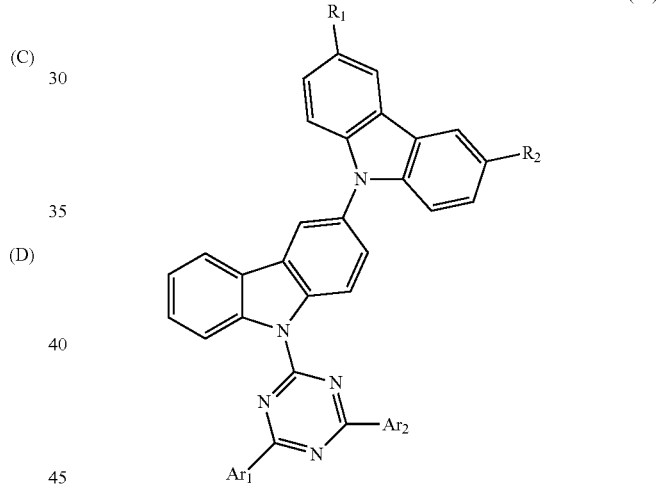

(III)

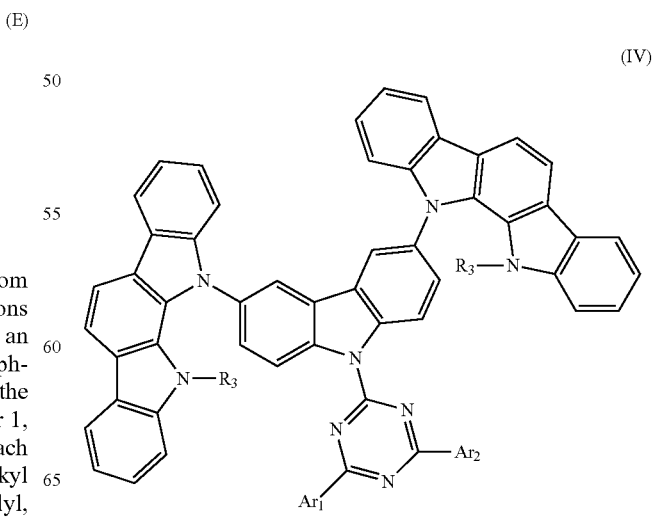

(IV)

-continued
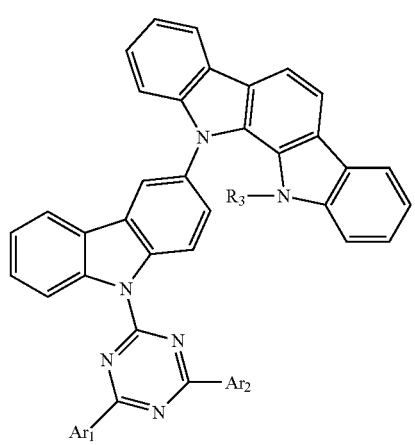
(V)
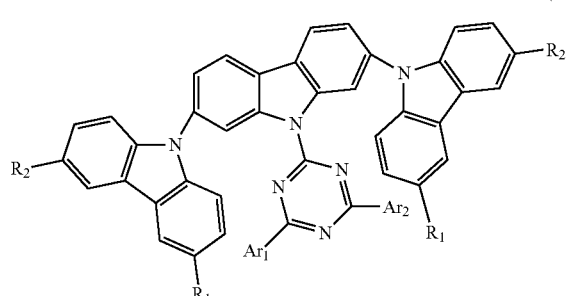
(VI)
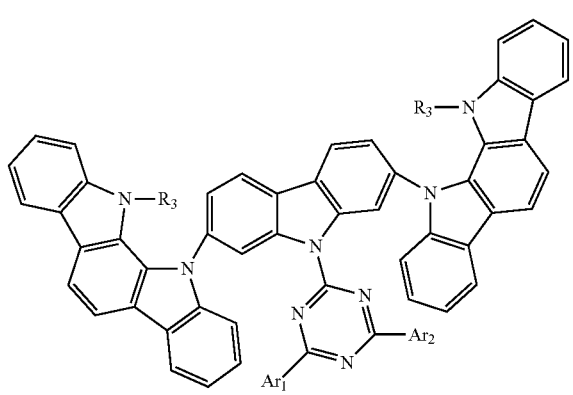
(VII)
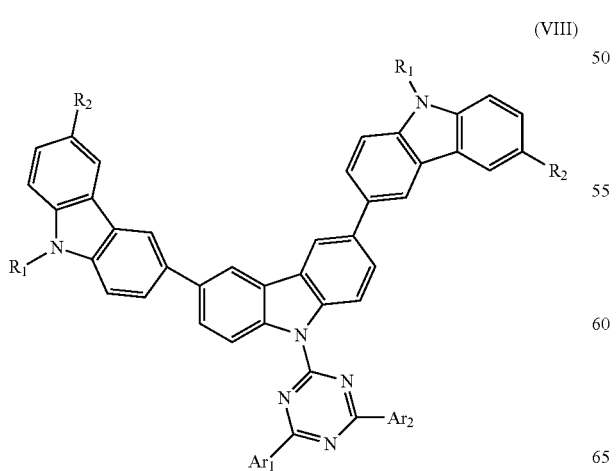
(VIII)
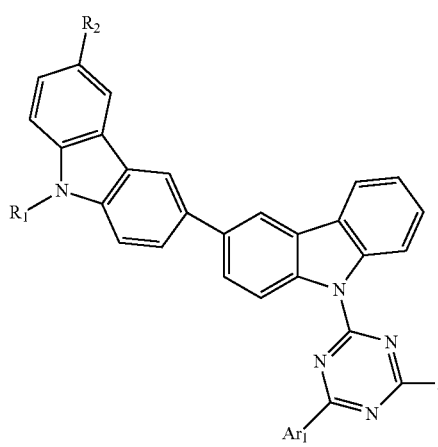
(IX)
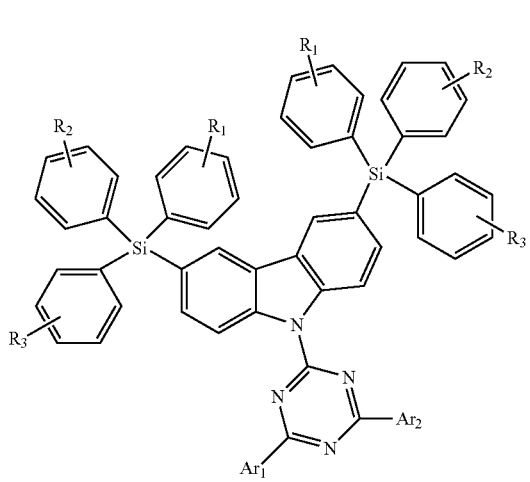
(X)
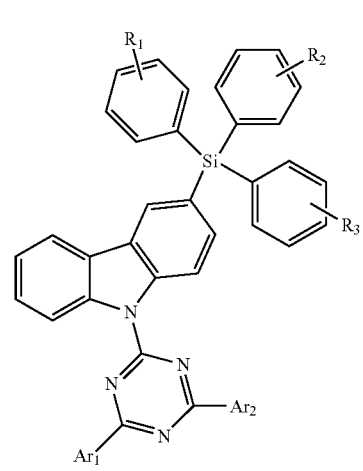
(XI)

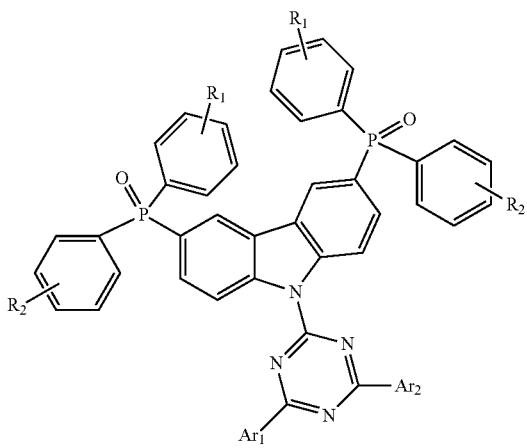

(XII)

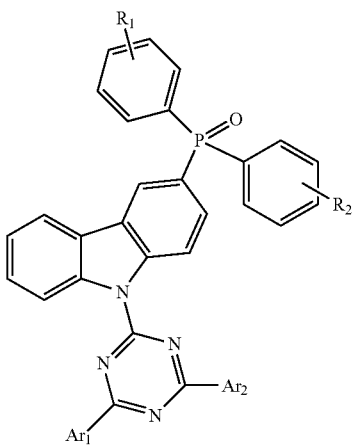

(XIII)

wherein $R_1$, $R_2$, and $R_3$ are each independently selected from the group consisting of a hydrogen, a substituted or unsubstituted alkyl group having 1 to 10 carbon atoms, a substituted or unsubstituted cycloalkyl group having 5 to 10 carbon atoms, a substituted or unsubstituted aralkyl group having 7 to 15 carbon atoms, a substituted or unsubstituted aromatic hydrocarbon group having 6 to 15 carbon atoms, an alkyl substituted, an aryl substituted or unsubstituted triphenylsilyl, and a diphenylphosphine oxide represented by the formula (D) or (E); m and n each independently represent 0 or 1, provided that m+n is 1 or more; and $Ar_1$ and $Ar_2$ are each independently selected from the group consisting of an alkyl substituted, aryl substituted or unsubstituted phenyl, tolyl, naphthyl, fluorenyl, anthracenyl, and phenanthryl.

It is another aspect of the present invention to provide a light emitting layer for an organic electroluminescent device, including a phosphorescent dopant; and a compound of formula selected from formulae (II) to (XIII), wherein $R_1$, $R_2$, $R_3$ are each independently selected from the group consisting of a hydrogen, a substituted or unsubstituted alkyl group having 1 to 10 carbon atoms, a substituted or unsubstituted cycloalkyl group having 5 to 10 carbon atoms forming the ring, a substituted or unsubstituted aralkyl group having 7 to 15 carbon atoms, a substituted or unsubstituted aromatic hydrocarbon group having 6 to 15 carbon atoms, an alkyl substituted, an aryl substituted or unsubstituted triphenylsilyl, and a diphenylphosphine oxide represented by the formula (D) or (E); in and n each independently represent 0 or 1, provided that m+n is 1 or more; and $Ar_1$ and $Ar_2$ are each independently selected from the group consisting of an alkyl substituted, aryl substituted or unsubstituted phenyl, tolyl, naphthyl, fluorenyl, anthracenyl, and phenanthryl. Further, the phosphorescent dopant is an organic metal complex comprising at least one metal selected from the group consisting of ruthenium, rhodium, palladium, silver, rhenium, osmium, iridium, platinum and gold. Preferably, the phosphorescent dopant is one of $Ir(ppy)_3$, $Ir(bt)_2(acac)$, FIrpic, and $PtOEt_3$. In accordance with the present invention, the phosphorescent dopant is in a range from 3 wt % to 10 wt % of the light emitting layer.

It is another aspect of the present invention to provide an organic electroluminescent device, including a light emitting layer having a compound of a formula selected from formulae (II) to (XIII) and a phosphorescent dopant.

It is another aspect of the present invention to provide an organic electroluminescent device, including an electron transport layer; a hole block layer; and an electron block layer, wherein one of the electron transport layer, the hole block layer and the electron block layer comprises a compound of a formula selected from formulae (II) to (XIII).

It is another aspect of the present invention to provide a method for forming an organic electroluminescent device, including the steps of: providing a substrate; forming a hole injection layer on the substrate; forming a hole transport layer on the hole injecting layer; and forming a light emitting layer on the hole transport layer having a phosphorescent dopant and a compound of a formula selected from formulae (II) to (XIII).

DETAILED DESCRIPTION OF THE PREFERRED EMBODIMENTS

Figure 1:
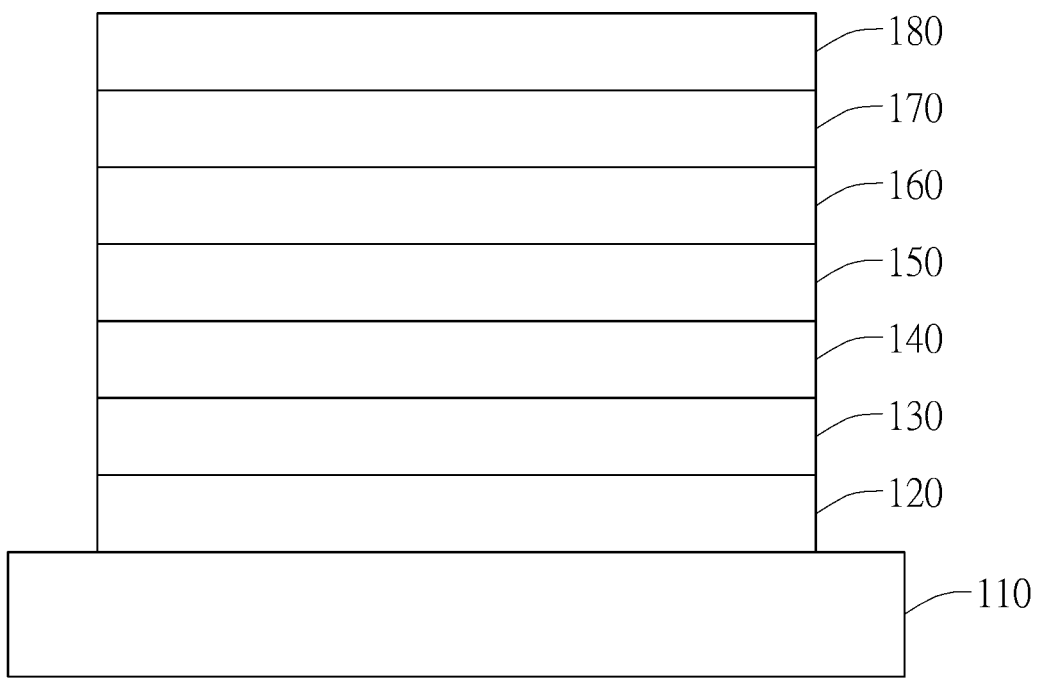
FIG. 1 is a cross-sectional view illustrating an organic light emitting device according to an embodiment of the present invention.

The detailed description of the present invention is illustrated by the following specific examples. Persons skilled in the art can conceive the other advantages and effects of the present invention based on the disclosure contained in the specification of the present invention.

A compound for an organic electroluminescent device according to this invention is represented by formula (I). Preferably, the compound of formula (I) is one of compounds represented by formulae (II) to (XIII).

In formulae (I) to (XIII), $R_1$, $R_2$ and $R_3$ each independently represent a hydrogen, a substituted or unsubstituted alkyl group having 1 to 10 carbon atoms, a substituted or unsubstituted cycloalkyl group having 5 to 10 carbon atoms forming the ring, a substituted or unsubstituted aralkyl group having 7 to 15 carbon atoms, a substituted or unsubstituted aromatic hydrocarbon group having 6 to 15 carbon atoms, an alkyl substituted, an aryl substituted or unsubstituted triphenylsilyl, or a diphenylphosphine oxide group, represented by the formula (D) or (E).

In all of the formulae (I) to (XIII), $Ar_1$ and $Ar_2$ each independently represent an alkyl substituted, aryl substituted or unsubstituted aromatic hydrocarbon group, preferably selected from phenyl, tolyl, naphthyl, fluorenyl, anthracenyl, and phenanthryl groups.

Preferable examples of the compounds represented by the aforementioned general formulae (I) to (XIII) are shown, but not limited to, below.

General formula (II) corresponds to general formula (I) wherein X and Y each independently represent a carbazolyl group represented by formula (A), and may be linked at C-3 and C-6 of the carbazole unit in the basic molecular skeleton of formula (I) of the present invention. Compounds 1-1 to 1-52 shown in Table 1 are examples of formula (II), wherein m=1, n=1 and m+n=2.

TABLE 1

Compound 1-1

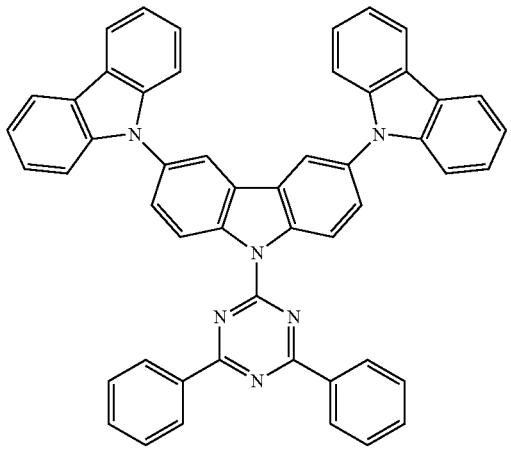 [SMILES: c1ccc(-c2nc(-c3ccccc3)nc(-n3c4ccc(-n5c6ccccc6c6ccccc65)cc4c4cc(-n5c6ccccc6c6ccccc65)ccc43)n2)cc1]

Compound 1-2

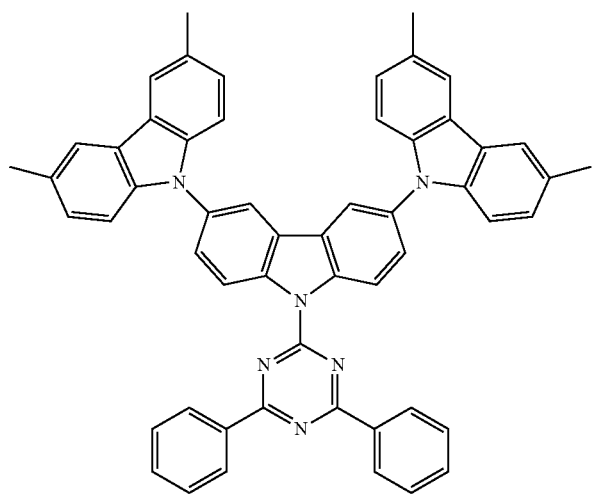

TABLE 1-continued
Compound 1-3
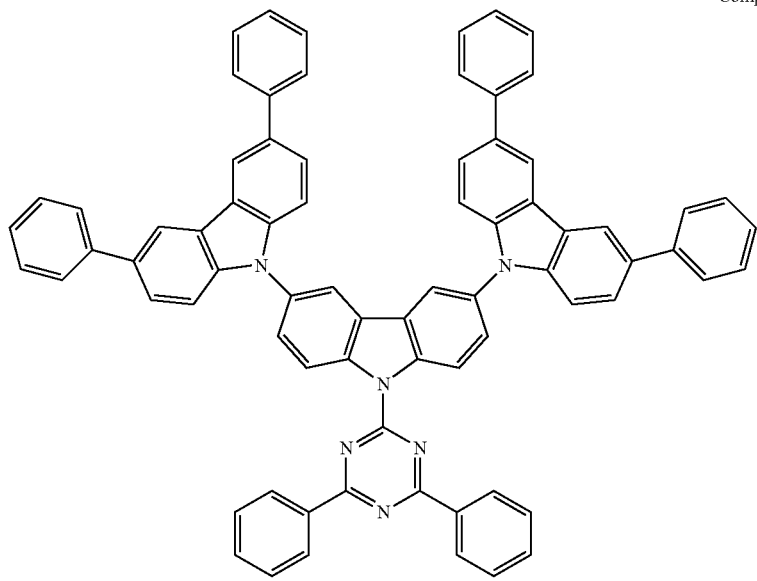
Compound 1-4
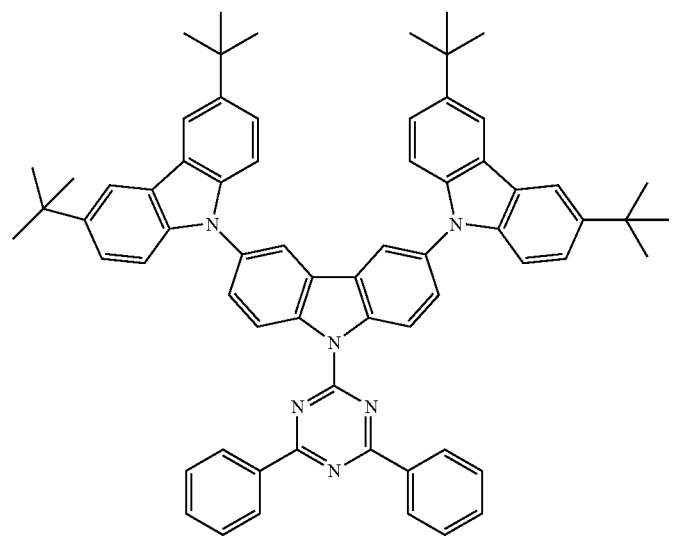 [SMILES: CC(C)(C)c1ccc2c(c1)c1cc(C(C)(C)C)ccc1n2-c1ccc2c(c1)c1cc(-n3c4ccc(C(C)(C)C)cc4c4cc(C(C)(C)C)ccc43)ccc1n2-c1nc(-c2ccccc2)nc(-c2ccccc2)n1]
Compound 1-5
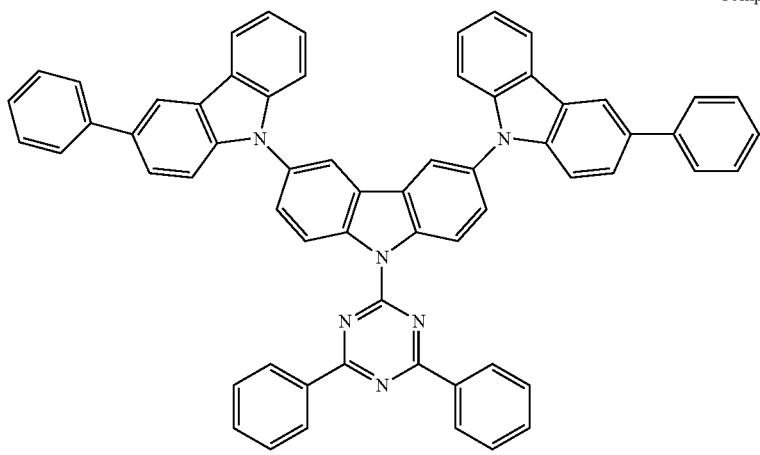

TABLE 1-continued
Compound 1-6
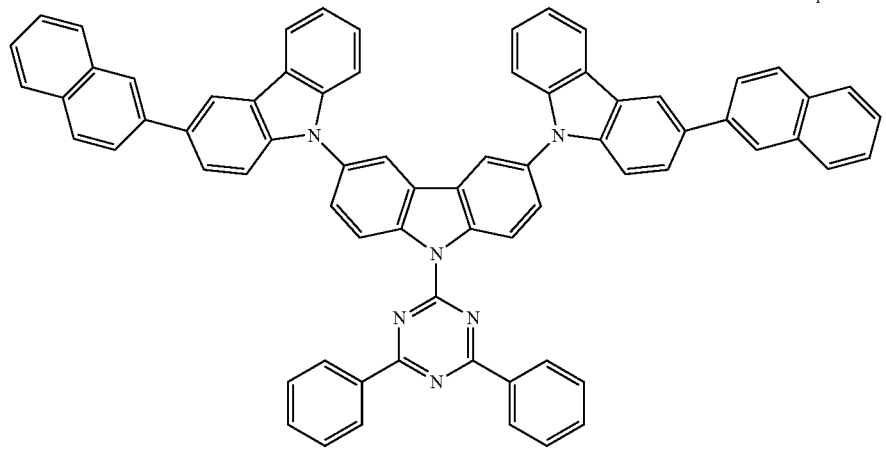
Compound 1-7
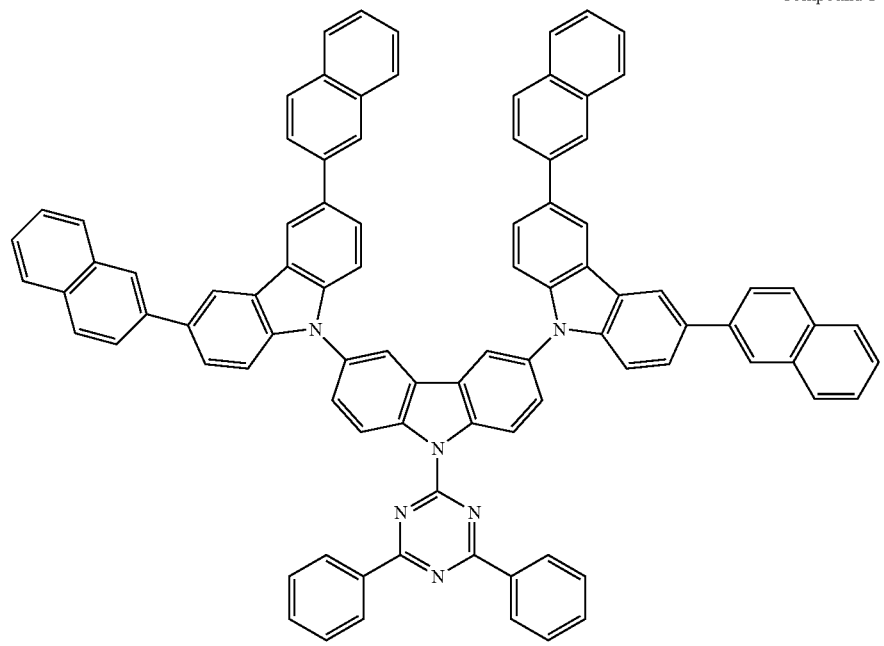

TABLE 1-continued
Compound 1-8
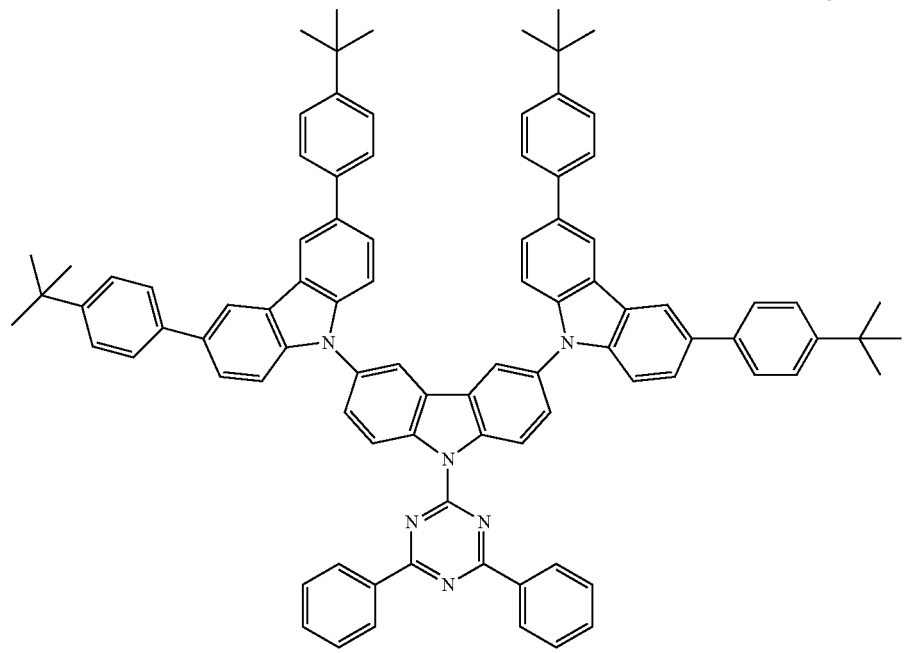 [SMILES: CC(C)(C)c1ccc(-c2ccc3c(c2)c2cc(-c4ccc(C(C)(C)C)cc4)ccc2n3-c2ccc3c(c2)c2cc(-n4c5ccc(-c6ccc(C(C)(C)C)cc6)cc5c5cc(-c6ccc(C(C)(C)C)cc6)ccc54)ccc2n3-c2nc(-c3ccccc3)nc(-c3ccccc3)n2)cc1]
Compound 1-9
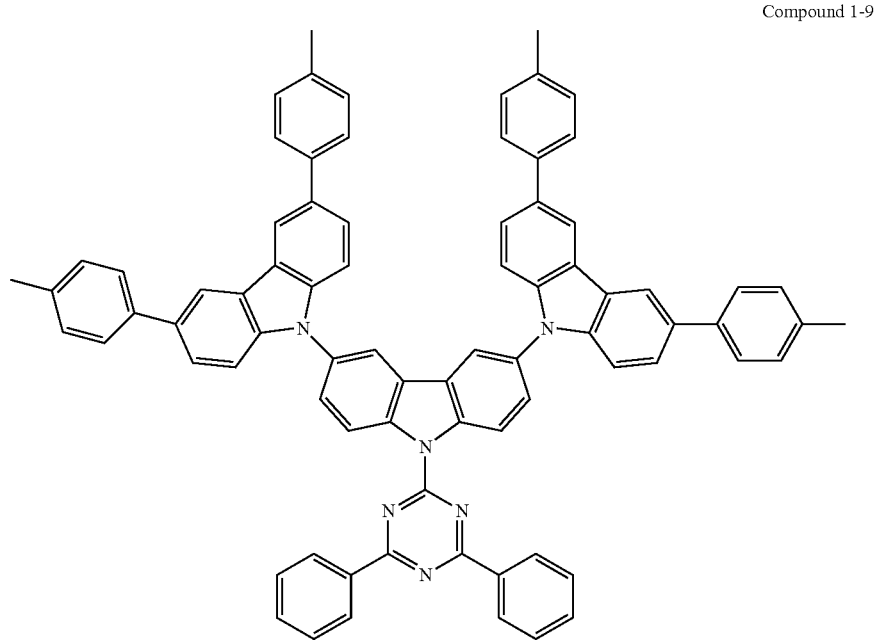

TABLE 1-continued
Compound 1-10
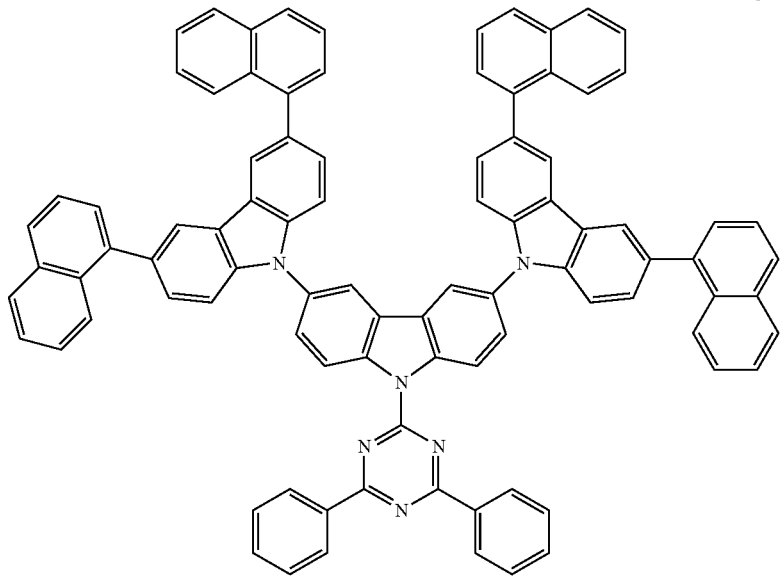 [SMILES: c1ccc(-c2nc(-c3ccccc3)nc(-n3c4ccc(-n5c6ccc(-c7cccc8ccccc78)cc6c6cc(-c7cccc8ccccc78)ccc65)cc4c4cc(-n5c6ccc(-c7cccc8ccccc78)cc6c6cc(-c7cccc8ccccc78)ccc65)ccc43)n2)cc1]
Compound 1-11
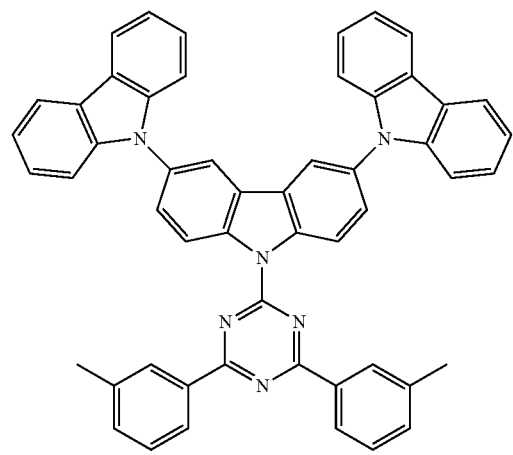 [SMILES: Cc1cccc(-c2nc(-c3cccc(C)c3)nc(-n3c4ccc(-n5c6ccccc6c6ccccc65)cc4c4cc(-n5c6ccccc6c6ccccc65)ccc43)n2)c1]
Compound 1-12
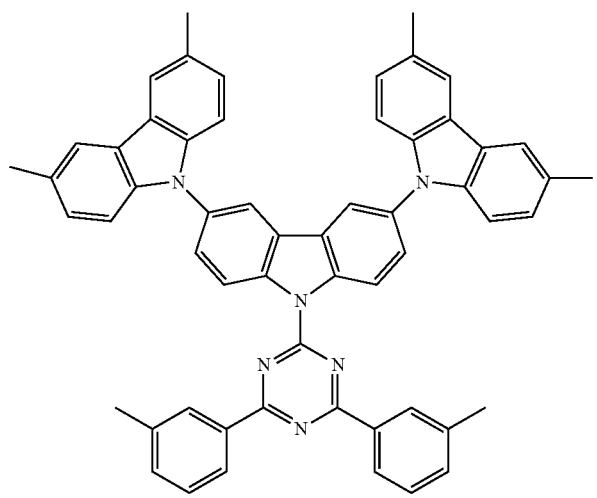

TABLE 1-continued
Compound 1-13
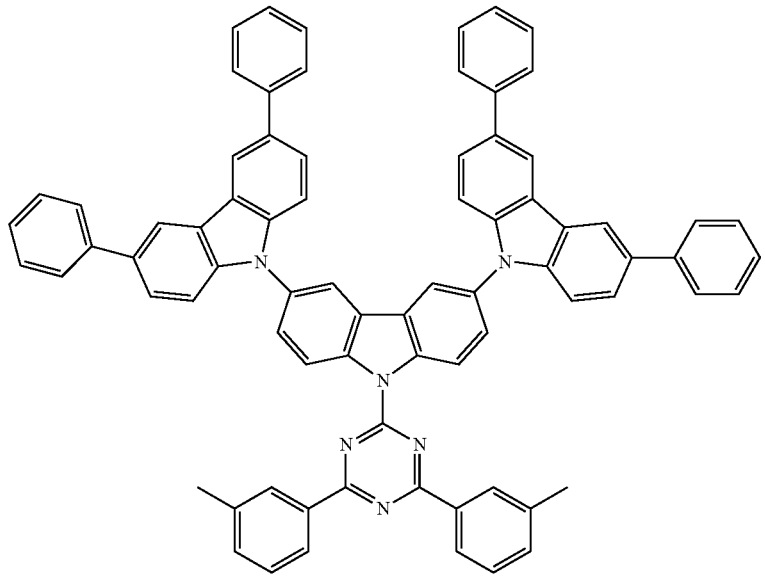 [SMILES: Cc1cccc(-c2nc(-c3cccc(C)c3)nc(-n3c4ccc(-n5c6ccc(-c7ccccc7)cc6c6cc(-c7ccccc7)ccc65)cc4c4cc(-n5c6ccc(-c7ccccc7)cc6c6cc(-c7ccccc7)ccc65)ccc43)n2)c1]
Compound 1-14
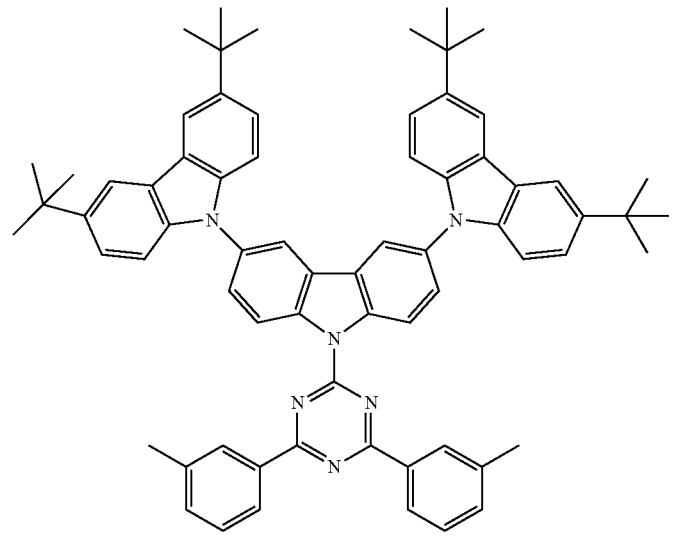 [SMILES: Cc1cccc(-c2nc(-c3cccc(C)c3)nc(-n3c4ccc(-n5c6ccc(C(C)(C)C)cc6c6cc(C(C)(C)C)ccc65)cc4c4cc(-n5c6ccc(C(C)(C)C)cc6c6cc(C(C)(C)C)ccc65)ccc43)n2)c1]

TABLE 1-continued
Compound 1-15
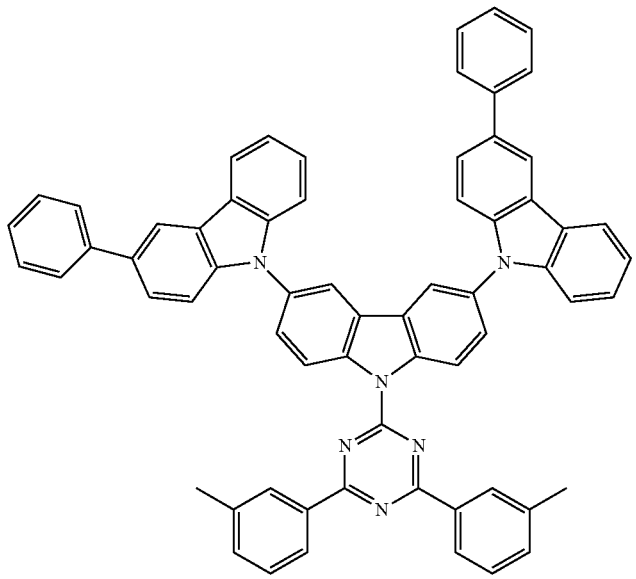 [SMILES: Cc1cccc(-c2nc(-c3cccc(C)c3)nc(-n3c4ccc(-n5c6ccccc6c6cc(-c7ccccc7)ccc65)cc4c4cc(-n5c6ccccc6c6cc(-c7ccccc7)ccc65)ccc43)n2)c1]
Compound 1-16
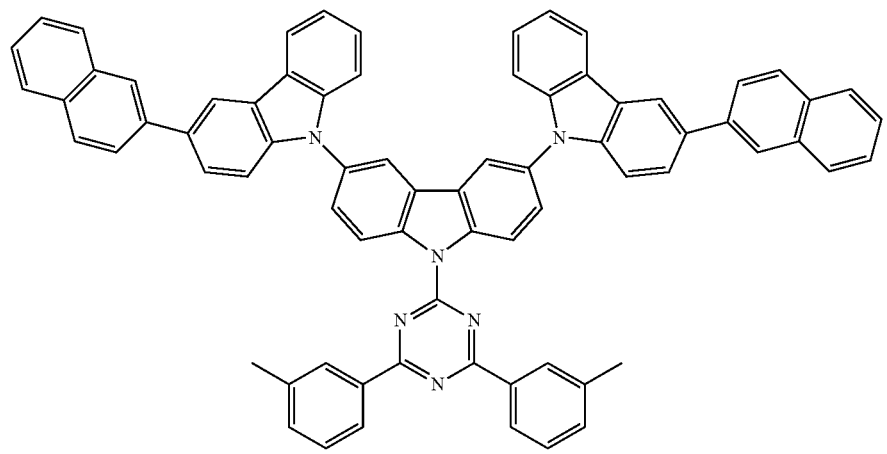 [SMILES: Cc1cccc(-c2nc(-c3cccc(C)c3)nc(-n3c4ccc(-n5c6ccccc6c6cc(-c7ccc8ccccc8c7)ccc65)cc4c4cc(-n5c6ccccc6c6cc(-c7ccc8ccccc8c7)ccc65)ccc43)n2)c1]

TABLE 1-continued
Compound 1-17
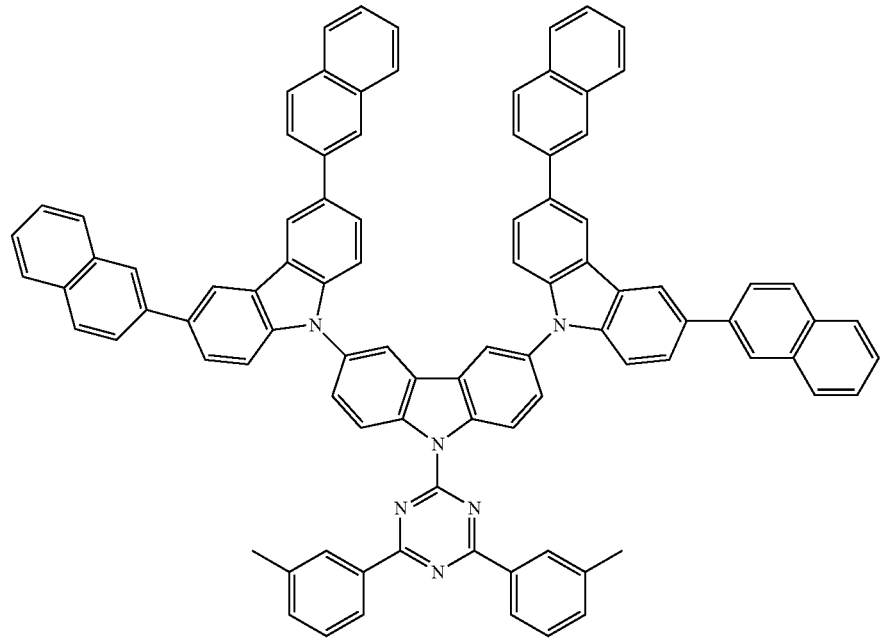 [SMILES: Cc1cccc(-c2nc(-c3cccc(C)c3)nc(-n3c4ccc(-n5c6ccc(-c7ccc8ccccc8c7)cc6c6cc(-c7ccc8ccccc8c7)ccc65)cc4c4cc(-n5c6ccc(-c7ccc8ccccc8c7)cc6c6cc(-c7ccc8ccccc8c7)ccc65)ccc43)n2)c1]
Compound 1-18
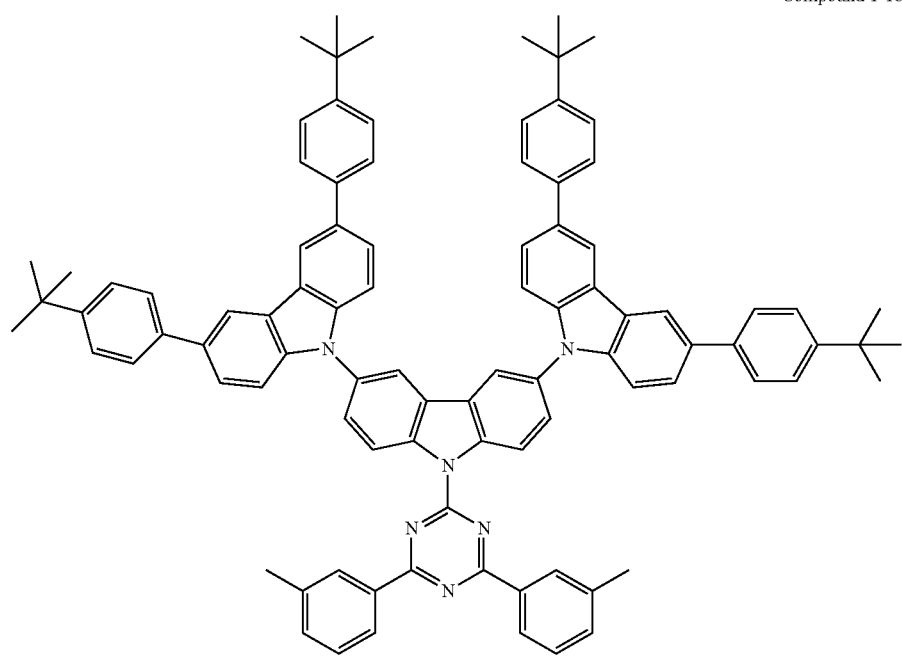

TABLE 1-continued
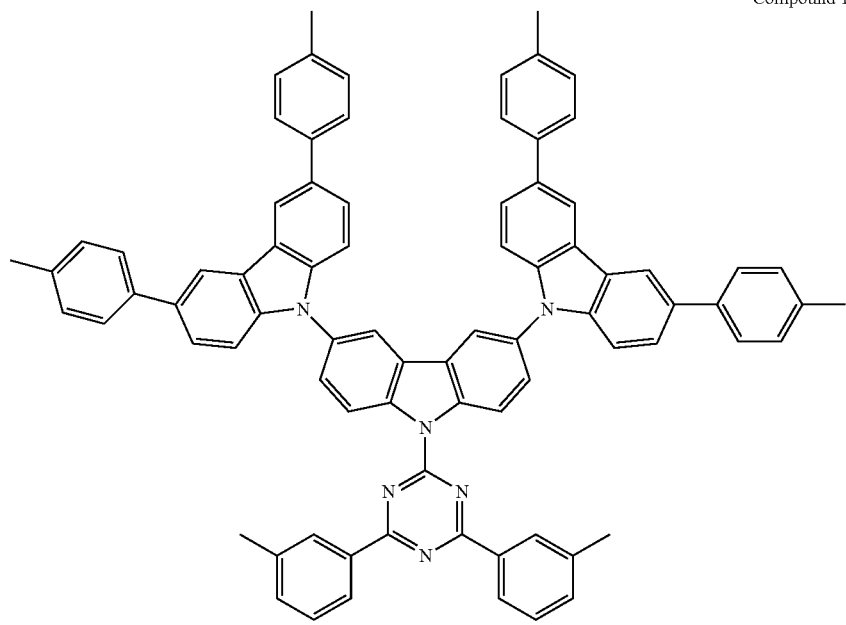
Compound 1-19
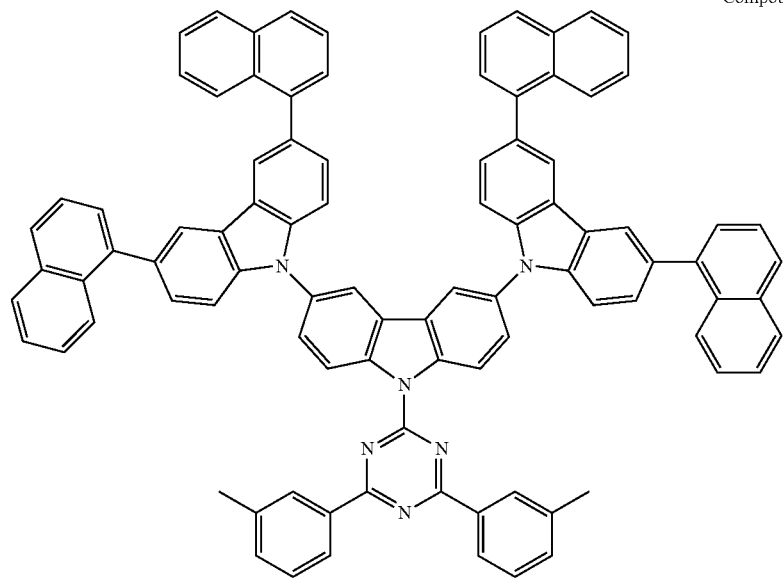
Compound 1-20

TABLE 1-continued
Compound 1-21
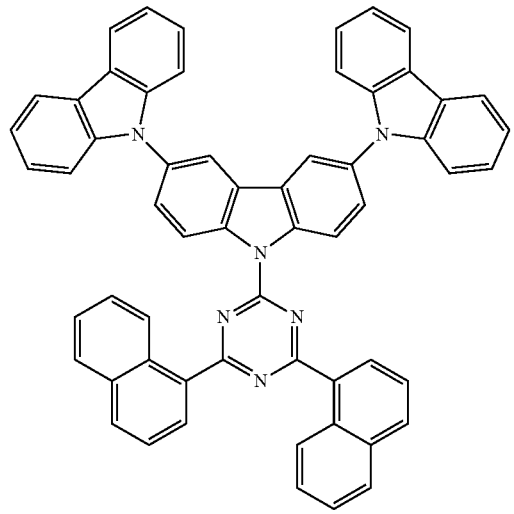 [SMILES: c1ccc2c(-c3nc(-c4cccc5ccccc45)nc(-n4c5ccc(-n6c7ccccc7c7ccccc76)cc5c5cc(-n6c7ccccc7c7ccccc76)ccc54)n3)cccc2c1]
Compound 1-22
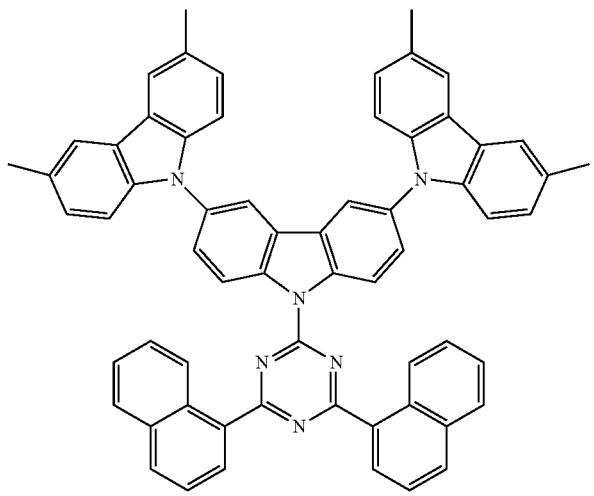
Compound 1-23
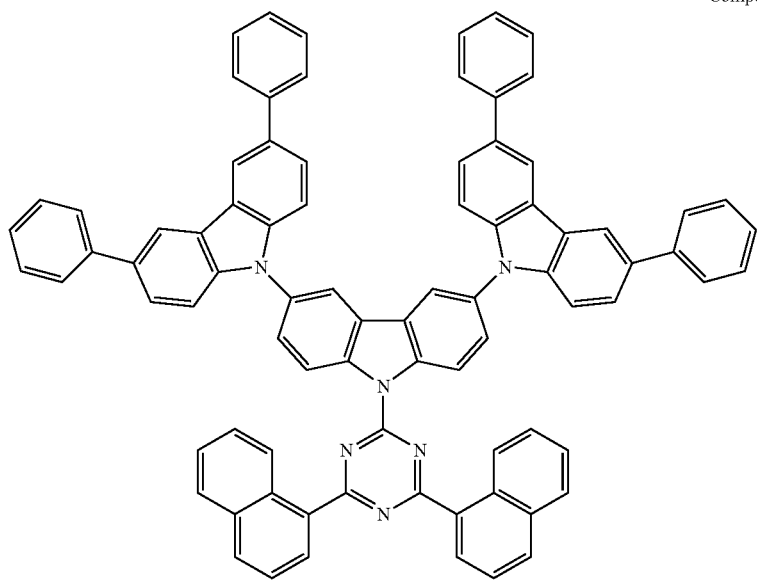

TABLE 1-continued
Compound 1-24
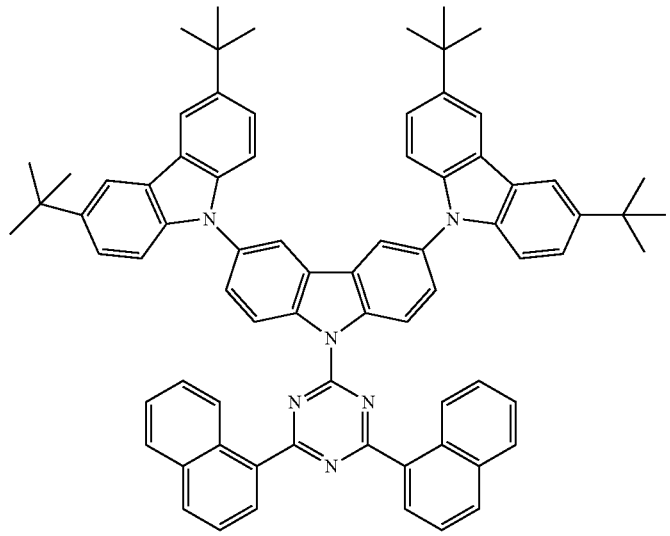 [SMILES: CC(C)(C)c1ccc2c(c1)c1cc(C(C)(C)C)ccc1n2-c1ccc2c(c1)c1cc(-n3c4ccc(C(C)(C)C)cc4c4cc(C(C)(C)C)ccc43)ccc1n2-c1nc(-c2cccc3ccccc23)nc(-c2cccc3ccccc23)n1]
Compound 1-25
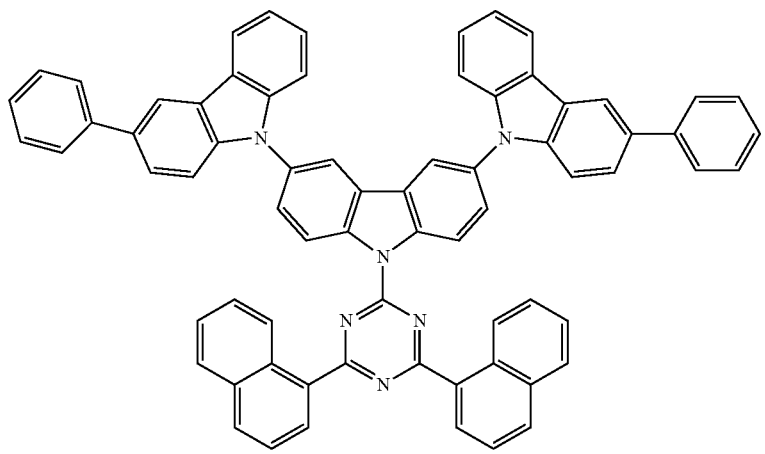 [SMILES: c1ccc(-c2ccc3c(c2)c2ccccc2n3-c2ccc3c(c2)c2cc(-n4c5ccccc5c5cc(-c6ccccc6)ccc54)ccc2n3-c2nc(-c3cccc4ccccc34)nc(-c3cccc4ccccc34)n2)cc1]
Compound 1-26
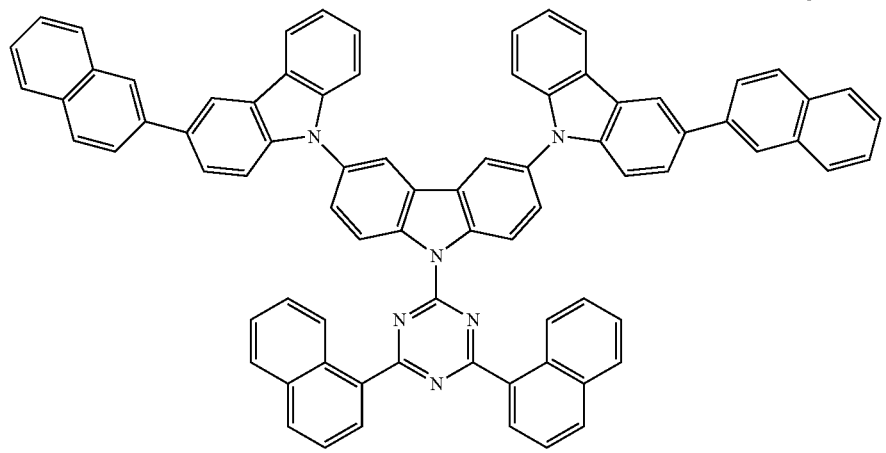 [SMILES: c1ccc2cc(-c3ccc4c(c3)c3ccccc3n4-c3ccc4c(c3)c3cc(-n5c6ccccc6c6cc(-c7ccc8ccccc8c7)ccc65)ccc3n4-c3nc(-c4cccc5ccccc45)nc(-c4cccc5ccccc45)n3)ccc2c1]

TABLE 1-continued
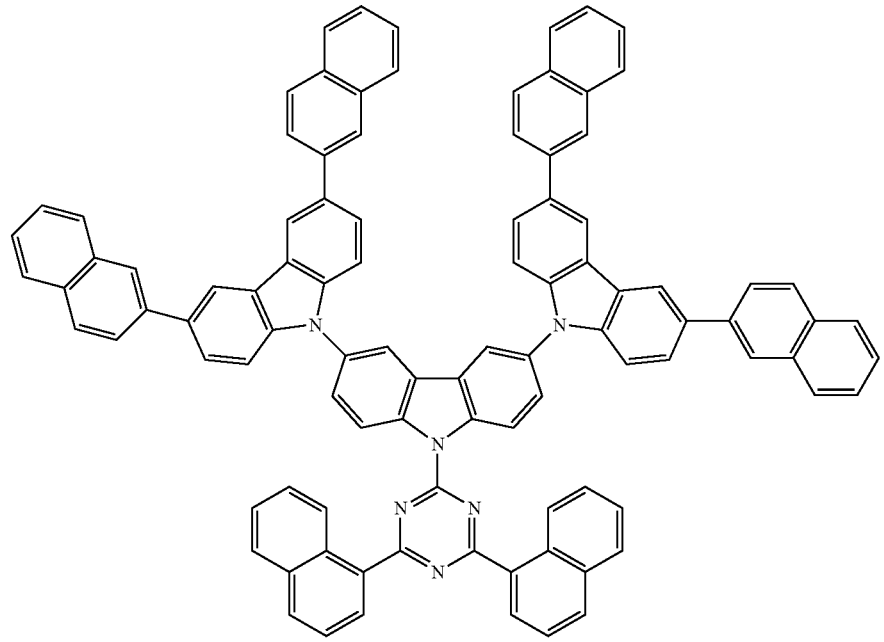 [SMILES: c1ccc2cc(-c3ccc4c(c3)c3cc(-c5ccc6ccccc6c5)ccc3n4-c3ccc4c(c3)c3cc(-n5c6ccc(-c7ccc8ccccc8c7)cc6c6cc(-c7ccc8ccccc8c7)ccc65)ccc3n4-c3nc(-c4cccc5ccccc45)nc(-c4cccc5ccccc45)n3)ccc2c1]
Compound 1-27
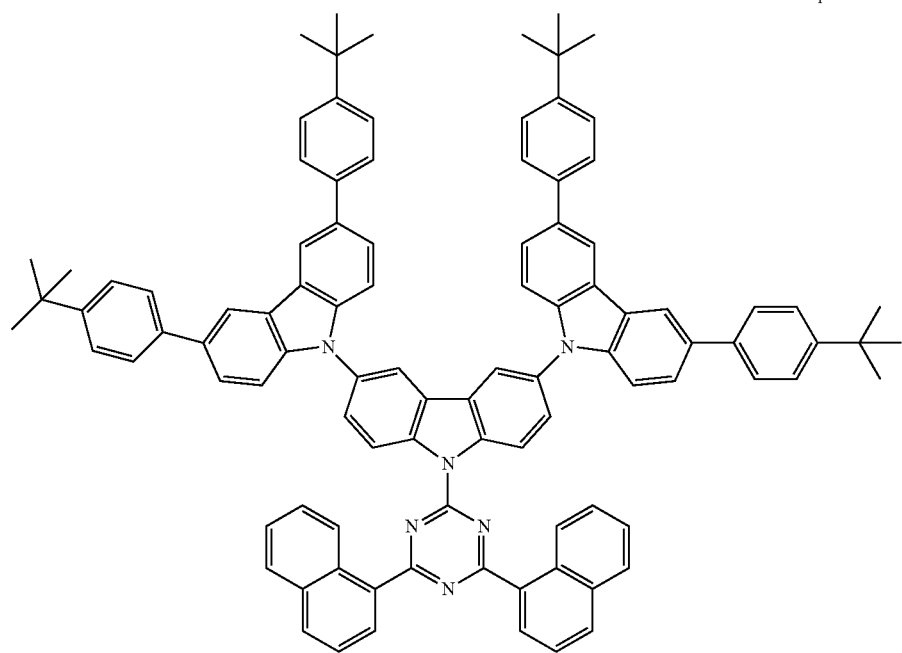
Compound 1-28

TABLE 1-continued
Compound 1-29
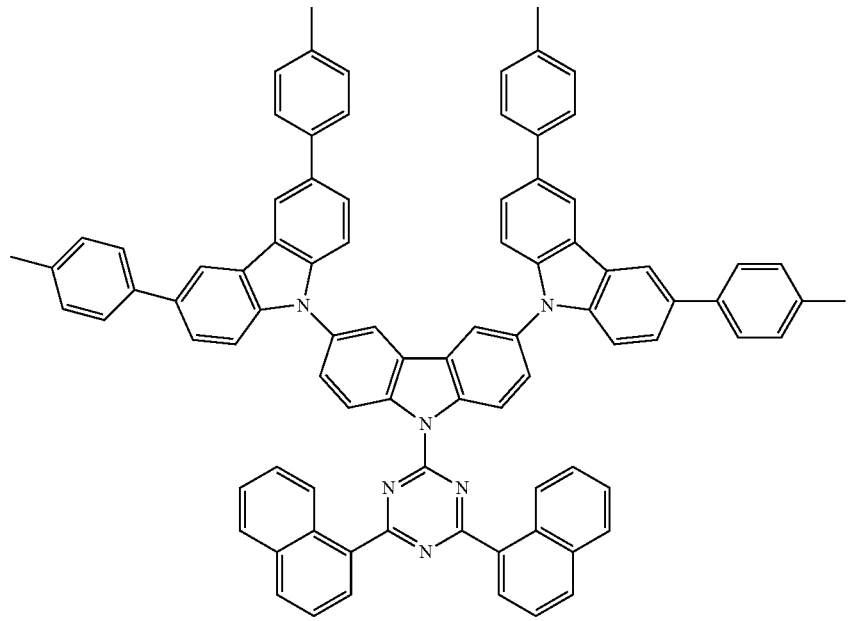
Compound 1-30
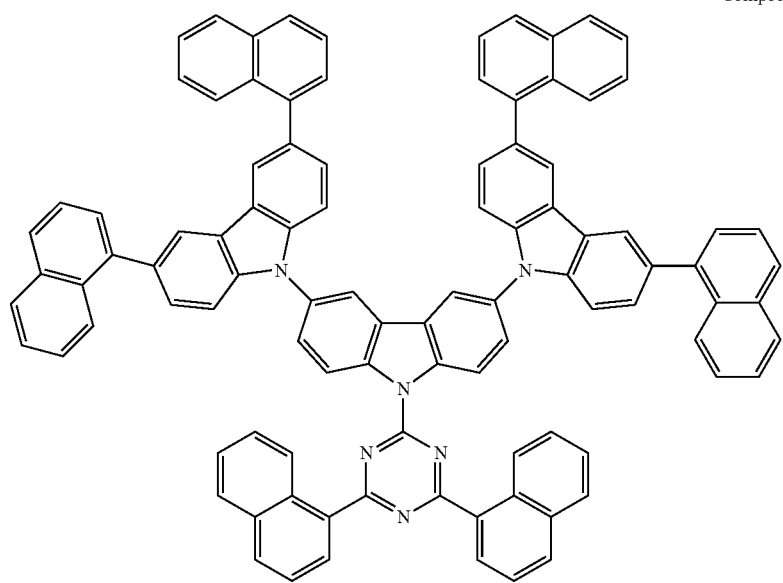

TABLE 1-continued
Compound 1-31
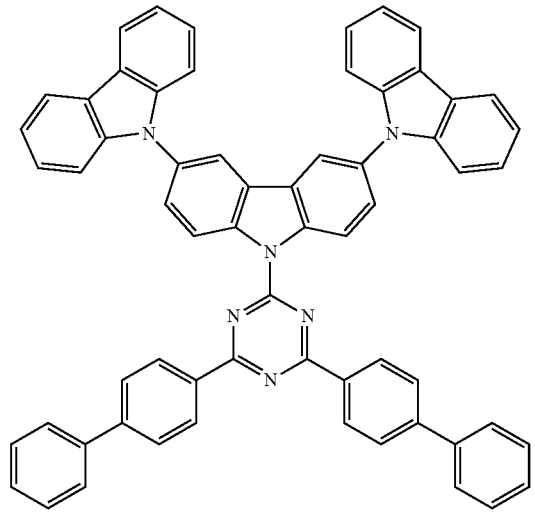 [SMILES: c1ccc(-c2ccc(-c3nc(-c4ccc(-c5ccccc5)cc4)nc(-n4c5ccc(-n6c7ccccc7c7ccccc76)cc5c5cc(-n6c7ccccc7c7ccccc76)ccc54)n3)cc2)cc1]
Compound 1-32
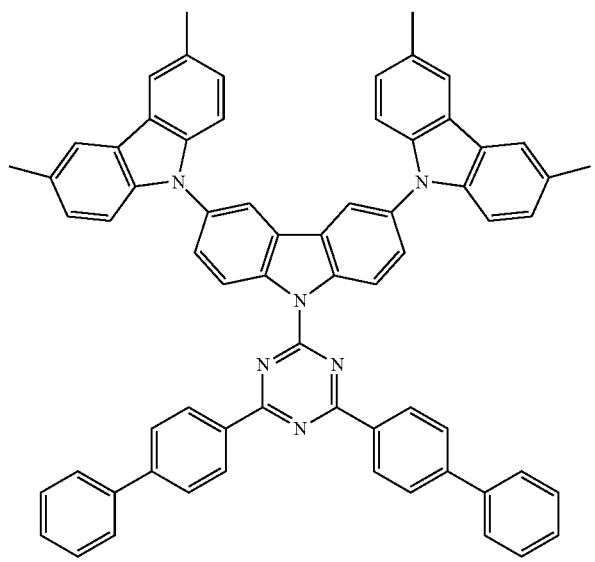

TABLE 1-continued
Compound 1-33
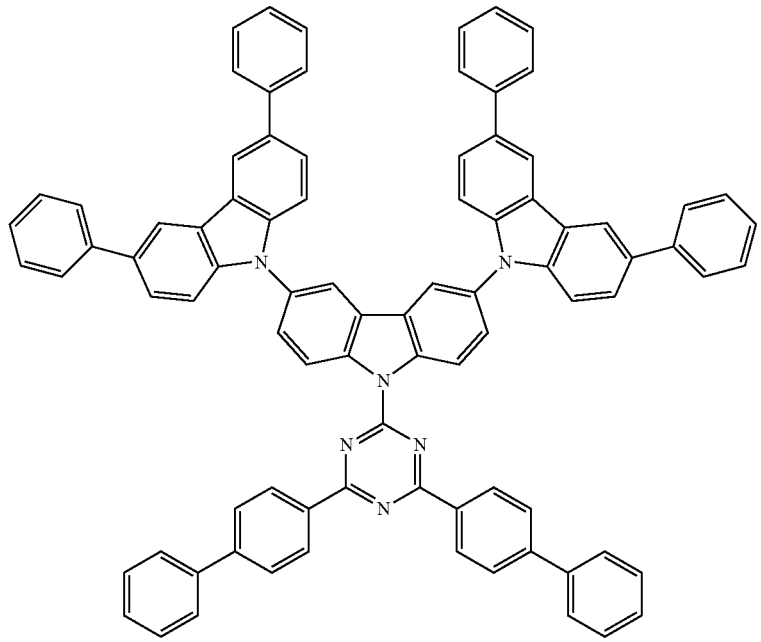 [SMILES: c1ccc(-c2ccc(-c3nc(-c4ccc(-c5ccccc5)cc4)nc(-n4c5ccc(-n6c7ccc(-c8ccccc8)cc7c7cc(-c8ccccc8)ccc76)cc5c5cc(-n6c7ccc(-c8ccccc8)cc7c7cc(-c8ccccc8)ccc76)ccc54)n3)cc2)cc1]
Compound 1-34
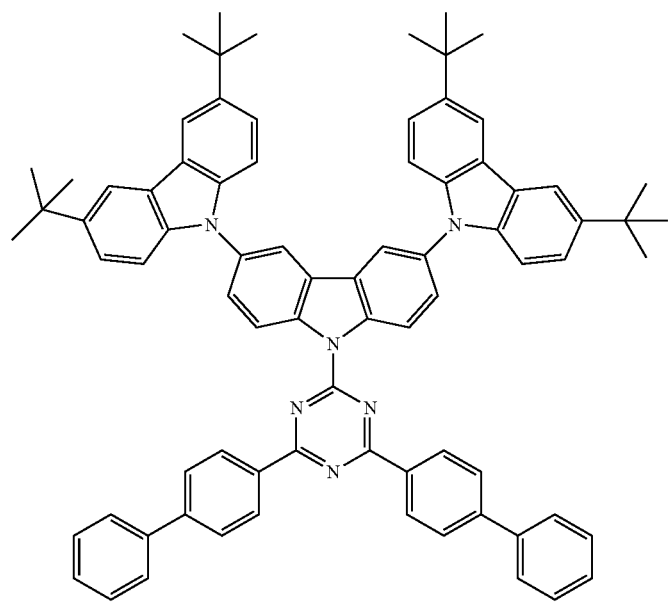 [SMILES: CC(C)(C)c1ccc2c(c1)c1cc(C(C)(C)C)ccc1n2-c1ccc2c(c1)c1cc(-n3c4ccc(C(C)(C)C)cc4c4cc(C(C)(C)C)ccc43)ccc1n2-c1nc(-c2ccc(-c3ccccc3)cc2)nc(-c2ccc(-c3ccccc3)cc2)n1]

TABLE 1-continued
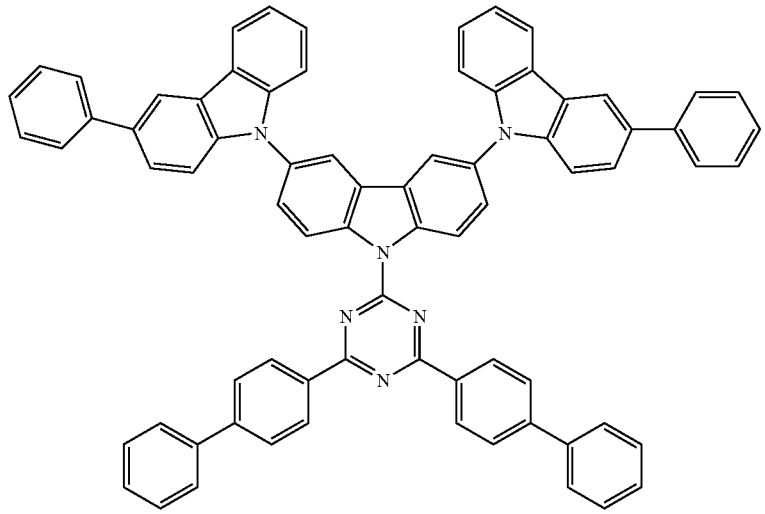 [SMILES: c1ccc(-c2ccc(-c3nc(-c4ccc(-c5ccccc5)cc4)nc(-n4c5ccc(-n6c7ccccc7c7cc(-c8ccccc8)ccc76)cc5c5cc(-n6c7ccccc7c7cc(-c8ccccc8)ccc76)ccc54)n3)cc2)cc1]
Compound 1-35
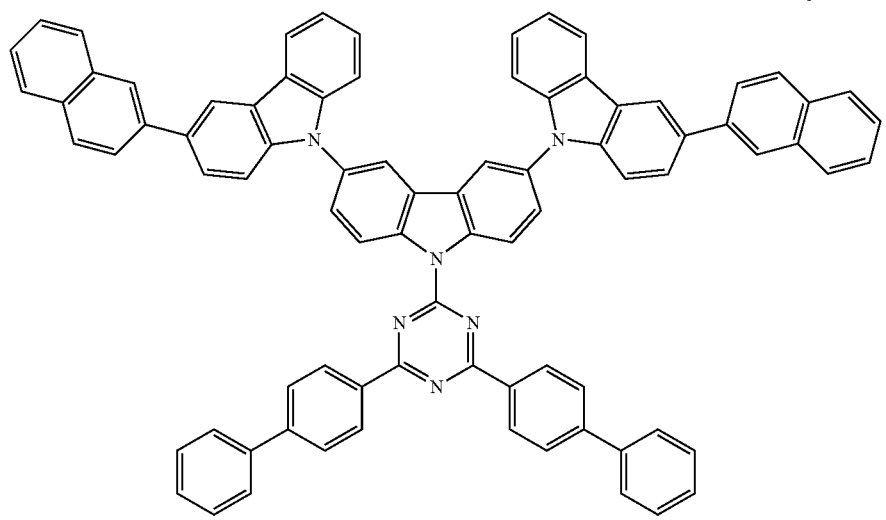
Compound 1-36

TABLE 1-continued
Compound 1-37
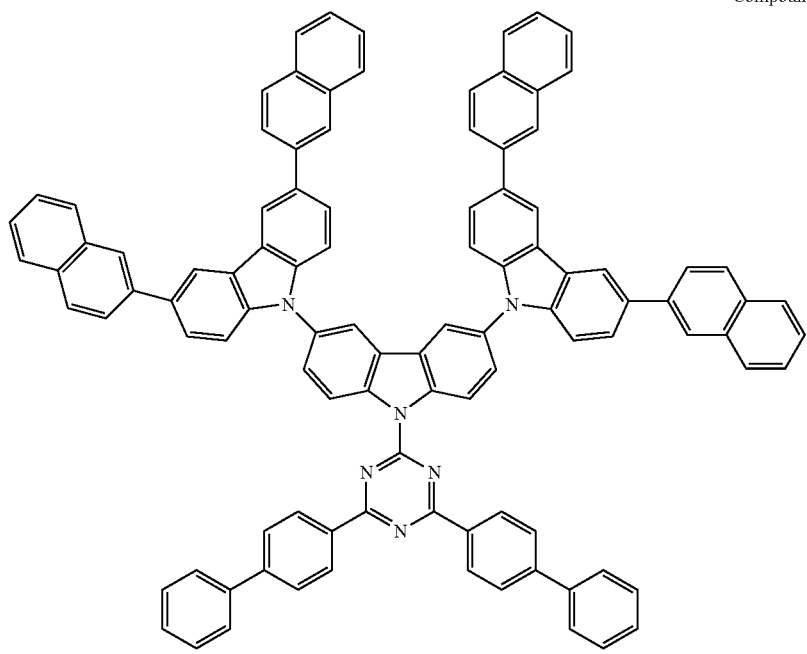
Compound 1-38
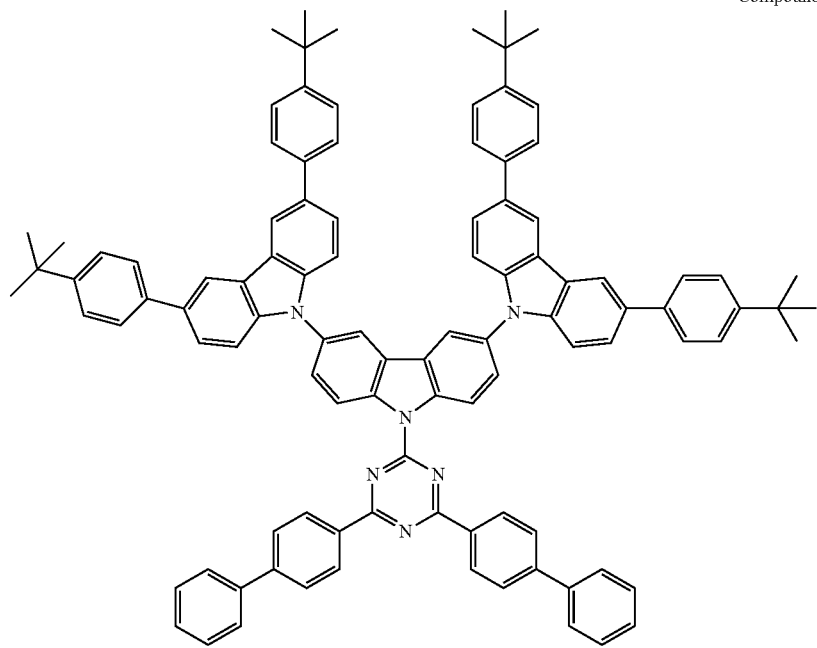

TABLE 1-continued
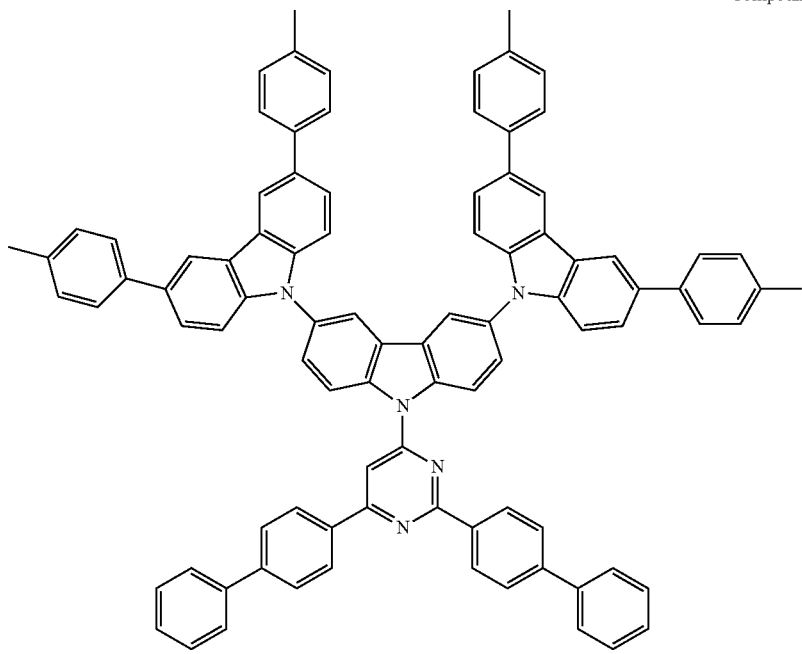
Compound 1-39
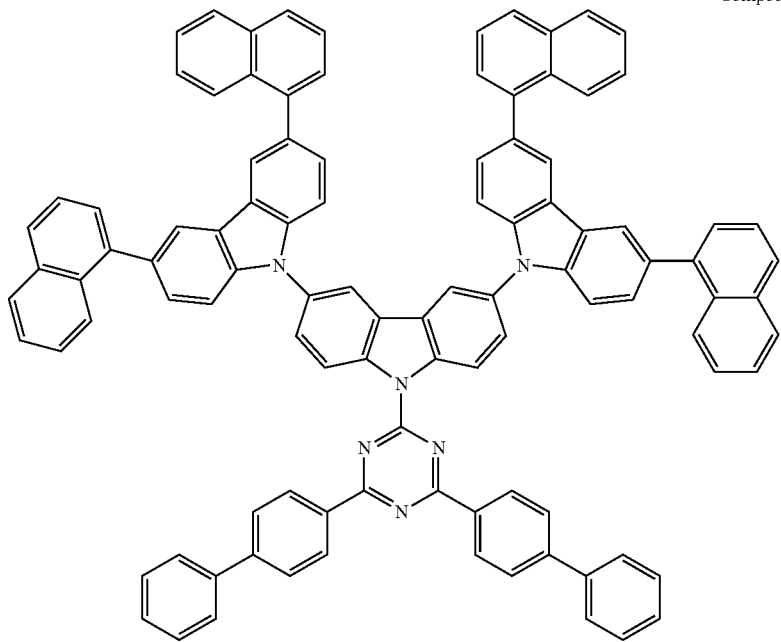
Compound 1-40

TABLE 1-continued
Compound 1-41
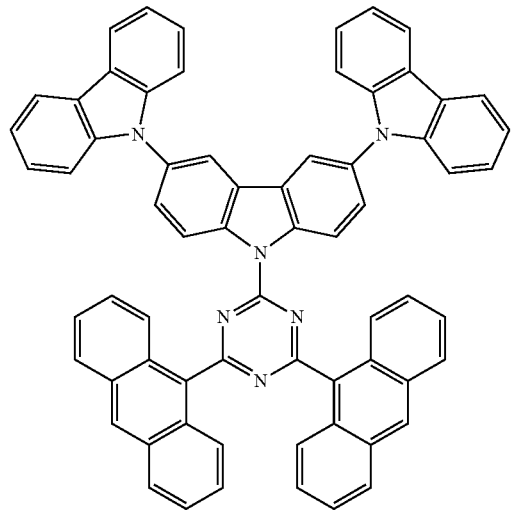 [SMILES: c1ccc2c(-c3nc(-c4c5ccccc5cc5ccccc45)nc(-n4c5ccc(-n6c7ccccc7c7ccccc76)cc5c5cc(-n6c7ccccc7c7ccccc76)ccc54)n3)c3ccccc3cc2c1]
Compound 1-42
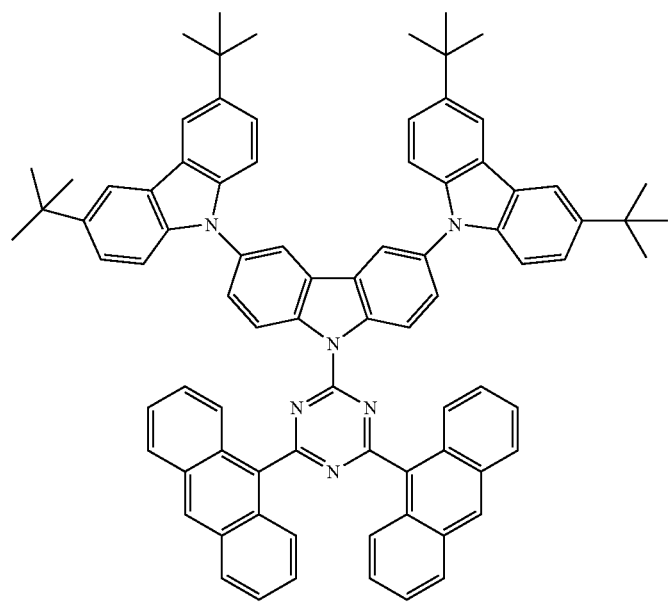 [SMILES: CC(C)(C)c1ccc2c(c1)c1cc(C(C)(C)C)ccc1n2-c1ccc2c(c1)c1cc(-n3c4ccc(C(C)(C)C)cc4c4cc(C(C)(C)C)ccc43)ccc1n2-c1nc(-c2c3ccccc3cc3ccccc23)nc(-c2c3ccccc3cc3ccccc23)n1]

TABLE 1-continued
Compound 1-43
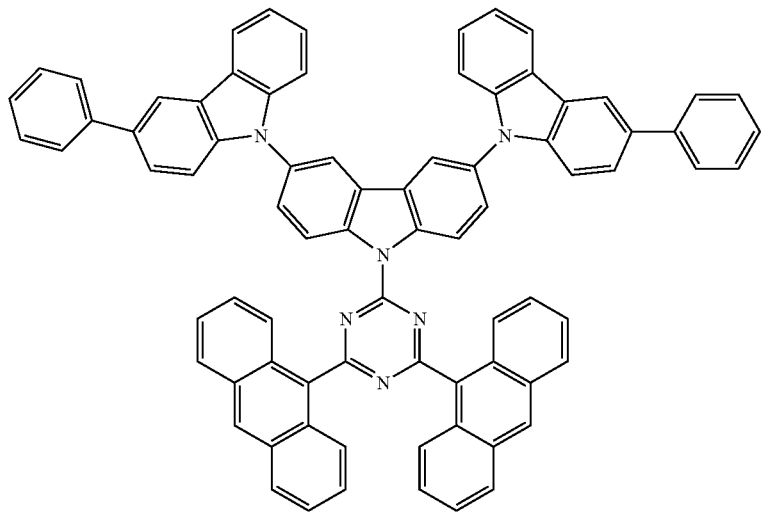 [SMILES: c1ccc(-c2ccc3c(c2)c2ccccc2n3-c2ccc3c(c2)c2cc(-n4c5ccccc5c5cc(-c6ccccc6)ccc54)ccc2n3-c2nc(-c3c4ccccc4cc4ccccc34)nc(-c3c4ccccc4cc4ccccc34)n2)cc1]
Compound 1-44
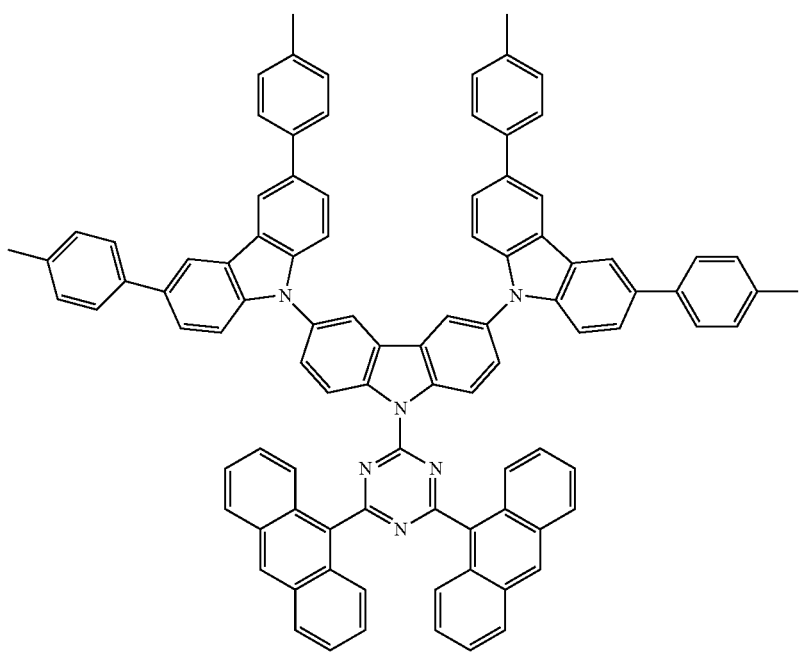

TABLE 1-continued
Compound 1-45
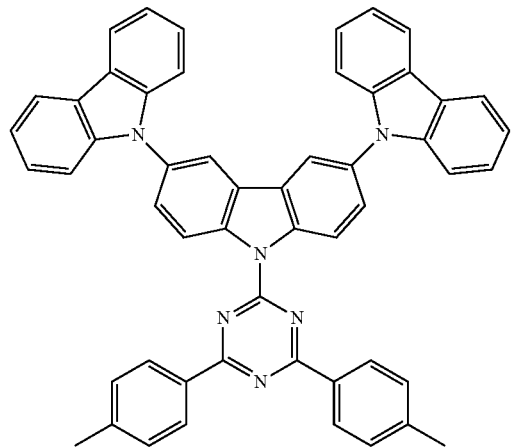 [SMILES: Cc1ccc(-c2nc(-c3ccc(C)cc3)nc(-n3c4ccc(-n5c6ccccc6c6ccccc65)cc4c4cc(-n5c6ccccc6c6ccccc65)ccc43)n2)cc1]
Compound 1-46
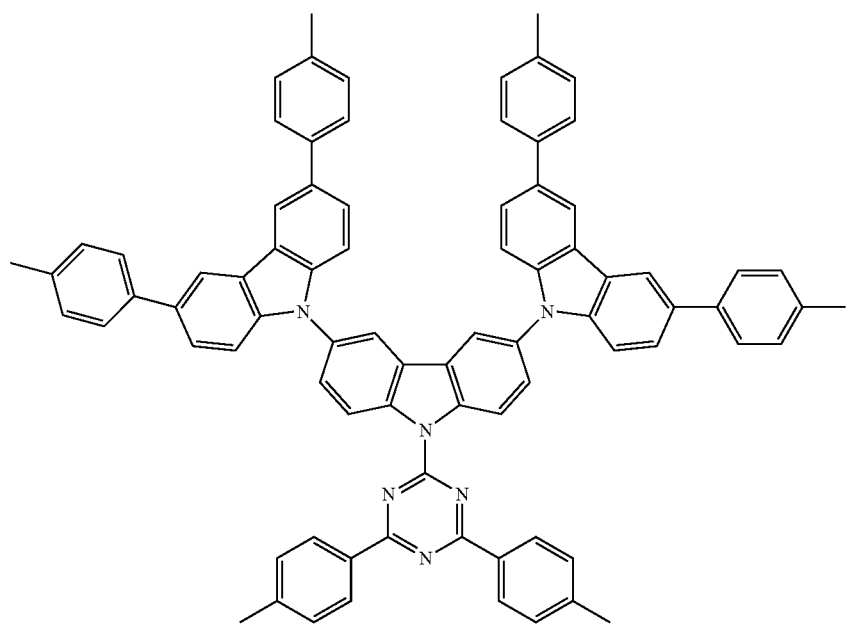

TABLE 1-continued
Compound 1-47
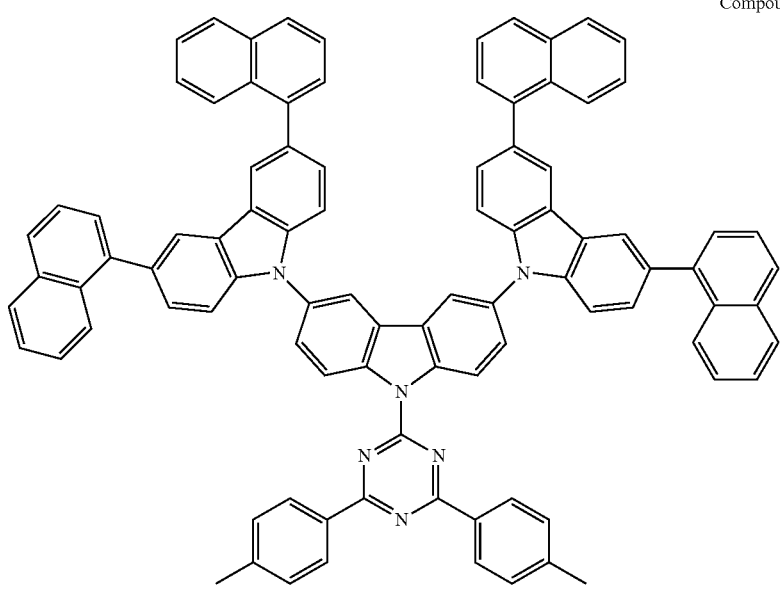
Compound 1-48
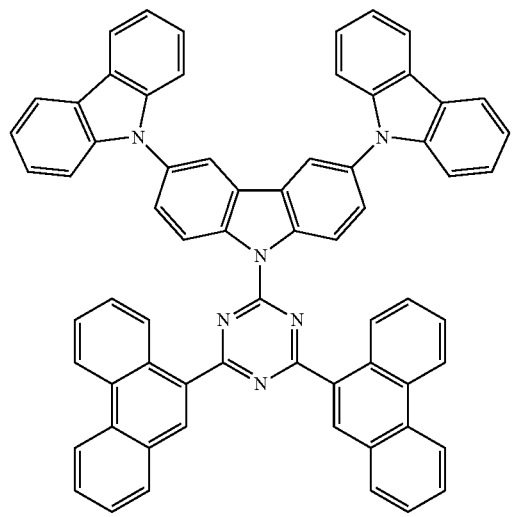 [SMILES: c1ccc2c(c1)cc(-c1nc(-c3cc4ccccc4c4ccccc34)nc(-n3c4ccc(-n5c6ccccc6c6ccccc65)cc4c4cc(-n5c6ccccc6c6ccccc65)ccc43)n1)c1ccccc12]
Compound 1-49
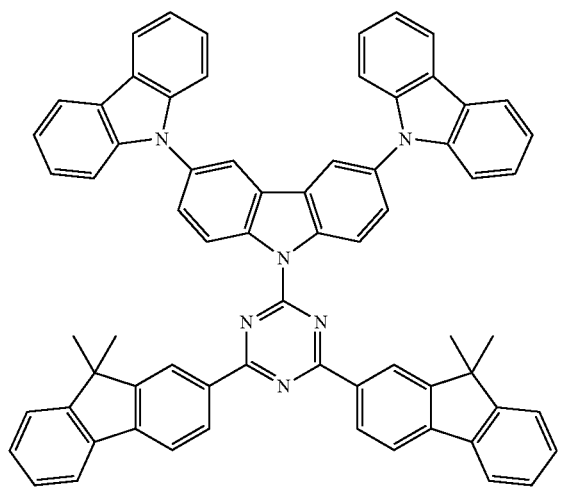 [SMILES: CC1(C)c2ccccc2-c2ccc(-c3nc(-c4ccc5c(c4)C(C)(C)c4ccccc4-5)nc(-n4c5ccc(-n6c7ccccc7c7ccccc76)cc5c5cc(-n6c7ccccc7c7ccccc76)ccc54)n3)cc21]

TABLE 1-continued
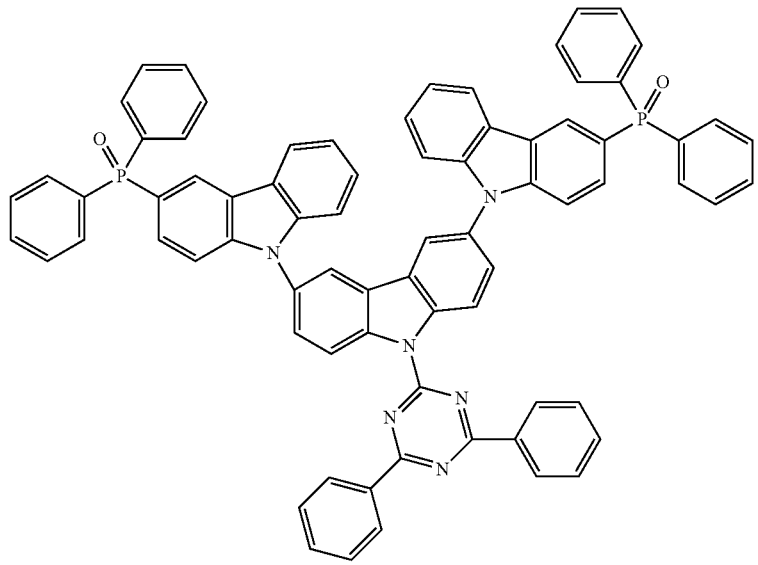 [SMILES: O=P(c1ccccc1)(c1ccccc1)c1ccc2c(c1)c1ccccc1n2-c1ccc2c(c1)c1cc(-n3c4ccccc4c4cc(P(=O)(c5ccccc5)c5ccccc5)ccc43)ccc1n2-c1nc(-c2ccccc2)nc(-c2ccccc2)n1]
Compound 1-50
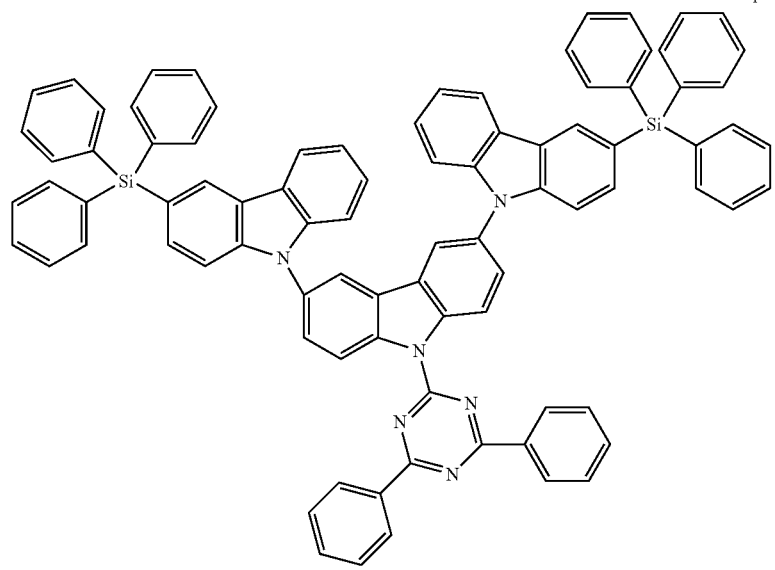
Compound 1-51

TABLE 1-continued

Compound 1-52

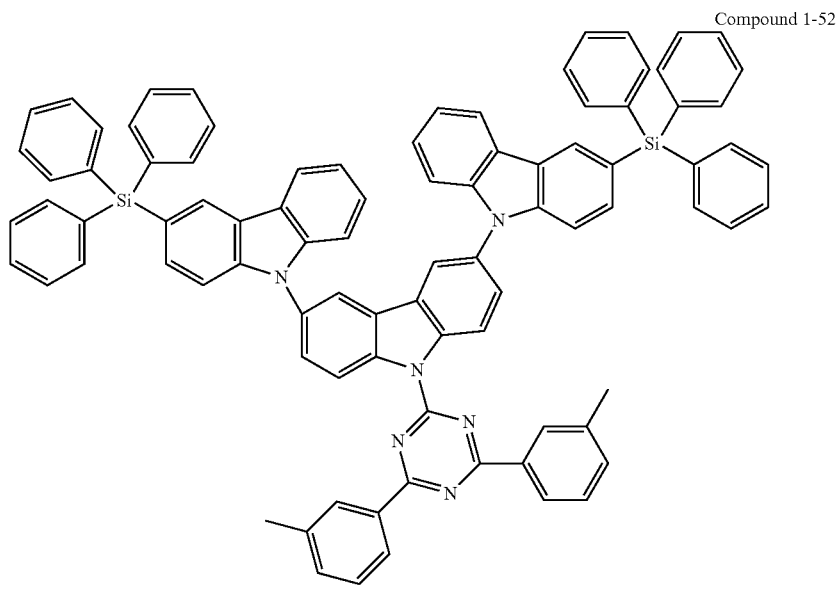

General formula (III) corresponds to general formula (I) wherein X and Y each independently represent a carbazolyl group represented by formula (A), and may be linked at C-3 of the carbazole unit in the basic molecular skeleton of formula (I). Compounds 2-1 to 2-10 shown in Table 2 are represented by formula (III), wherein m=1, n=0 and m+n=1

TABLE 2

Compound 2-1

TABLE 2-continued

Compound 2-2

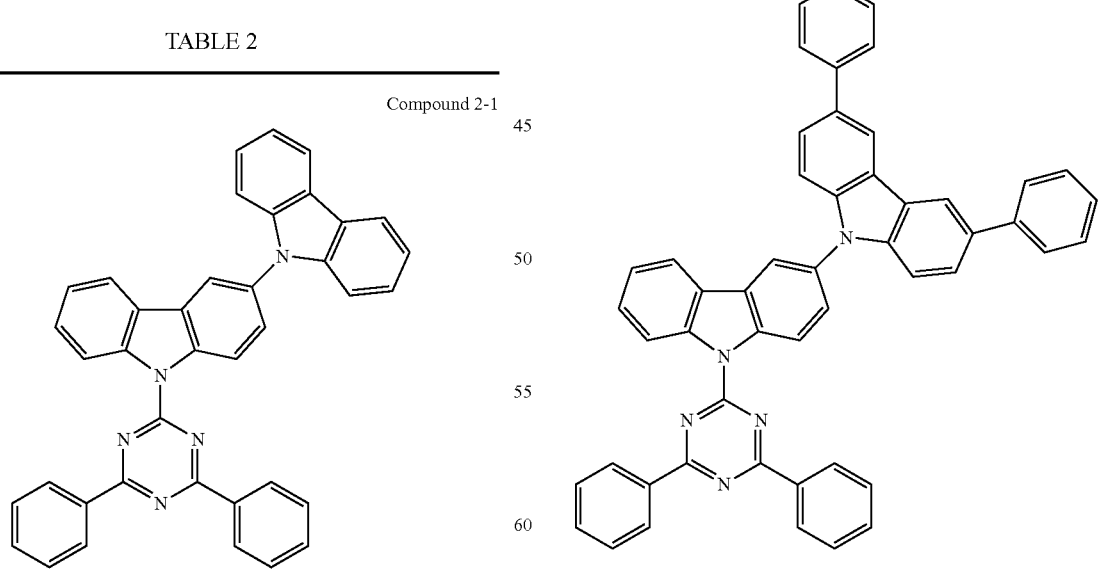

TABLE 2-continued
Compound 2-3
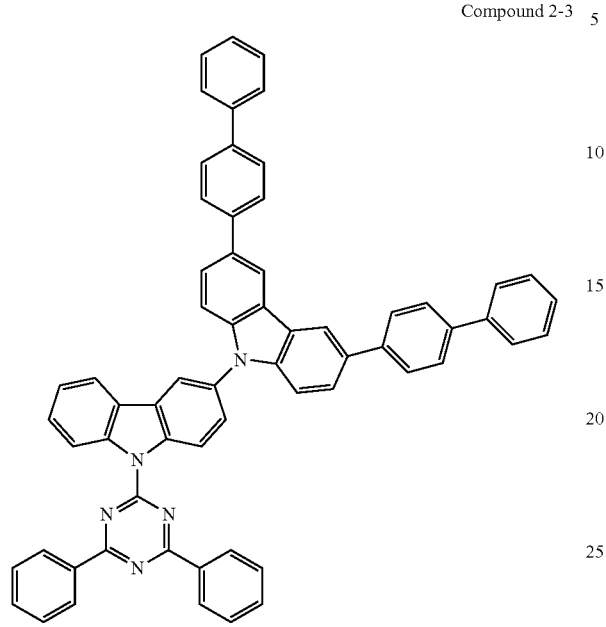
Compound 2-4
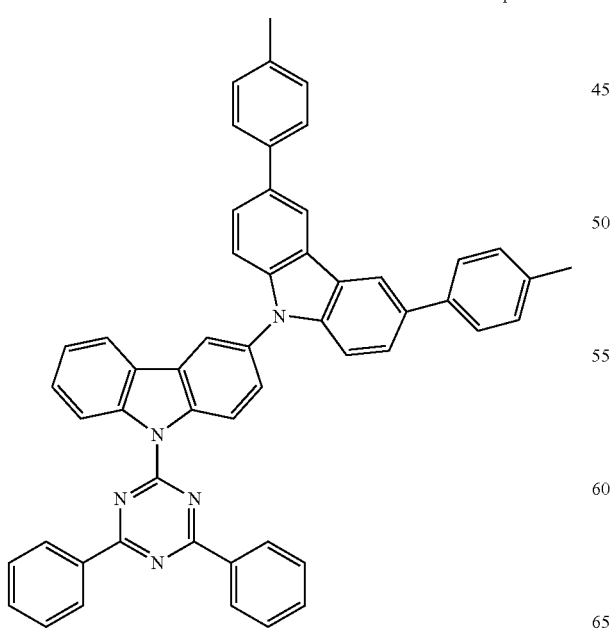
TABLE 2-continued
Compound 2-5
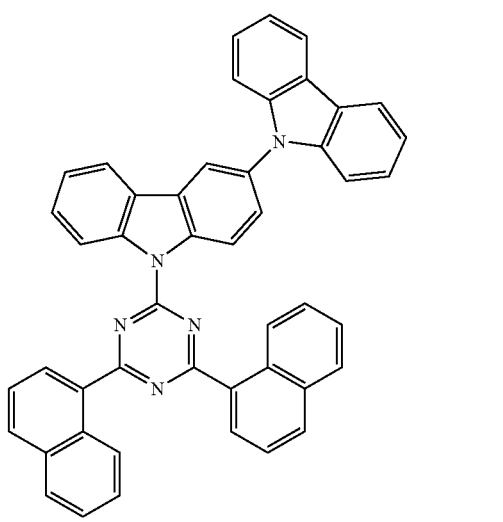 [SMILES: c1ccc2c(-c3nc(-c4cccc5ccccc45)nc(-n4c5ccccc5c5cc(-n6c7ccccc7c7ccccc76)ccc54)n3)cccc2c1]
Compound 2-6
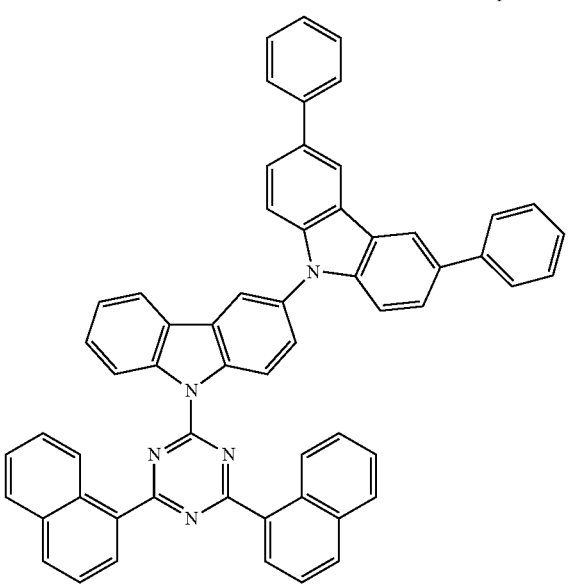

TABLE 2-continued
Compound 2-7
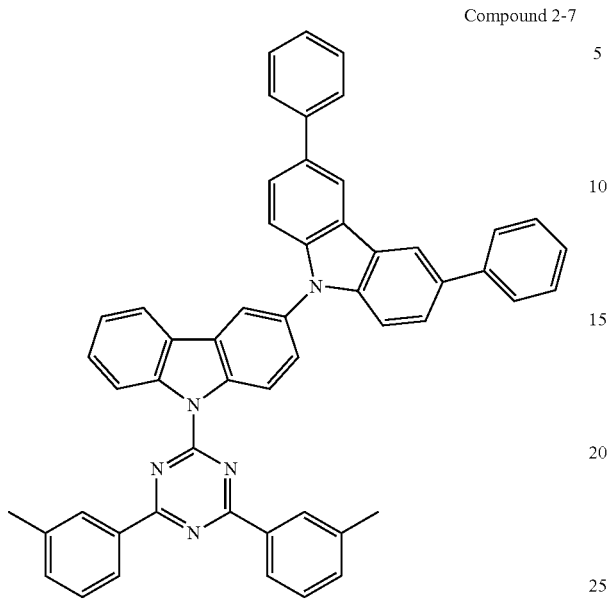
Compound 2-8
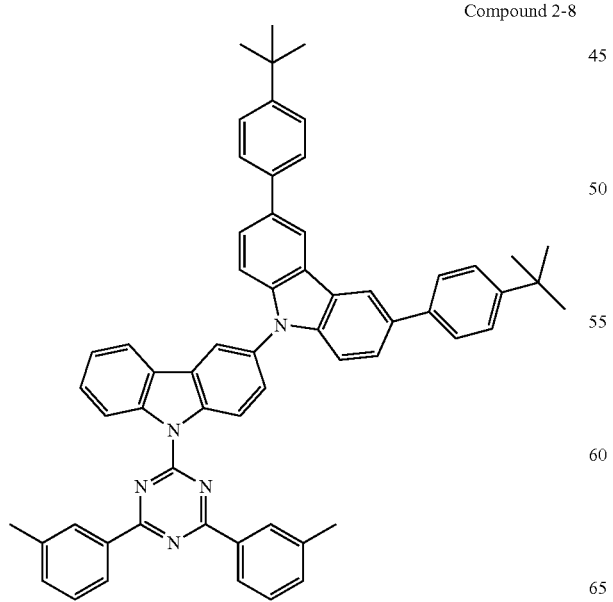
TABLE 2-continued
Compound 2-9
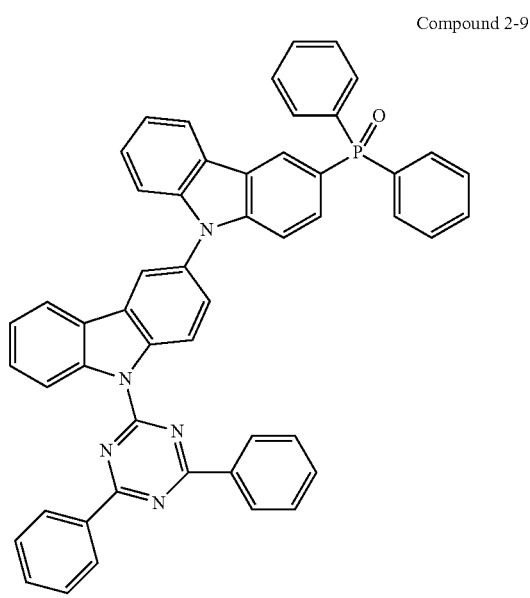
Compound 2-10
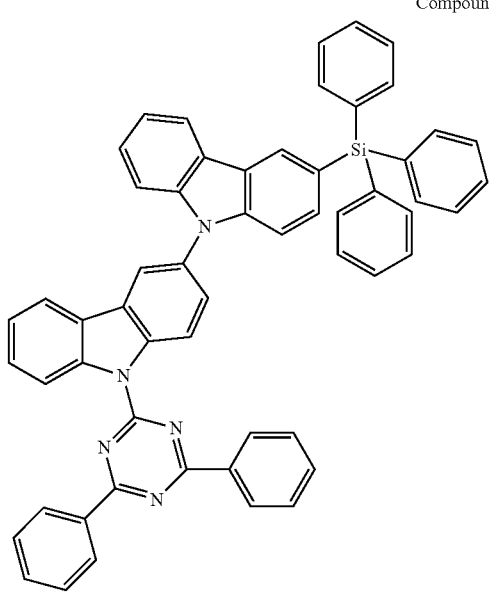

TABLE 2-continued

Compound 2-11

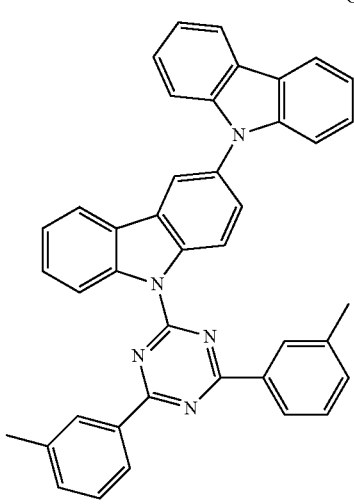

General formula (IV) corresponds to general formula (I) wherein X and Y each independently represent an indolocarbazolyl group represented by formula (C), and may be linked at C-3 and C-6 of the carbazole unit in the basic molecular skeleton of formula (I). Compounds 3-1 to 3-7 shown in Table 3 are represented by formula (IV), wherein m=1, n=1 and m+n=2.

General formula (V) corresponds to general formula (I) wherein X and Y each independently represent an indolocarbazolyl group represented by formula (C), and may be linked at C-3 of the carbazole unit in the basic molecular skeleton of formula (I). Compounds 3-8 to 3-13 shown in Table 3 are represented by formula (V), wherein m=1, n=0 and m+n=1.

TABLE 3

Compound 3-1

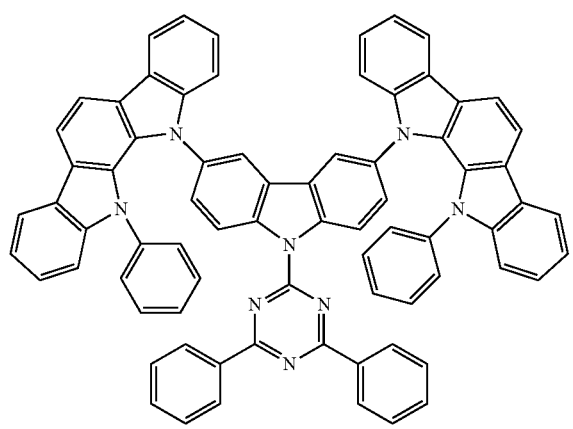 [SMILES: c1ccc(-c2nc(-c3ccccc3)nc(-n3c4ccc(-n5c6ccccc6c6ccc7c8ccccc8n(-c8ccccc8)c7c65)cc4c4cc(-n5c6ccccc6c6ccc7c8ccccc8n(-c8ccccc8)c7c65)ccc43)n2)cc1]

TABLE 3-continued

Compound 3-2

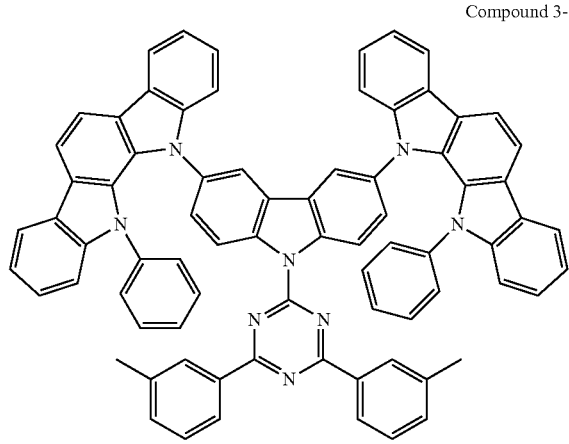

Compound 3-3

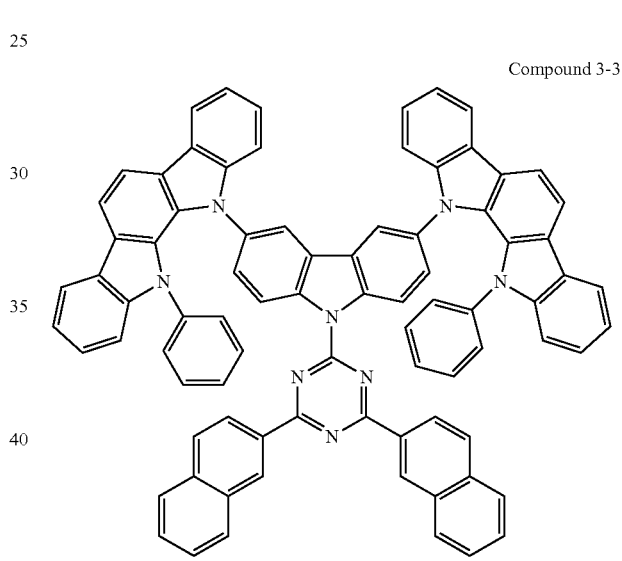

Compound 3-4

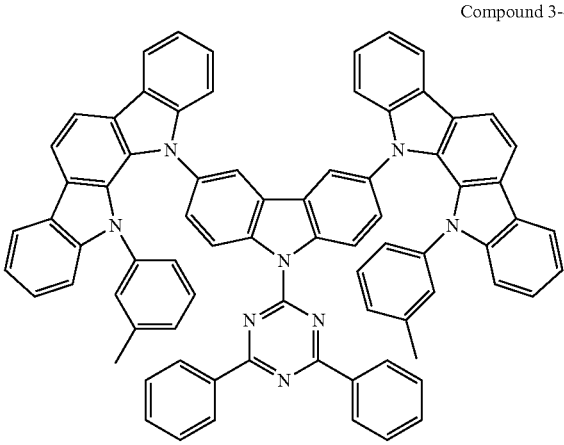

TABLE 3-continued
Compound 3-5
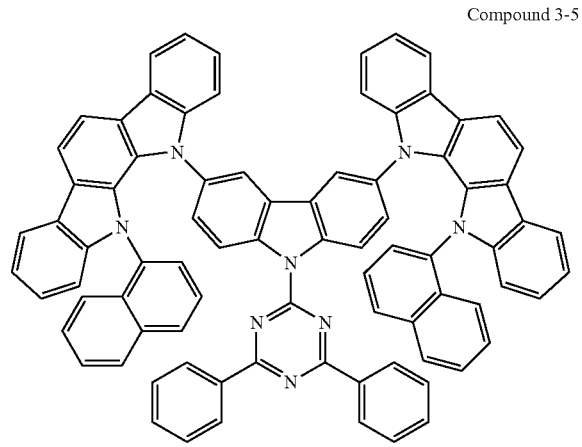
Compound 3-6
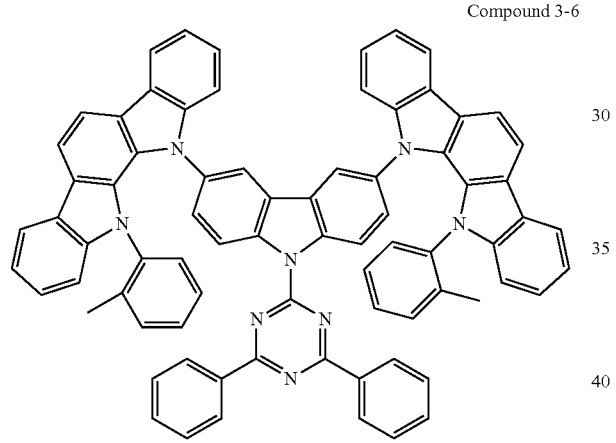
Compound 3-7
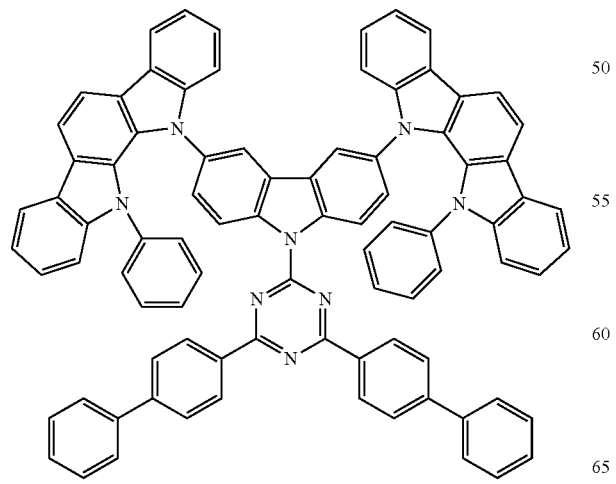
TABLE 3-continued
Compound 3-8
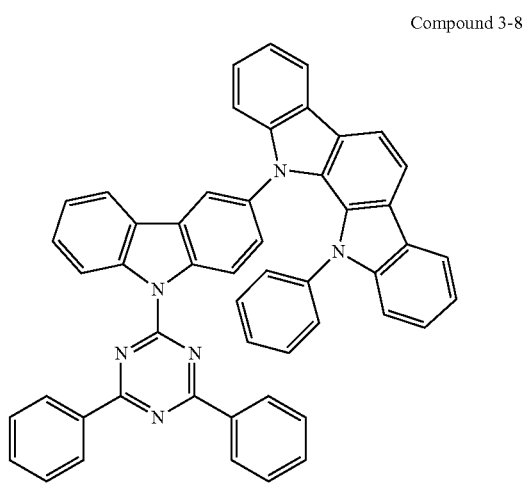
Compound 3-9
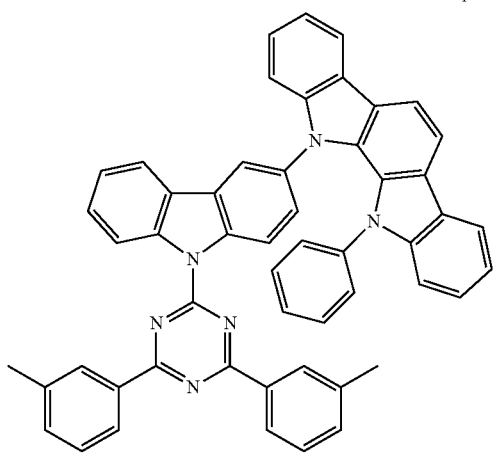
Compound 3-10
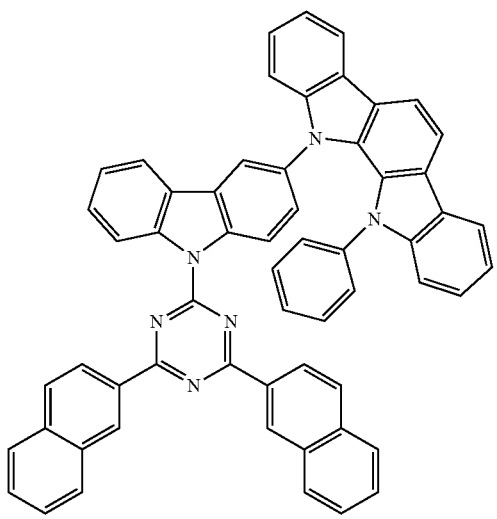 [SMILES: c1ccc(-n2c3ccccc3c3ccc4c5ccccc5n(-c5ccc6c(c5)c5ccccc5n6-c5nc(-c6ccc7ccccc7c6)nc(-c6ccc7ccccc7c6)n5)c4c32)cc1]

TABLE 3-continued

Compound 3-11

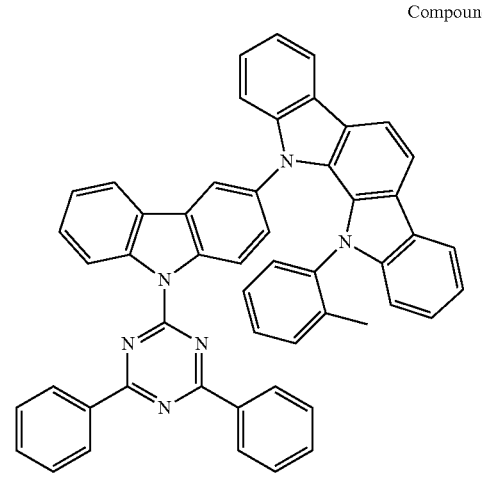

Compound 3-12

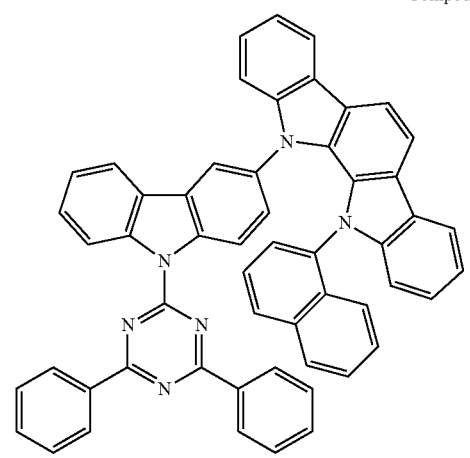

Compound 3-13

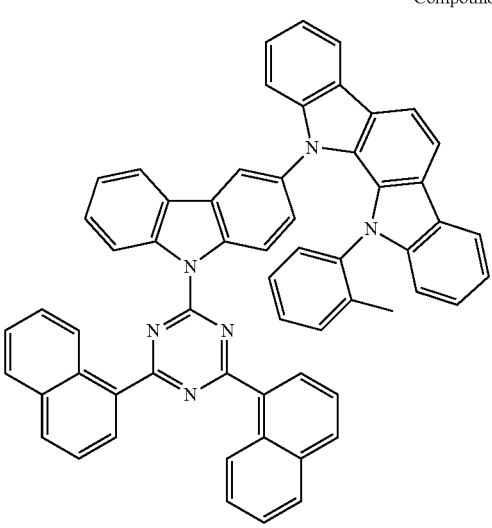

TABLE 3-continued

Compound 3-14

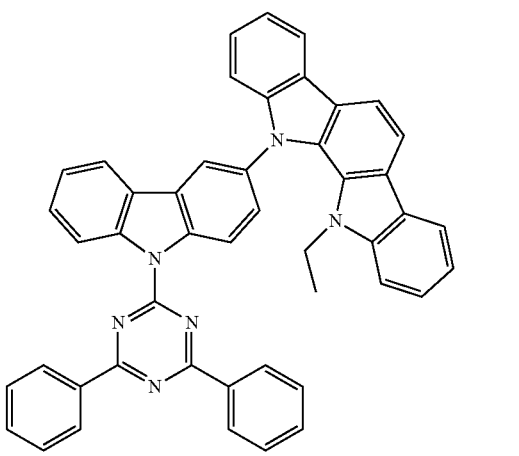 [SMILES: CCn1c2ccccc2c2ccc3c4ccccc4n(-c4ccc5c(c4)c4ccccc4n5-c4nc(-c5ccccc5)nc(-c5ccccc5)n4)c3c21]

Compound 3-15

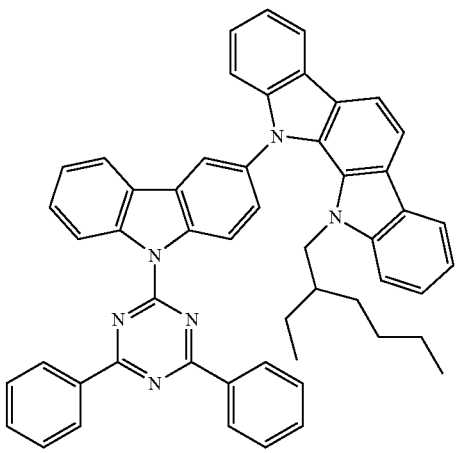 [SMILES: CCCCC(CC)Cn1c2ccccc2c2ccc3c4ccccc4n(-c4ccc5c(c4)c4ccccc4n5-c4nc(-c5ccccc5)nc(-c5ccccc5)n4)c3c21]

General formula (VI) corresponds to general formula (I) wherein X and Y each independently represent a carbazolyl group represented by formula (A), and may be linked at C-2 and C-7 of the carbazole unit in the basic molecular skeleton of formula (I). Compounds 4-1 to 4-5 shown in Table 4 are represented by formula (VI), wherein m=1, n=1 and m+n=2.

General formula (VII) corresponds to general formula (I) wherein X and Y each independently represent an indolocarbazolyl group represented by formula (C), and may be linked at C-2 and C-7 of the carbazole unit in the basic molecular skeleton of formula (I). Compounds 4-6 to 4-9 shown in Table 4 are represented by formula (VII), wherein m=1, n=1 and m+n=2.

TABLE 4
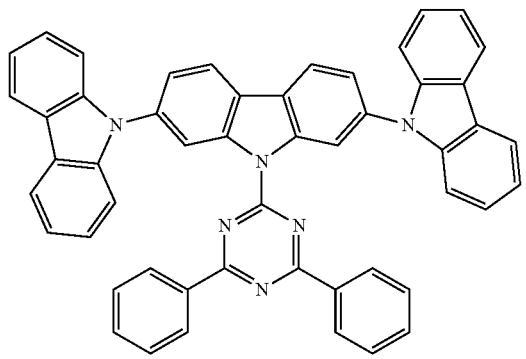 [SMILES: c1ccc(-c2nc(-c3ccccc3)nc(-n3c4cc(-n5c6ccccc6c6ccccc65)ccc4c4ccc(-n5c6ccccc6c6ccccc65)cc43)n2)cc1]
Compound 4-1
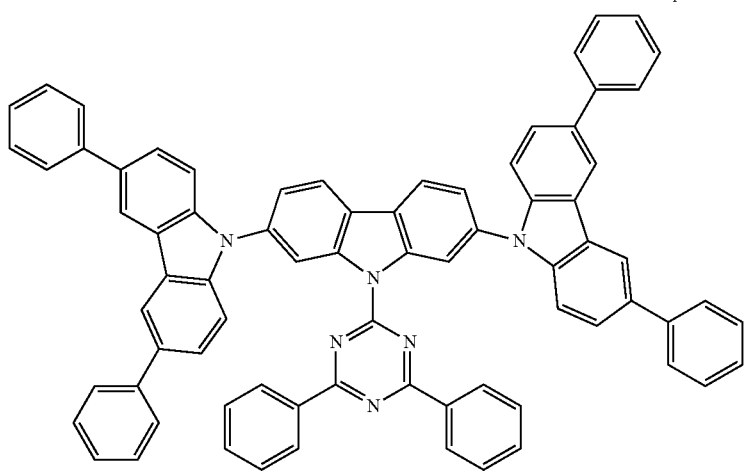
Compound 4-2
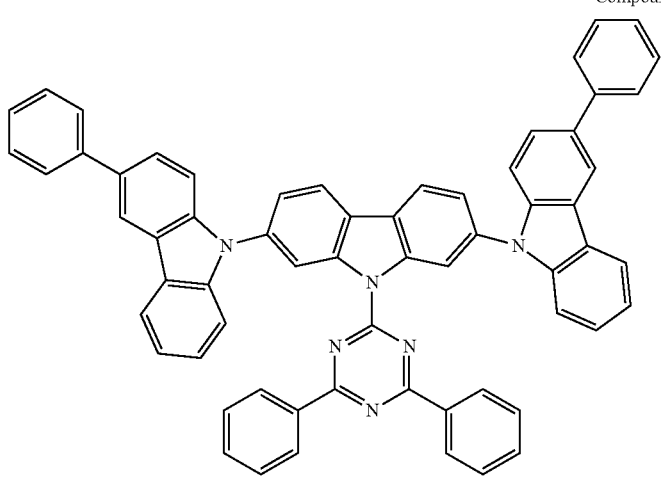
Compound 4-3

TABLE 4-continued
Compound 4-4
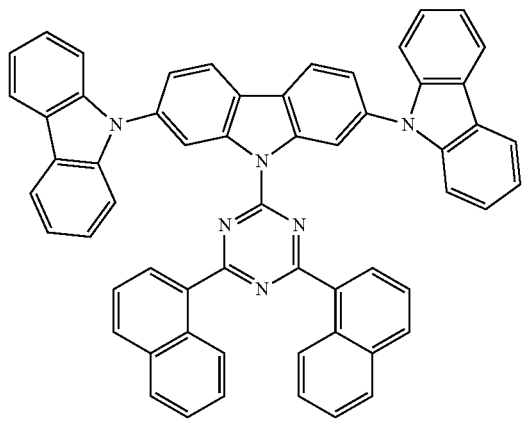 [SMILES: c1ccc2c(-c3nc(-c4cccc5ccccc45)nc(-n4c5cc(-n6c7ccccc7c7ccccc76)ccc5c5ccc(-n6c7ccccc7c7ccccc76)cc54)n3)cccc2c1]
Compound 4-5
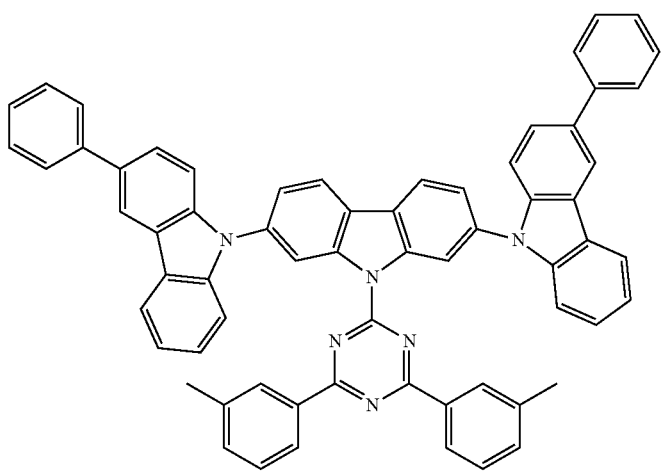 [SMILES: Cc1cccc(-c2nc(-c3cccc(C)c3)nc(-n3c4cc(-n5c6ccccc6c6cc(-c7ccccc7)ccc65)ccc4c4ccc(-n5c6ccccc6c6cc(-c7ccccc7)ccc65)cc43)n2)c1]
Compound 4-6
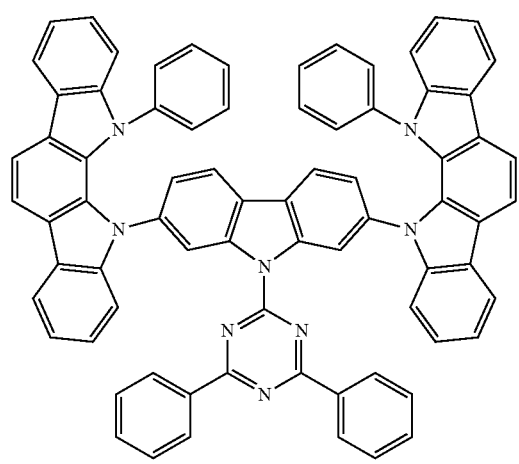 [SMILES: c1ccc(-c2nc(-c3ccccc3)nc(-n3c4cc(-n5c6ccccc6c6ccc7c8ccccc8n(-c8ccccc8)c7c65)ccc4c4ccc(-n5c6ccccc6c6ccc7c8ccccc8n(-c8ccccc8)c7c65)cc43)n2)cc1]

TABLE 4-continued
Compound 4-7
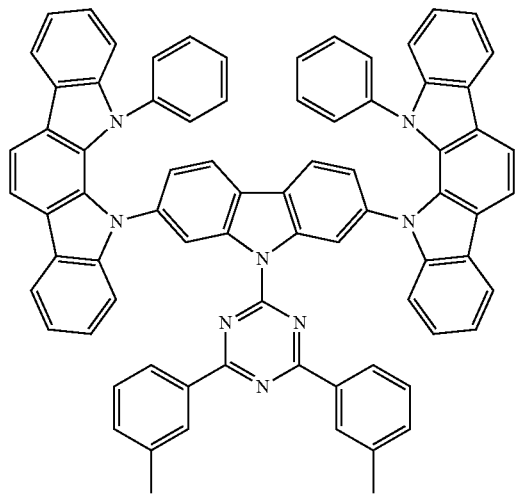 [SMILES: Cc1cccc(-c2nc(-c3cccc(C)c3)nc(-n3c4cc(-n5c6ccccc6c6ccc7c8ccccc8n(-c8ccccc8)c7c65)ccc4c4ccc(-n5c6ccccc6c6ccc7c8ccccc8n(-c8ccccc8)c7c65)cc43)n2)c1]
Compound 4-8
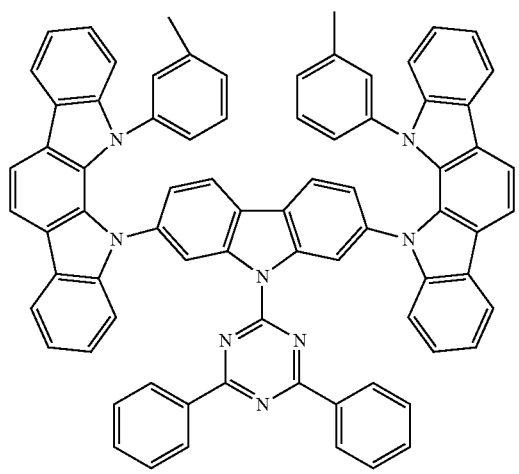 [SMILES: Cc1cccc(-n2c3ccccc3c3ccc4c5ccccc5n(-c5ccc6c7ccc(-n8c9ccccc9c9ccc%10c%11ccccc%11n(-c%11cccc(C)c%11)c%10c98)cc7n(-c7nc(-c8ccccc8)nc(-c8ccccc8)n7)c6c5)c4c32)c1]
Compound 4-9
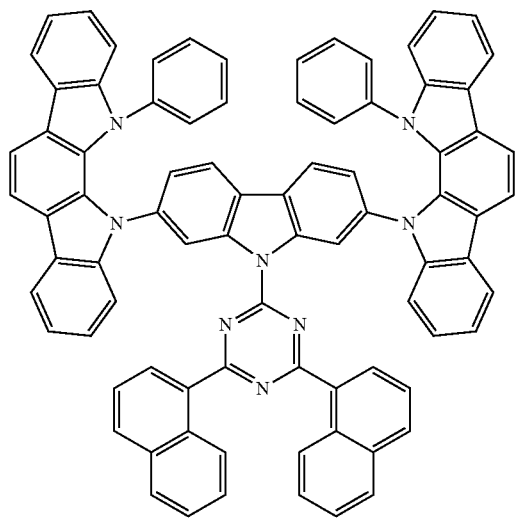 [SMILES: c1ccc(-n2c3ccccc3c3ccc4c5ccccc5n(-c5ccc6c7ccc(-n8c9ccccc9c9ccc%10c%11ccccc%11n(-c%11ccccc%11)c%10c98)cc7n(-c7nc(-c8cccc9ccccc89)nc(-c8cccc9ccccc89)n7)c6c5)c4c32)cc1]

General formula (VIII) corresponds to general formula (I) wherein X and Y each independently represent a carbazolyl group represented by formula (B), and may be linked at C-3 and C-6 of the carbazole unit in the basic molecular skeleton of formula (I). Compounds 5-1 to 5-10 shown in Table 5 are represented by formula (VIII), wherein m=1, n=1 and m+n=2.
TABLE 5
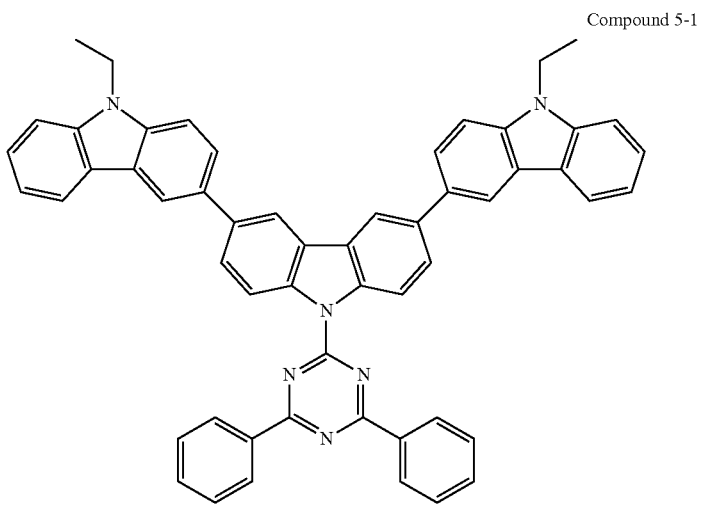
Compound 5-1
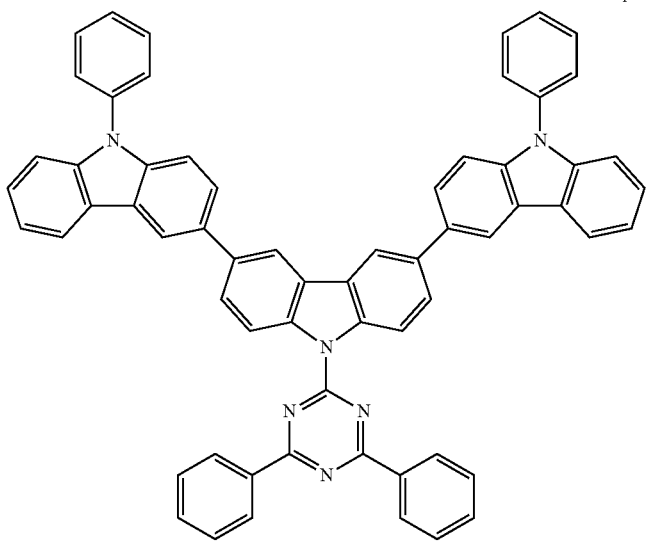
Compound 5-2

TABLE 5-continued
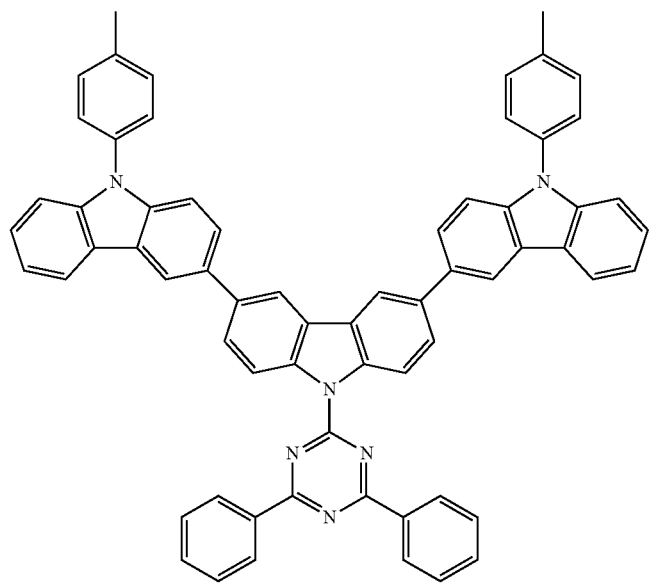 [SMILES: Cc1ccc(-n2c3ccccc3c3cc(-c4ccc5c(c4)c4cc(-c6ccc7c(c6)c6ccccc6n7-c6ccc(C)cc6)ccc4n5-c4nc(-c5ccccc5)nc(-c5ccccc5)n4)ccc32)cc1]
Compound 5-3
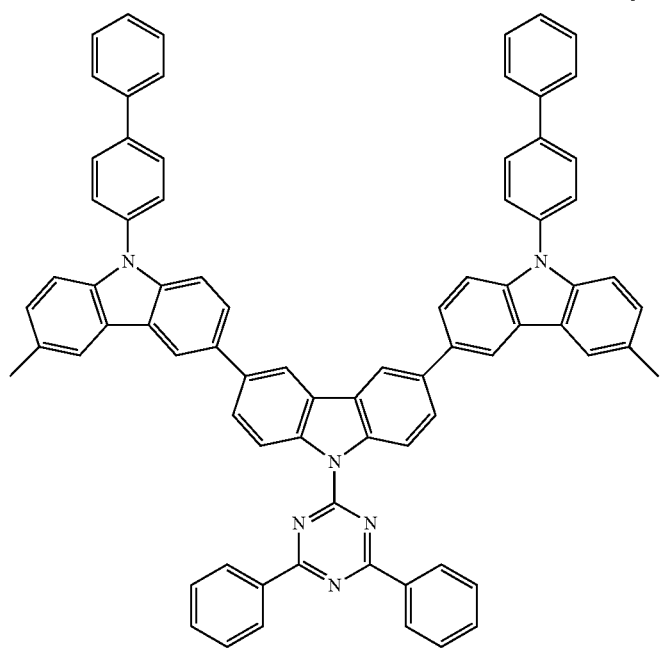
Compound 5-4

TABLE 5-continued
Compound 5-5
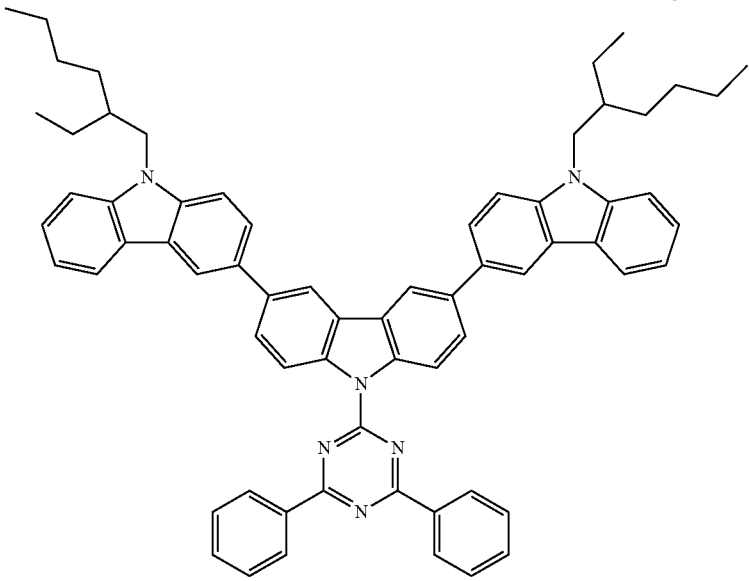 [SMILES: CCCCC(CC)Cn1c2ccccc2c2cc(-c3ccc4c(c3)c3cc(-c5ccc6c(c5)c5ccccc5n6CC(CC)CCCC)ccc3n4-c3nc(-c4ccccc4)nc(-c4ccccc4)n3)ccc21]
Compound 5-6
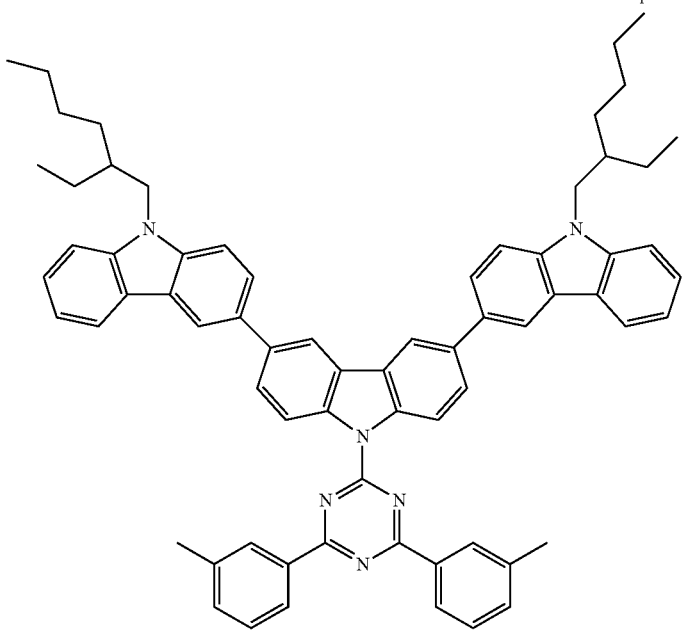

TABLE 5-continued
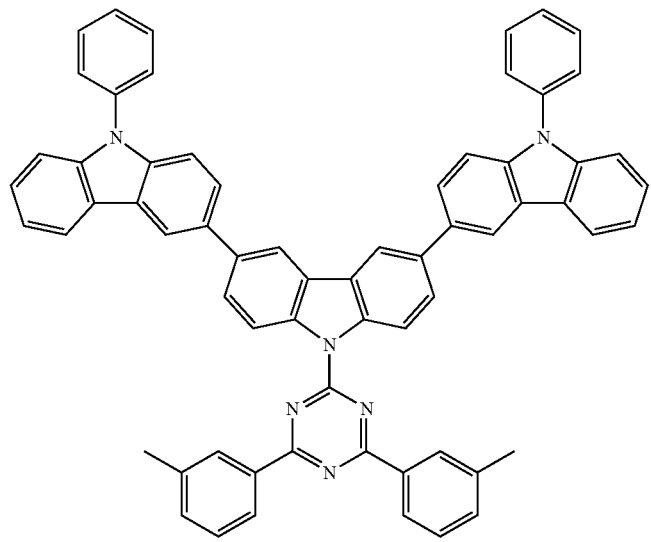 [SMILES: Cc1cccc(-c2nc(-c3cccc(C)c3)nc(-n3c4ccc(-c5ccc6c(c5)c5ccccc5n6-c5ccccc5)cc4c4cc(-c5ccc6c(c5)c5ccccc5n6-c5ccccc5)ccc43)n2)c1]
Compound 5-7
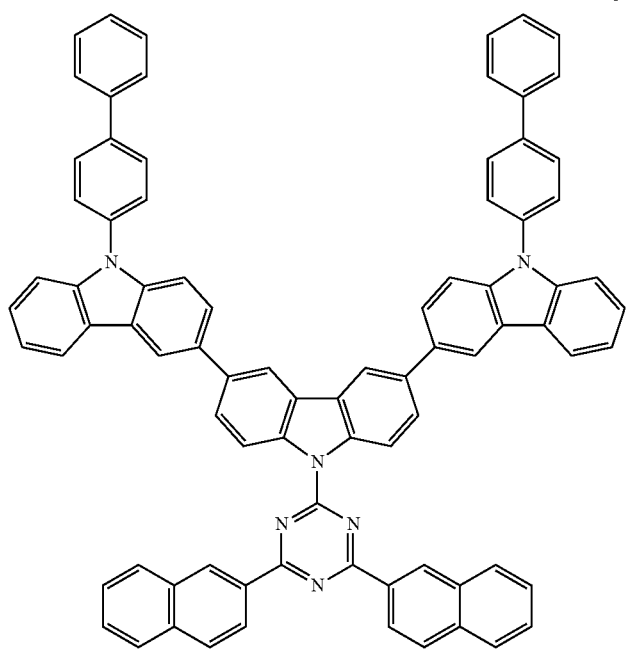
Compound 5-8

TABLE 5-continued
Compound 5-9
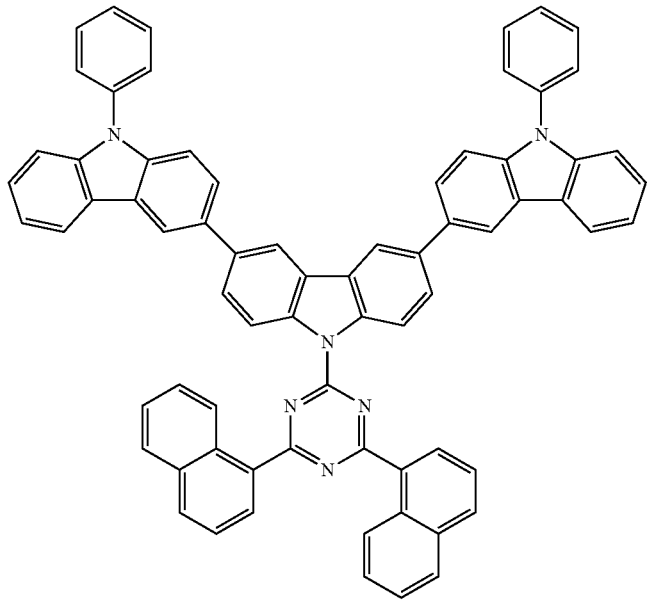 [SMILES: c1ccc(-n2c3ccccc3c3cc(-c4ccc5c(c4)c4cc(-c6ccc7c(c6)c6ccccc6n7-c6ccccc6)ccc4n5-c4nc(-c5cccc6ccccc56)nc(-c5cccc6ccccc56)n4)ccc32)cc1]
Compound 5-10
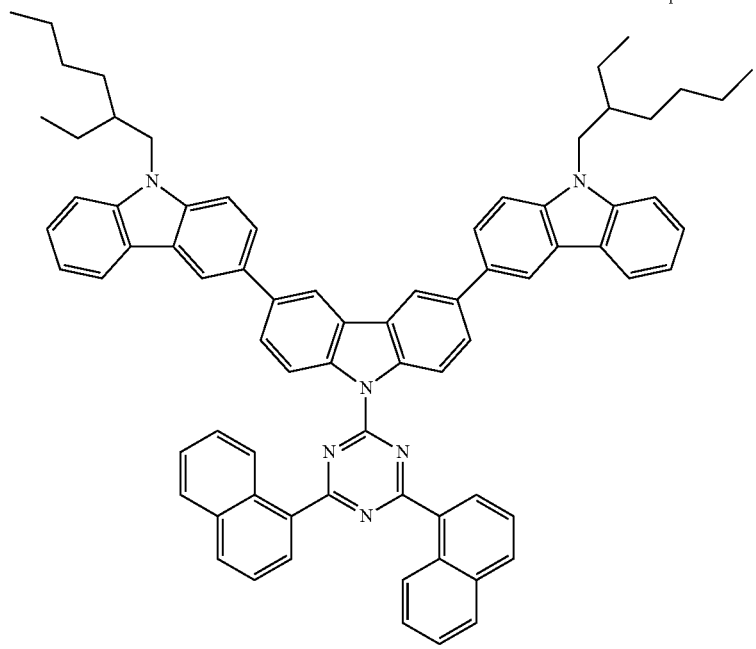

General formula (IX) corresponds to general formula (I) wherein X and Y each independently represent a carbazolyl group represented by formula (B), and may be linked at C-3 of the carbazole unit in the basic molecular skeleton of formula (I). Compounds 6-1 to 6-5 shown in Table 6 are represented by formula (IX), wherein m=1, n=0 and m+n=1.

TABLE 6

Compound 6-1

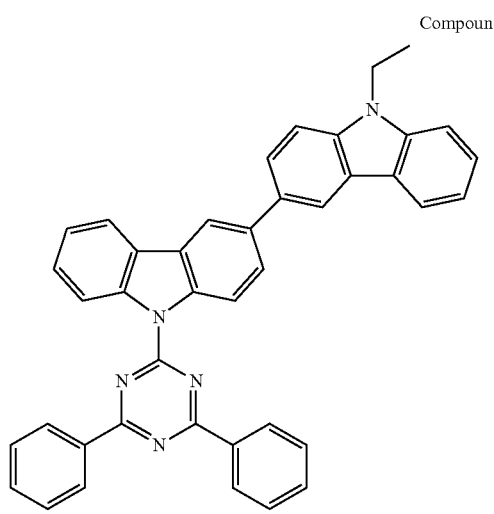

Compound 6-2

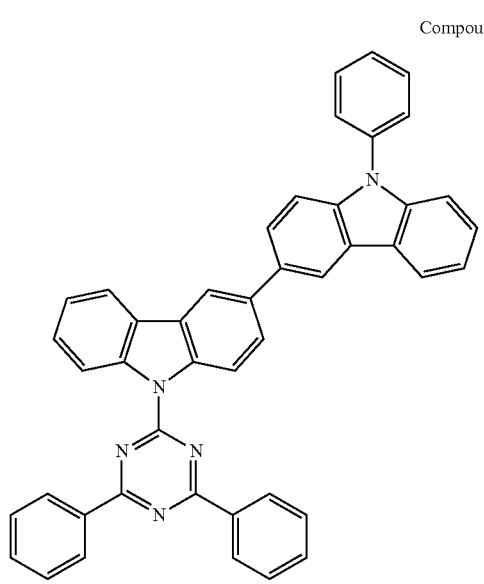

TABLE 6-continued

Compound 6-3

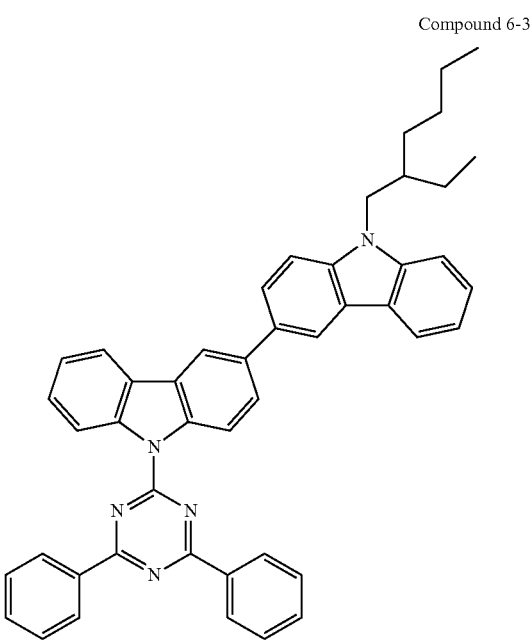

Compound 6-4

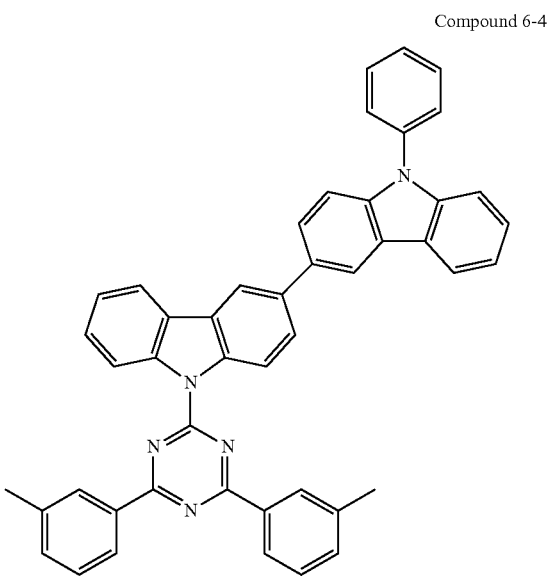

TABLE 6-continued

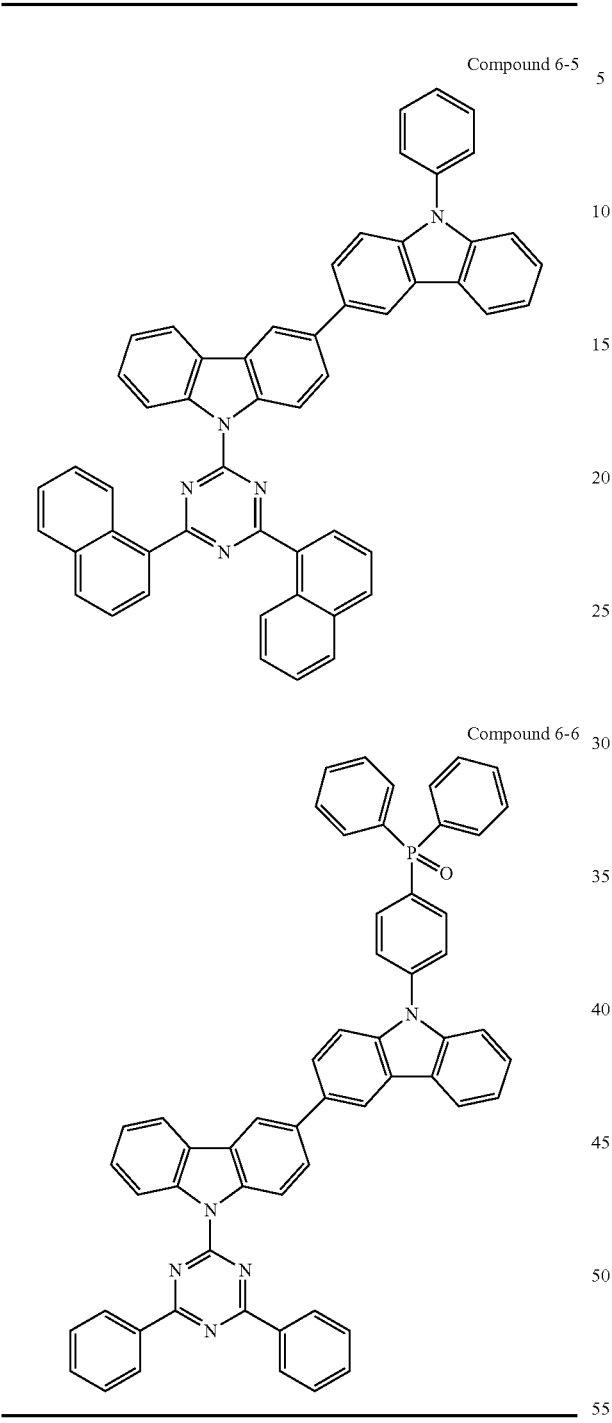

Compound 6-5

Compound 6-6

TABLE 7

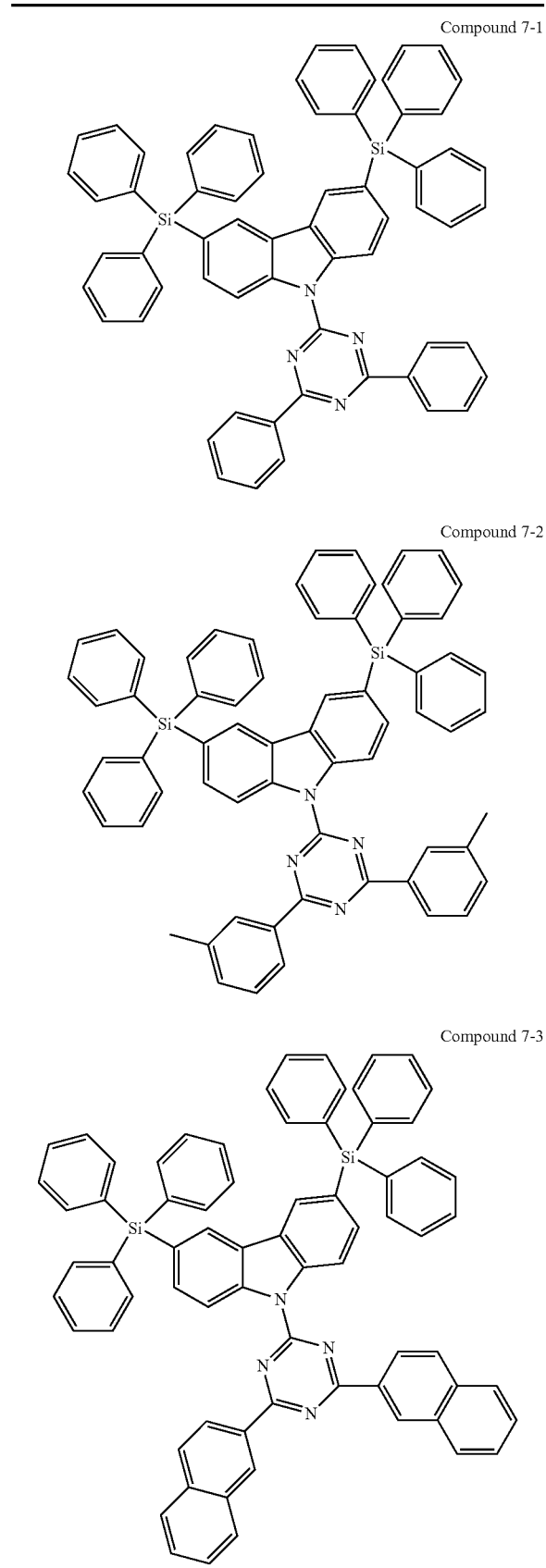

Compound 7-1

Compound 7-2

Compound 7-3

General formula (X) corresponds to general formula (I) wherein X and Y each independently represent a triphenyl silyl group represented by formula (D), and may be linked at C-3 and C-6 of the carbazole unit in the basic molecular skeleton of formula (I). Compounds 7-1 to 7-5 shown in Table 7 are represented by formula (X), wherein m=1, n=1 and m+n=2.

TABLE 7-continued

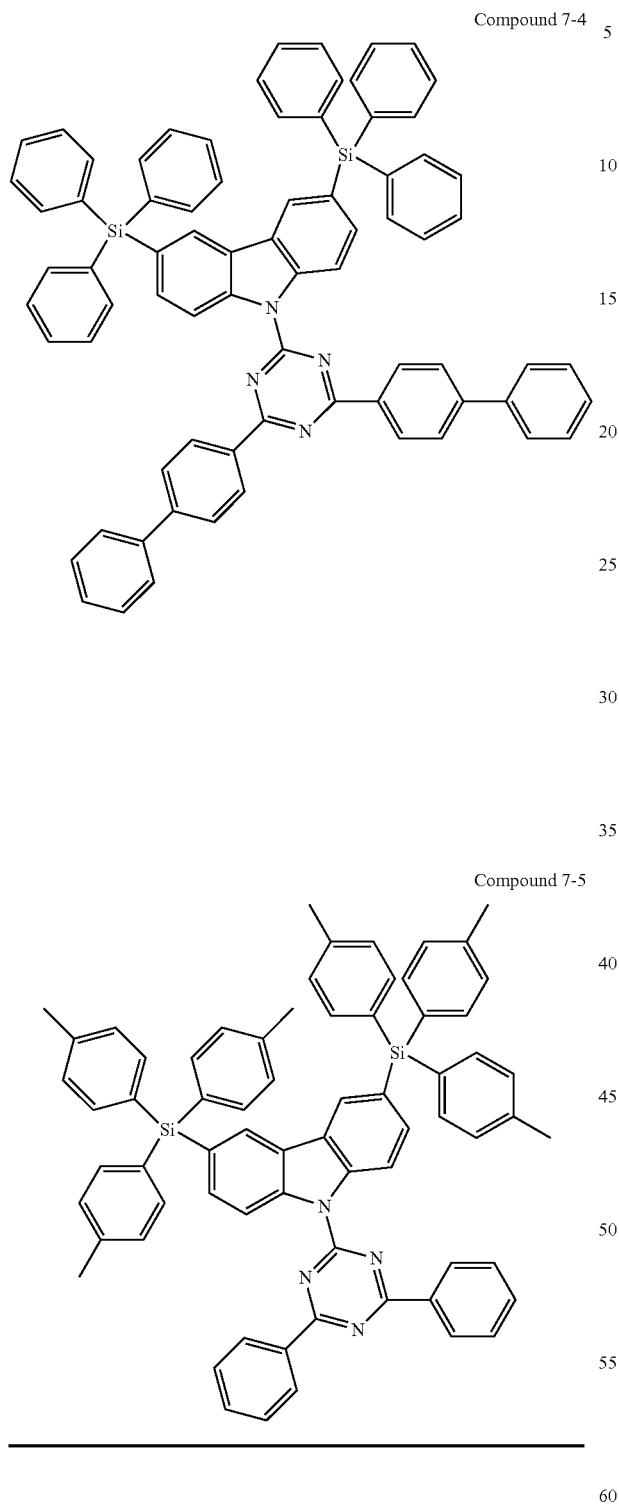

Compound 7-4

Compound 7-5

General formula (XI) corresponds to general formula (I) wherein X and Y each independently represent a triphenyl silyl group represented by formula (D), and may be linked at C-3 of the carbazole unit in the basic molecular skeleton of formula (I). Compounds 7-6 to 7-10 shown in Table 8 are represented by formula (XI), wherein m=1, n=0 and m+n=1.

TABLE 8

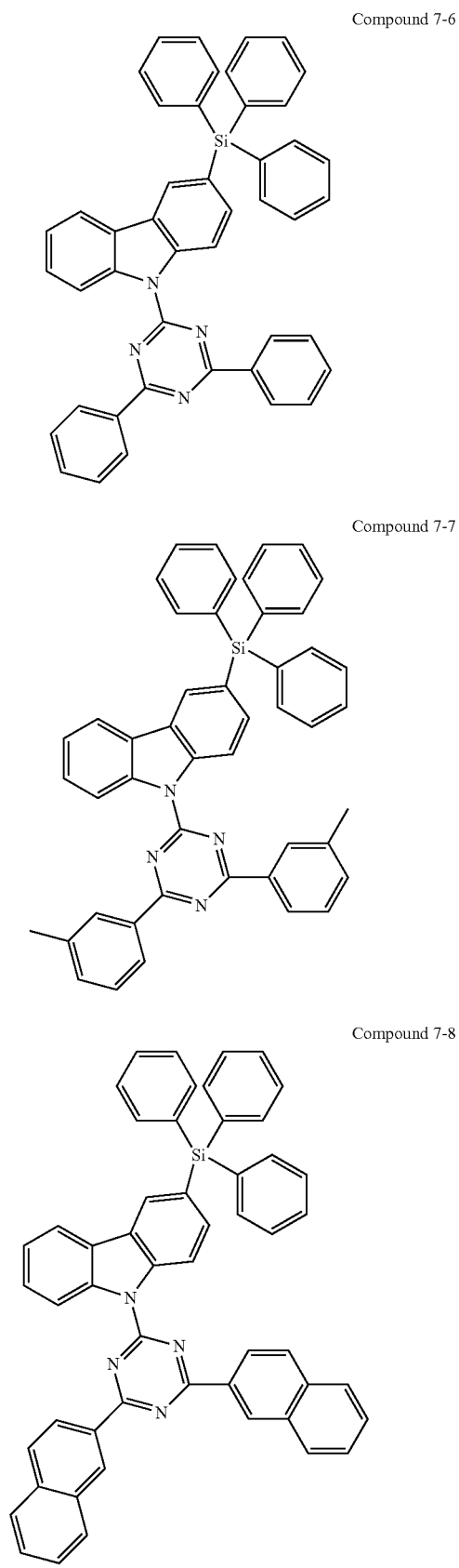

Compound 7-6

Compound 7-7

Compound 7-8

TABLE 8-continued

Compound 7-9

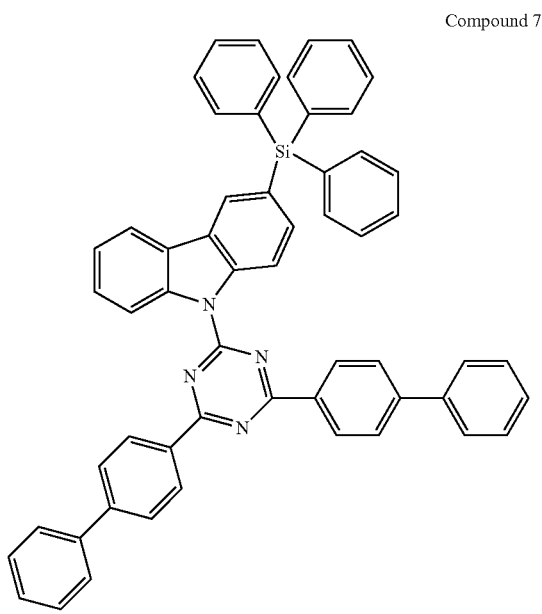

Compound 7-10

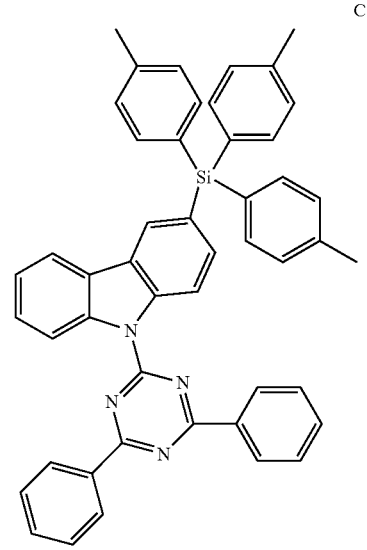

TABLE 9

Compound 8-1

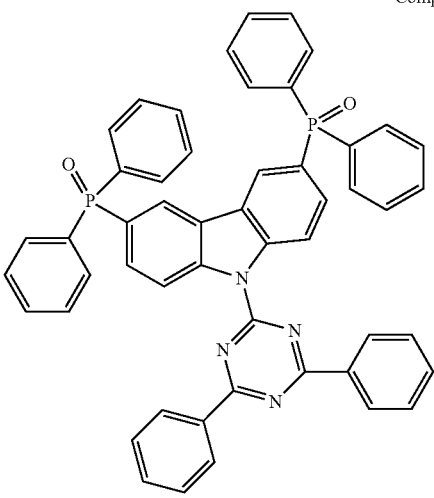

Compound 8-2

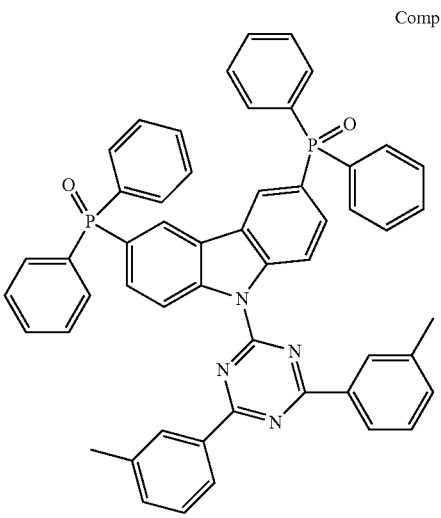

Compound 8-3

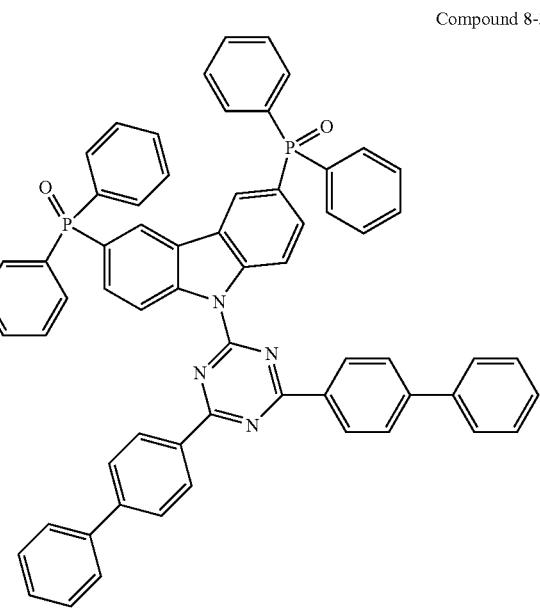

General formula (XII) corresponds to general formula (I) wherein X and Y each independently represent a diphenylphosphine oxide group represented by formula (E), and may be linked at C-3 and C-6 of the carbazole unit in the basic molecular skeleton of formula (I). Compounds 8-1 to 8-7 shown in Table 9 are represented by formula (XII), wherein m=1, n=1 and m+n=2.

TABLE 9-continued

Compound 8-4

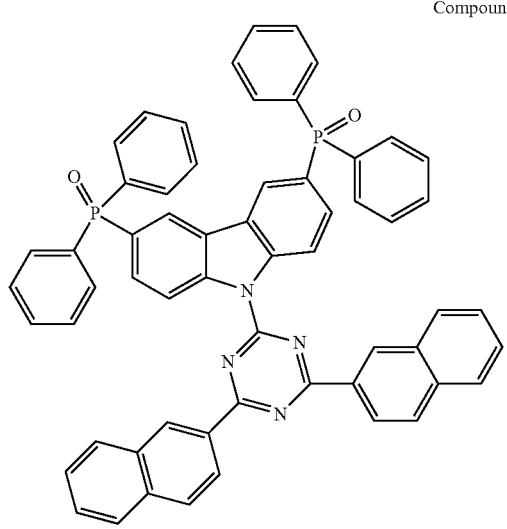

Compound 8-5

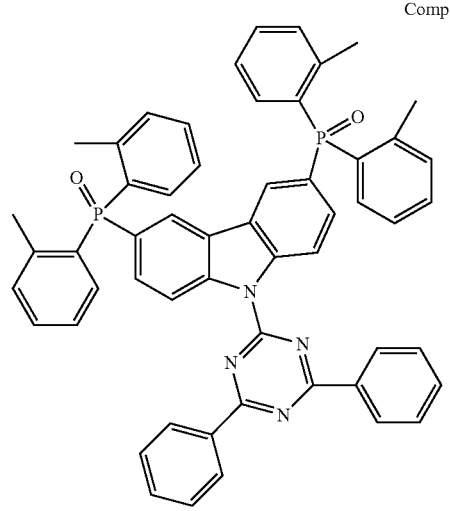

Compound 8-6

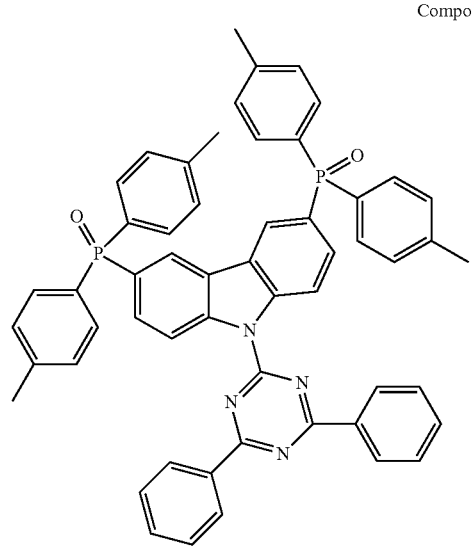

TABLE 9-continued

Compound 8-7

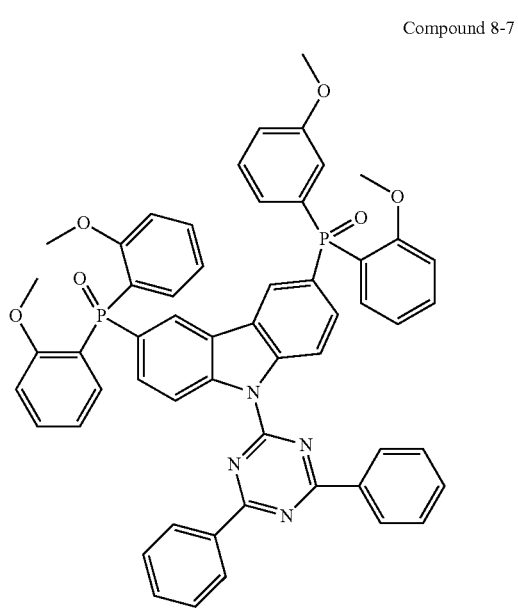

General formula (XIII) corresponds to general formula (I) wherein X and Y each independently represent a diphenylphosphine oxide group represented by formula (E), and may be linked at C-3 of the carbazole unit in the basic molecular skeleton of formula (I). Compounds 8-8 to 8-12 shown in Table 10 are represented by formula (XIII), wherein m=1, n=0 and m+n=1.

TABLE 10

Compound 8-8

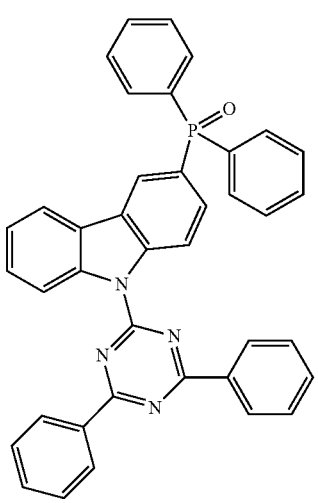 [SMILES: O=P(c1ccccc1)(c1ccccc1)c1ccc2c(c1)c1ccccc1n2-c1nc(-c2ccccc2)nc(-c2ccccc2)n1]

TABLE 10-continued
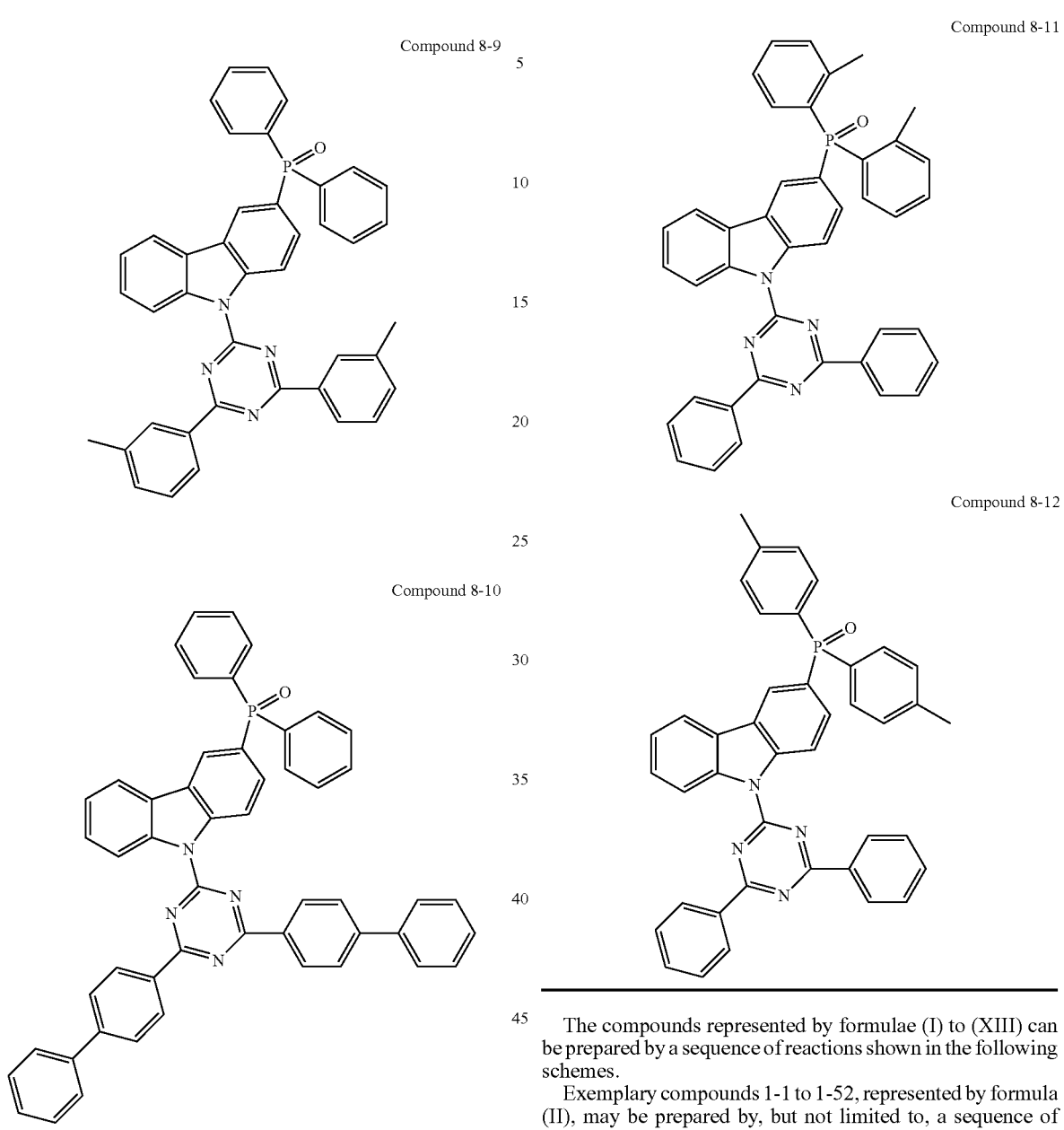
The compounds represented by formulae (I) to (XIII) can be prepared by a sequence of reactions shown in the following schemes.
Exemplary compounds 1-1 to 1-52, represented by formula (II), may be prepared by, but not limited to, a sequence of reactions shown in the scheme 1.
Scheme 1: Synthesis of compounds from 1-1-to 1-52
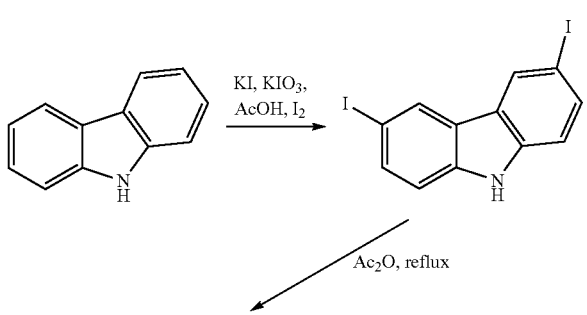

-continued
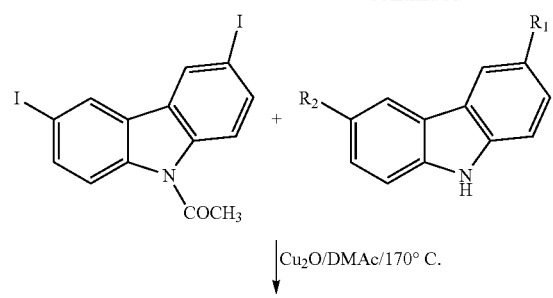
Cu₂O/DMAc/170° C.
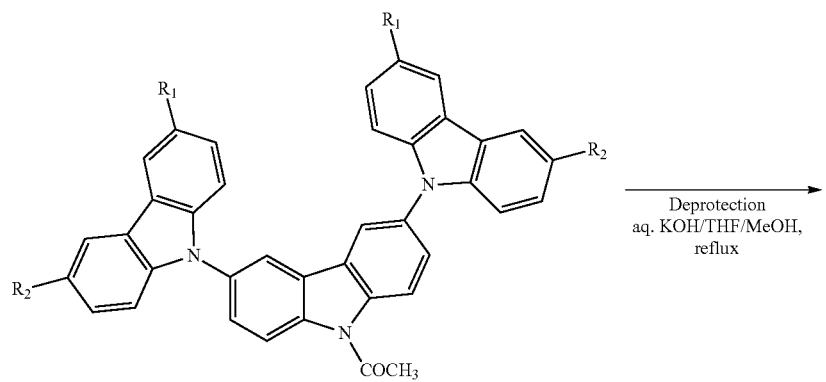
Deprotection
aq. KOH/THF/MeOH,
reflux
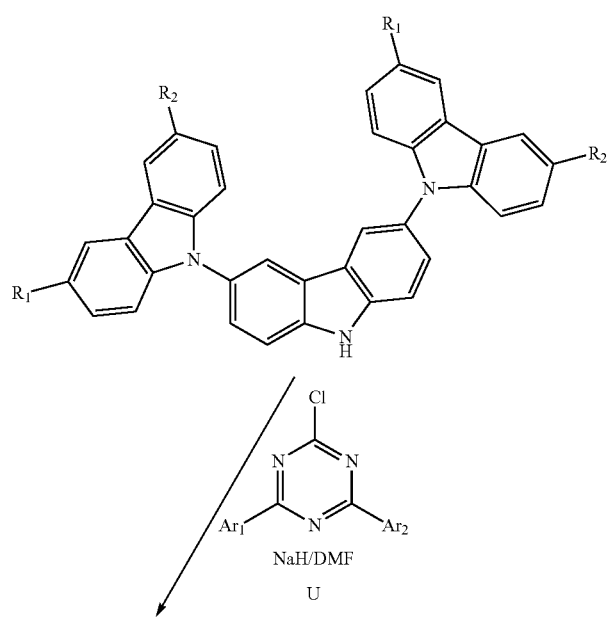
NaH/DMF
U

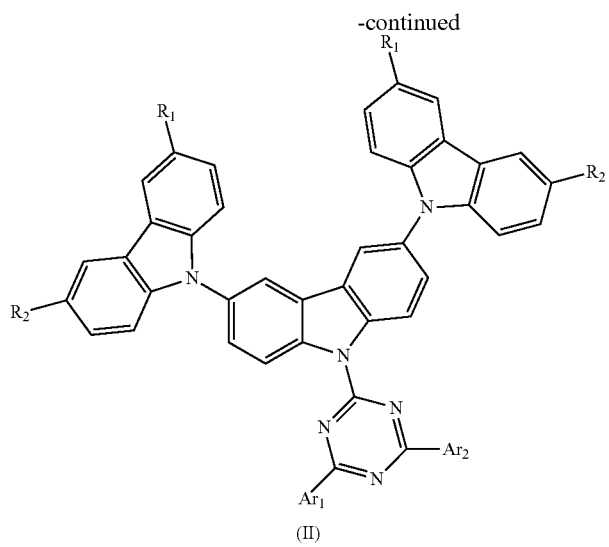
(II)
Exemplary compounds 2-1 to 2-10 represented by formula (III) may be prepared by, but not limited to, a sequence of reactions shown in the scheme 2.
Scheme 2: Synthesis of compounds from 2-1 to 2-10
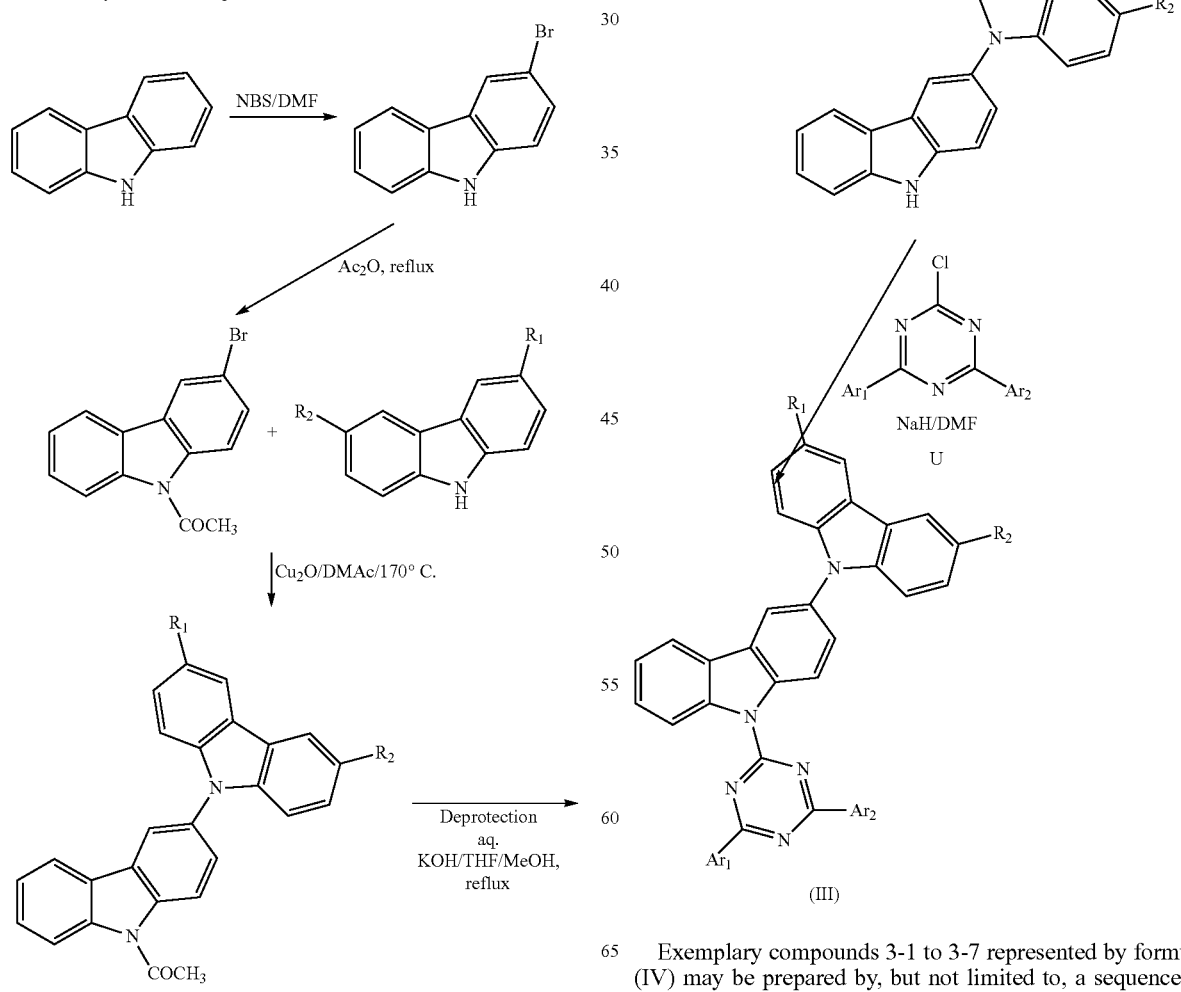
(III)
Exemplary compounds 3-1 to 3-7 represented by formula (IV) may be prepared by, but not limited to, a sequence of reactions shown in the scheme 3.

Scheme 3: Synthesis of compounds from 3-1 to 3-7
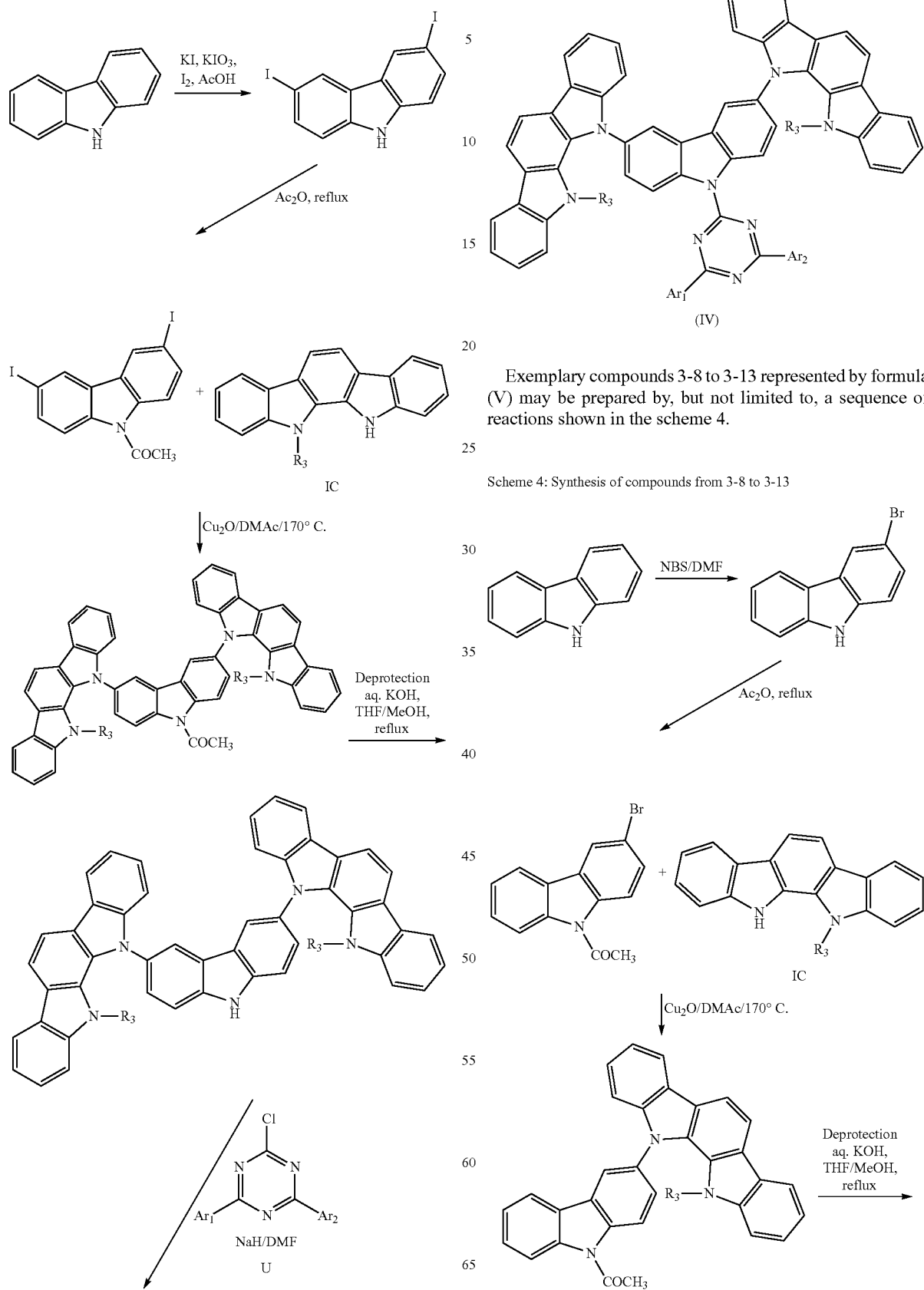
Exemplary compounds 3-8 to 3-13 represented by formula (V) may be prepared by, but not limited to, a sequence of reactions shown in the scheme 4.
Scheme 4: Synthesis of compounds from 3-8 to 3-13
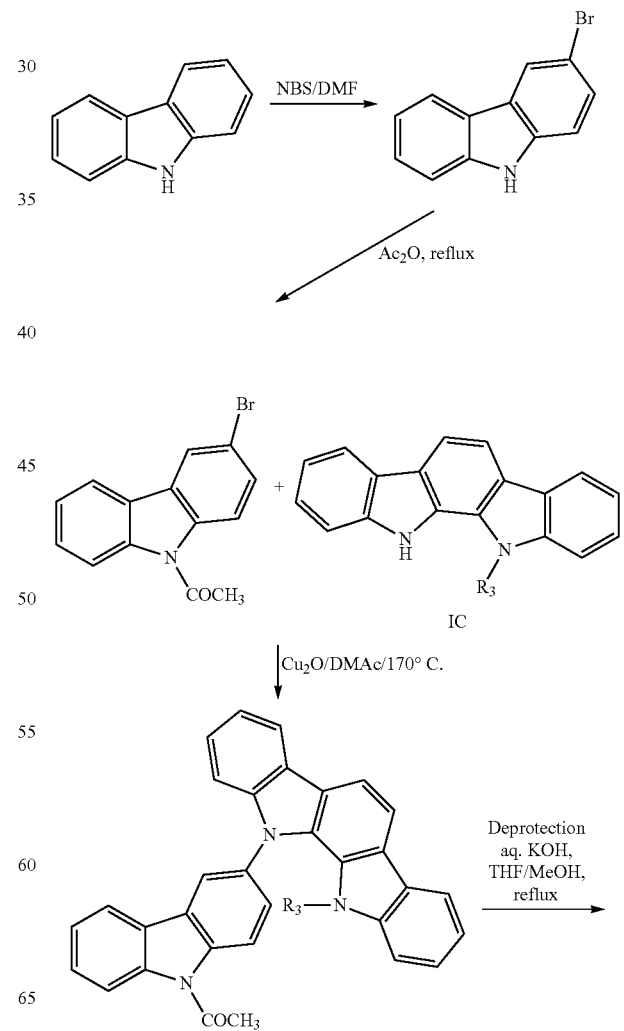

101
-continued
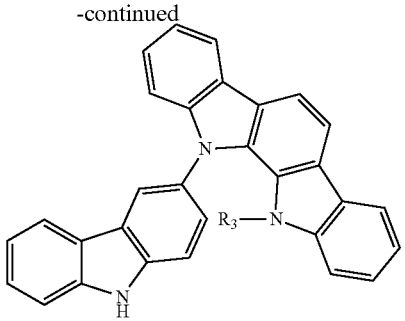
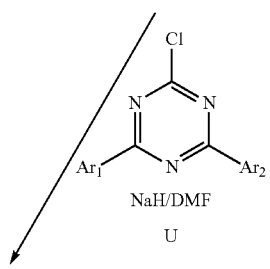
NaH/DMF
U
102
-continued
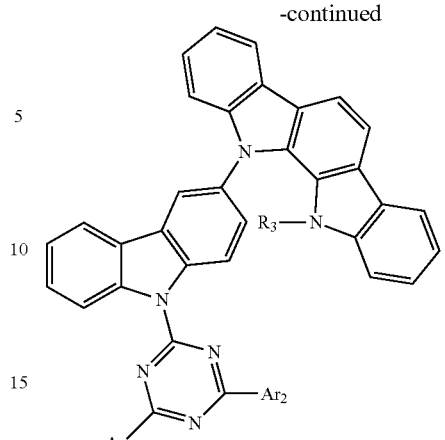
(V)
Exemplary compounds 4-1 to 4-5 represented by formula (VI) may be prepared by, but not limited to, a sequence of reactions shown in the scheme 5.
Scheme 5: Synthesis of compounds from 4-1 to 4-5
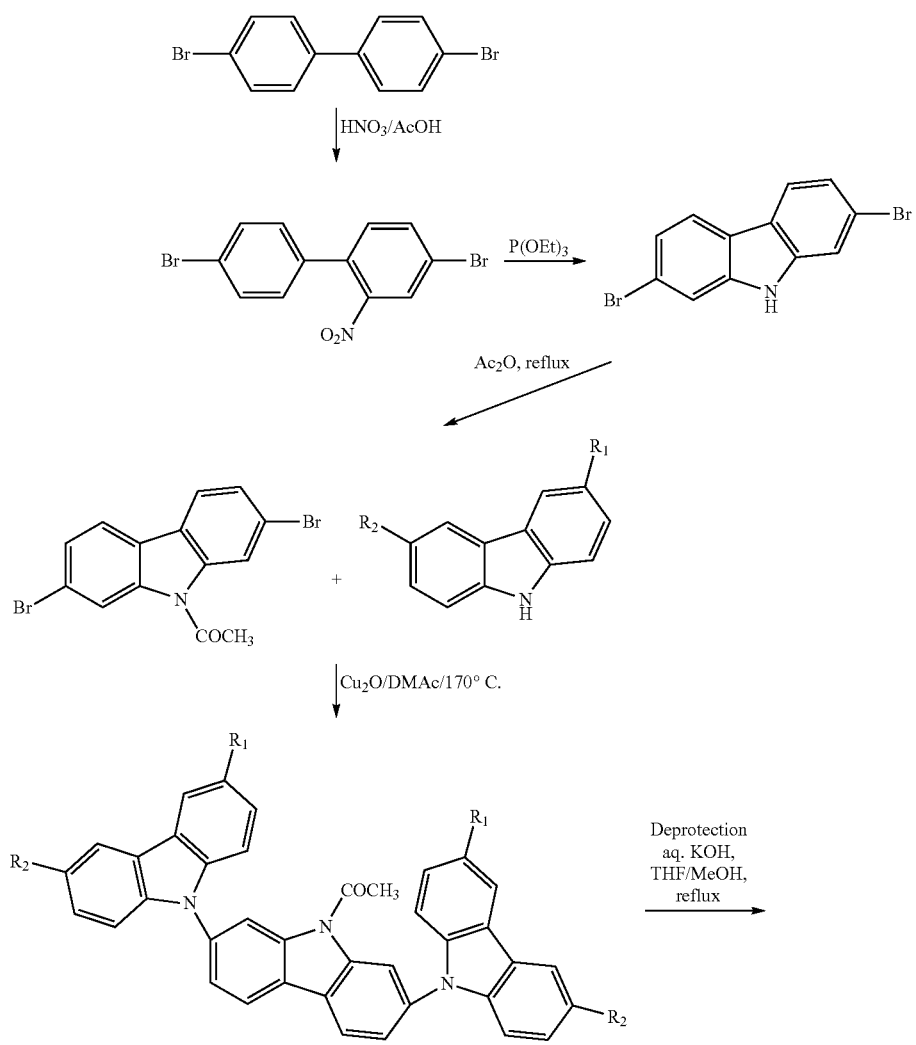

-continued
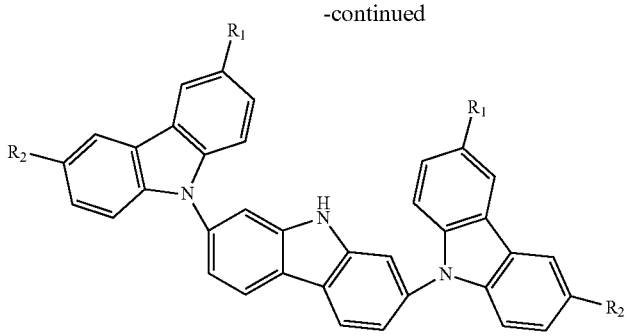
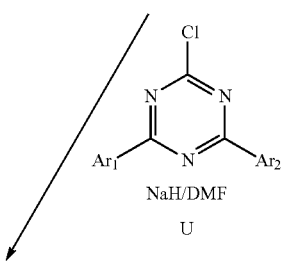
NaH/DMF
U
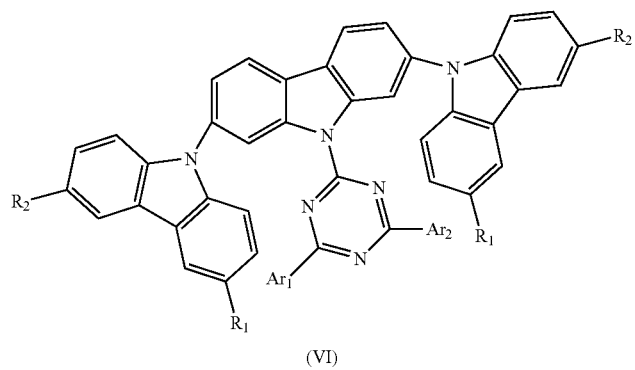
(VI)
Exemplary compounds 4-6 to 4-9 represented by formula (VII) may be prepared by, but not limited to, a sequence of reactions shown in the scheme 6.
Scheme 6: Synthesis of compounds from 4-6 to 4-9
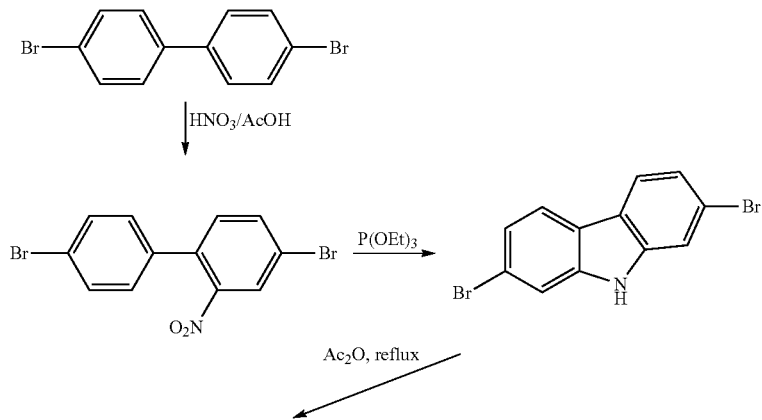

-continued
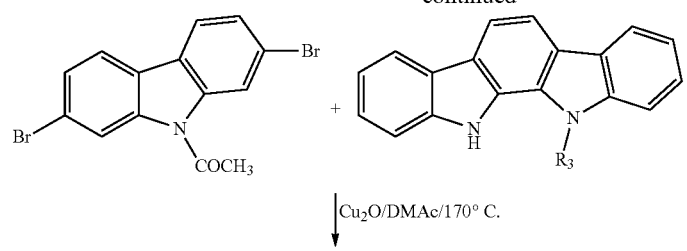
Cu₂O/DMAc/170° C.
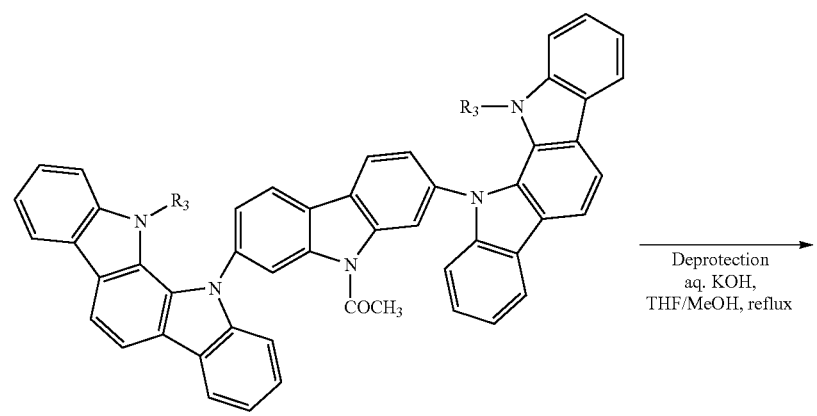
Deprotection
aq. KOH,
THF/MeOH, reflux
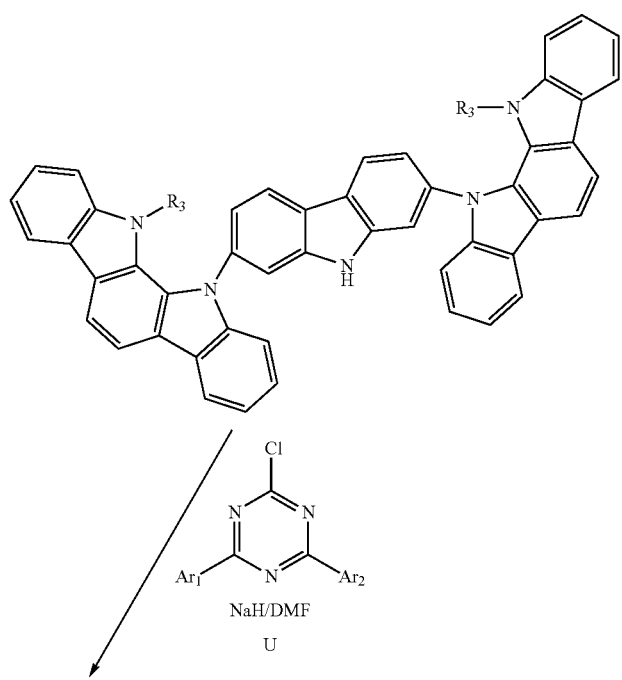
NaH/DMF
U

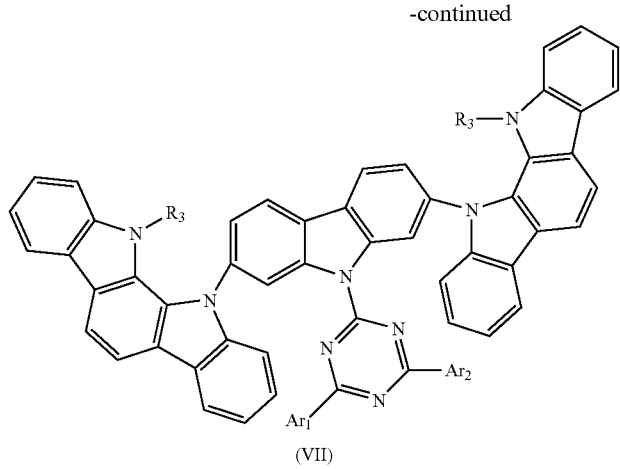
(VII)
Exemplary compounds 5-1 to 5-10 represented by formula (VIII) may be prepared by, but not limited to, a sequence of reactions shown in the scheme 7.
Scheme 7: Synthesis of compounds from 5-1 to 5-10
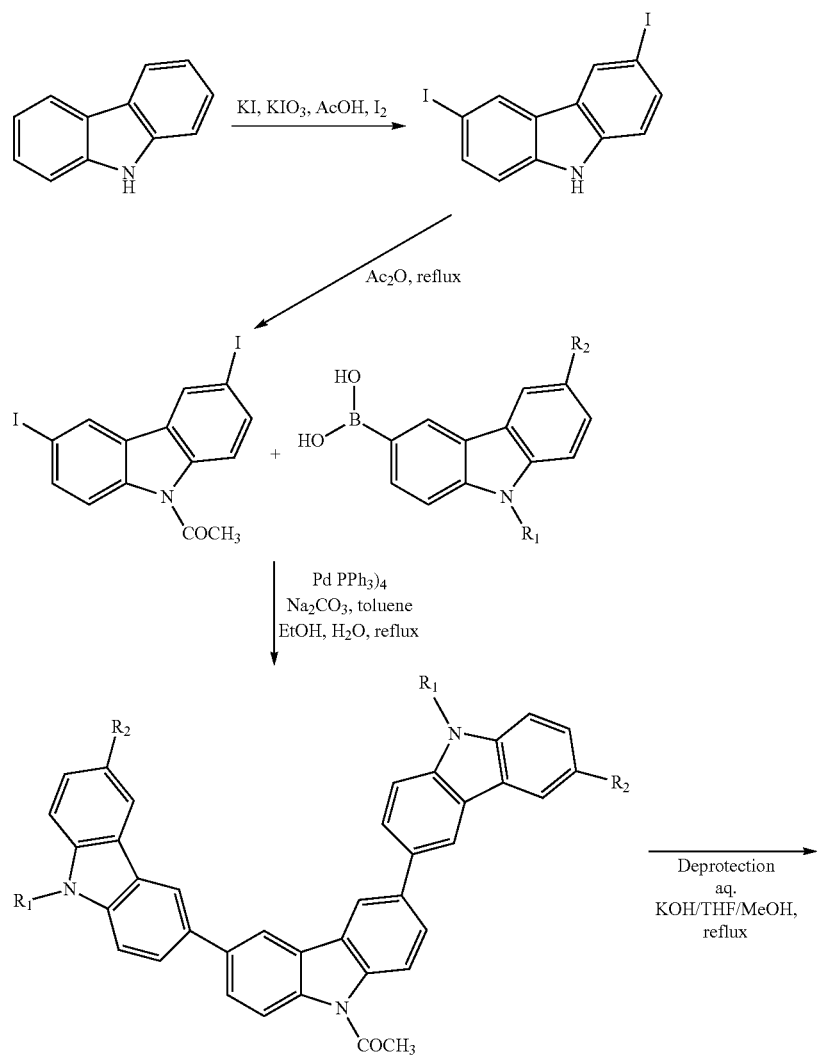

-continued
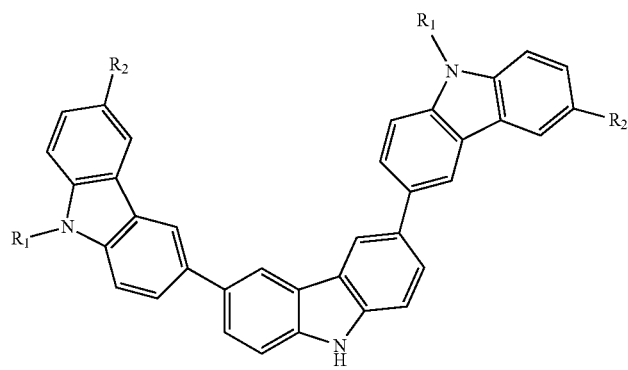
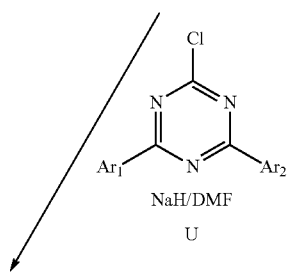
NaH/DMF
U
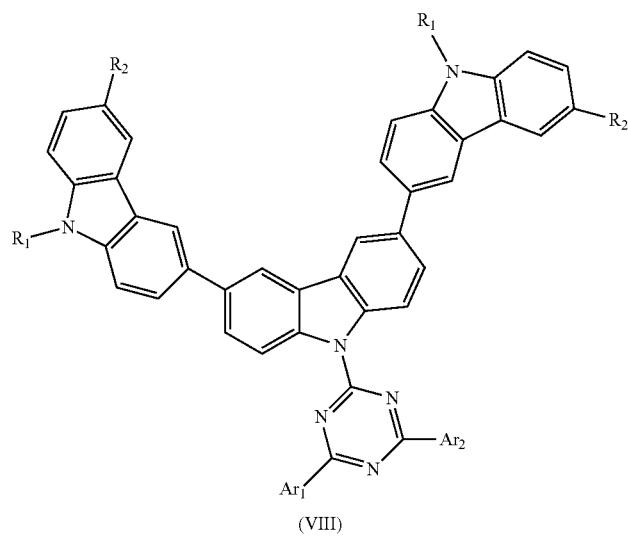
(VIII)

Exemplary compounds 6-1 to 6-6 represented by formula (IX) may be prepared by, but not limited to, a sequence of reactions shown in the scheme 8.
Scheme 8: Synthesis of compounds from 6-1 to 6-6
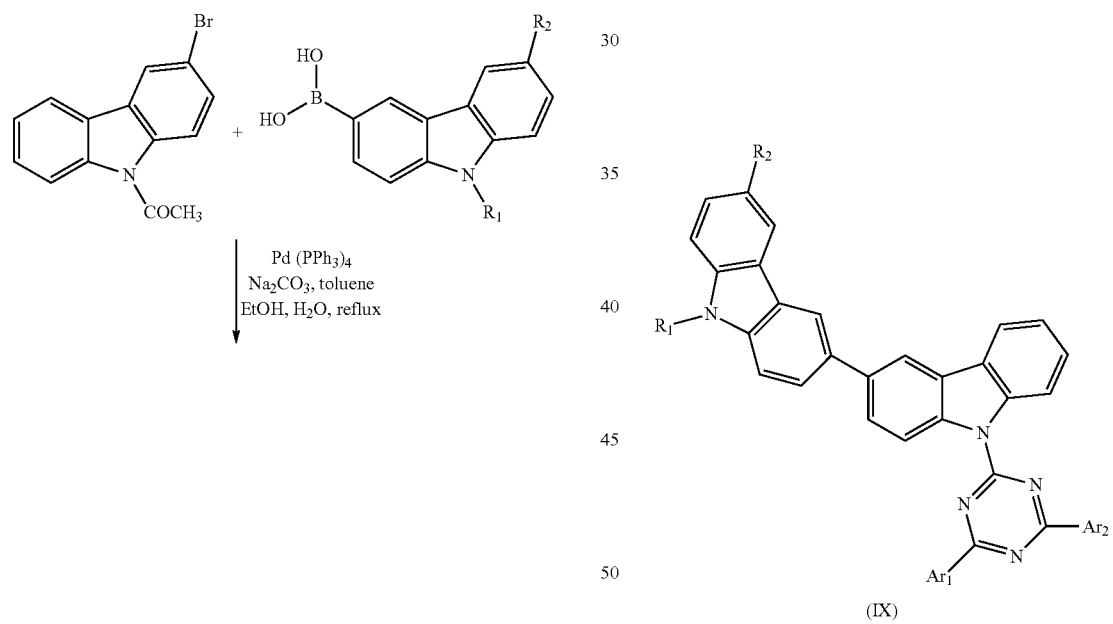
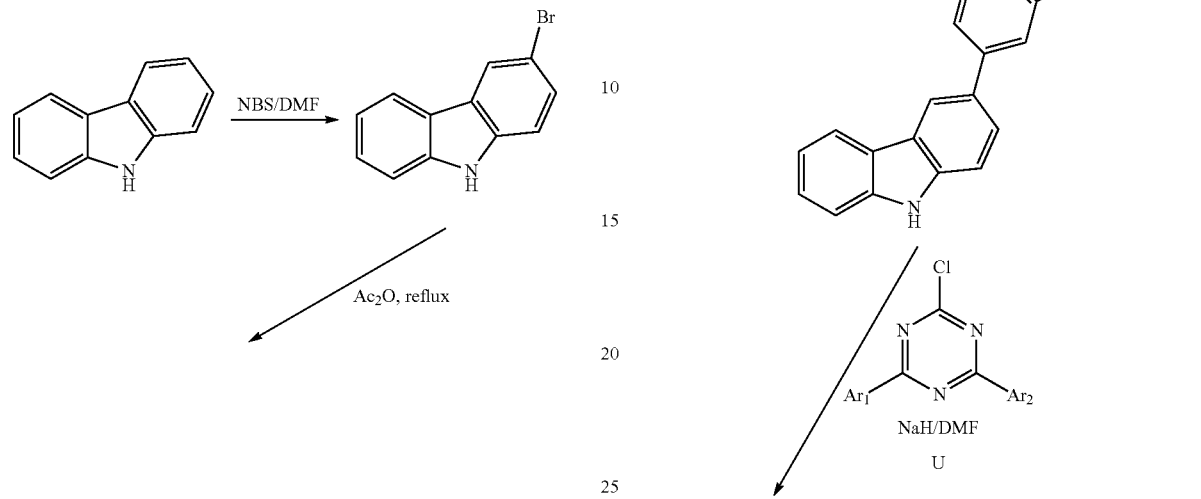
(IX)
Exemplary compounds 7-1 to 7-5 represented by formula (X) may be prepared by, but not limited to, a sequence of reactions shown in the scheme 9.
Scheme 9: Synthesis of compounds from 7-1 to 7-5

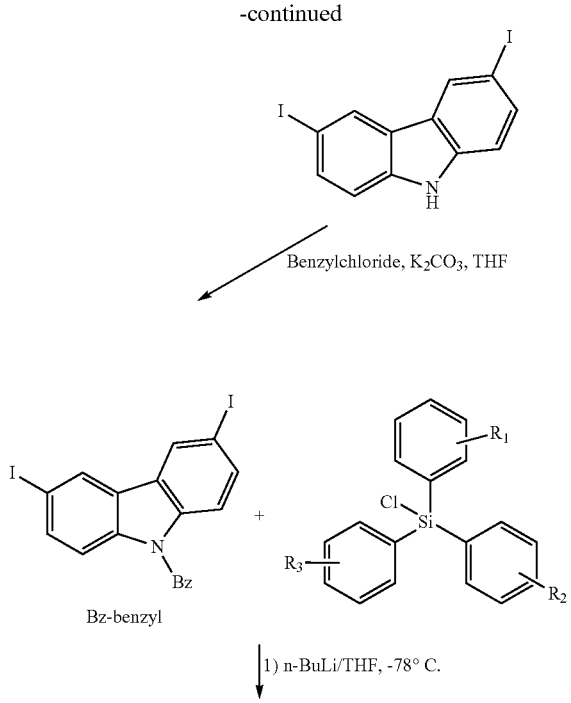
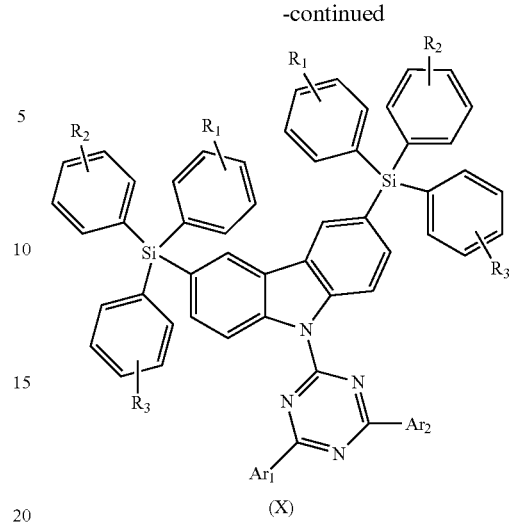
Exemplary compounds 7-6 to 7-10 represented by formula (XI) may be prepared by, but not limited to, a sequence of reactions shown in the scheme 10.
Scheme 10: Synthesis of compounds from 7-6 to 7-10
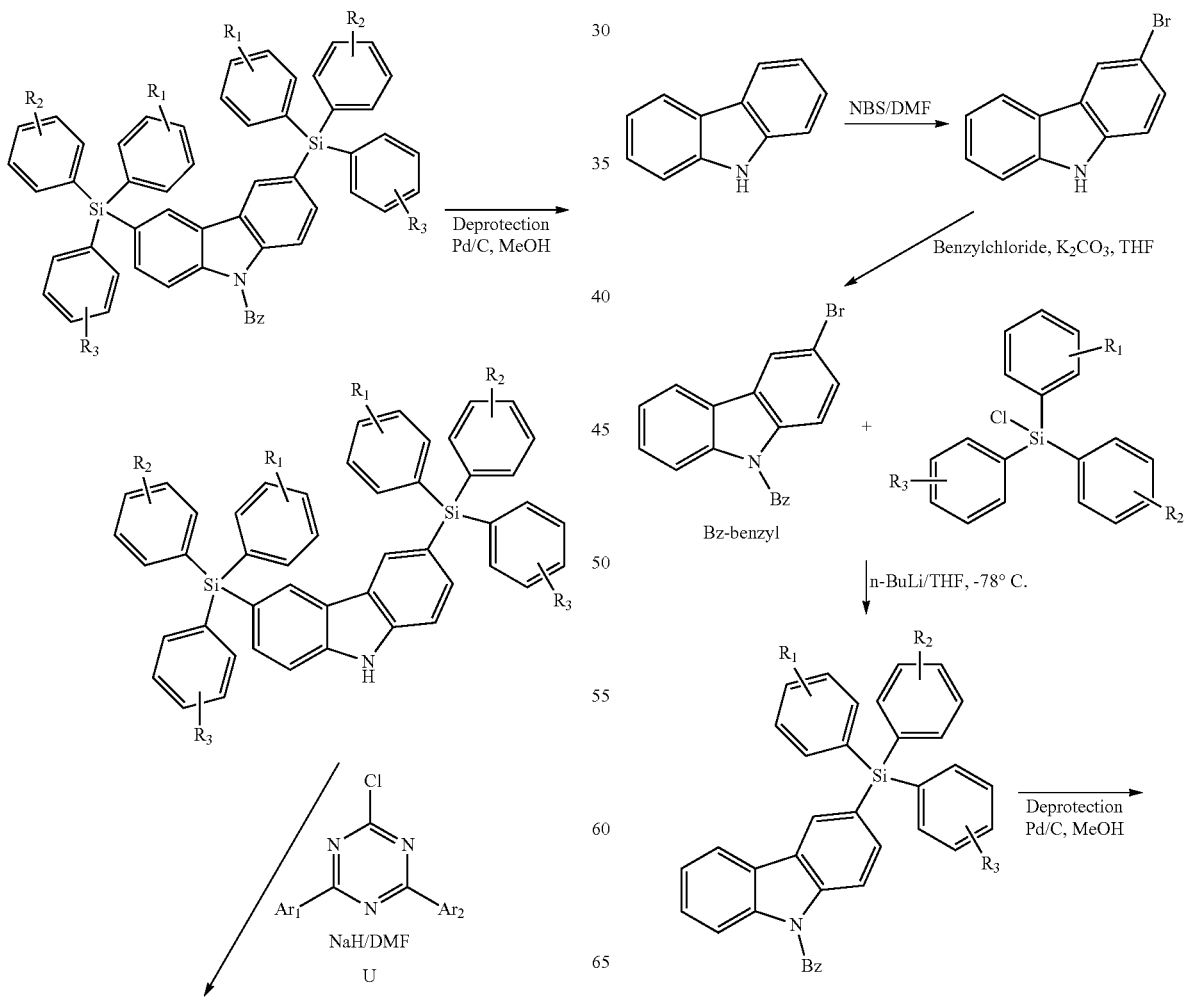

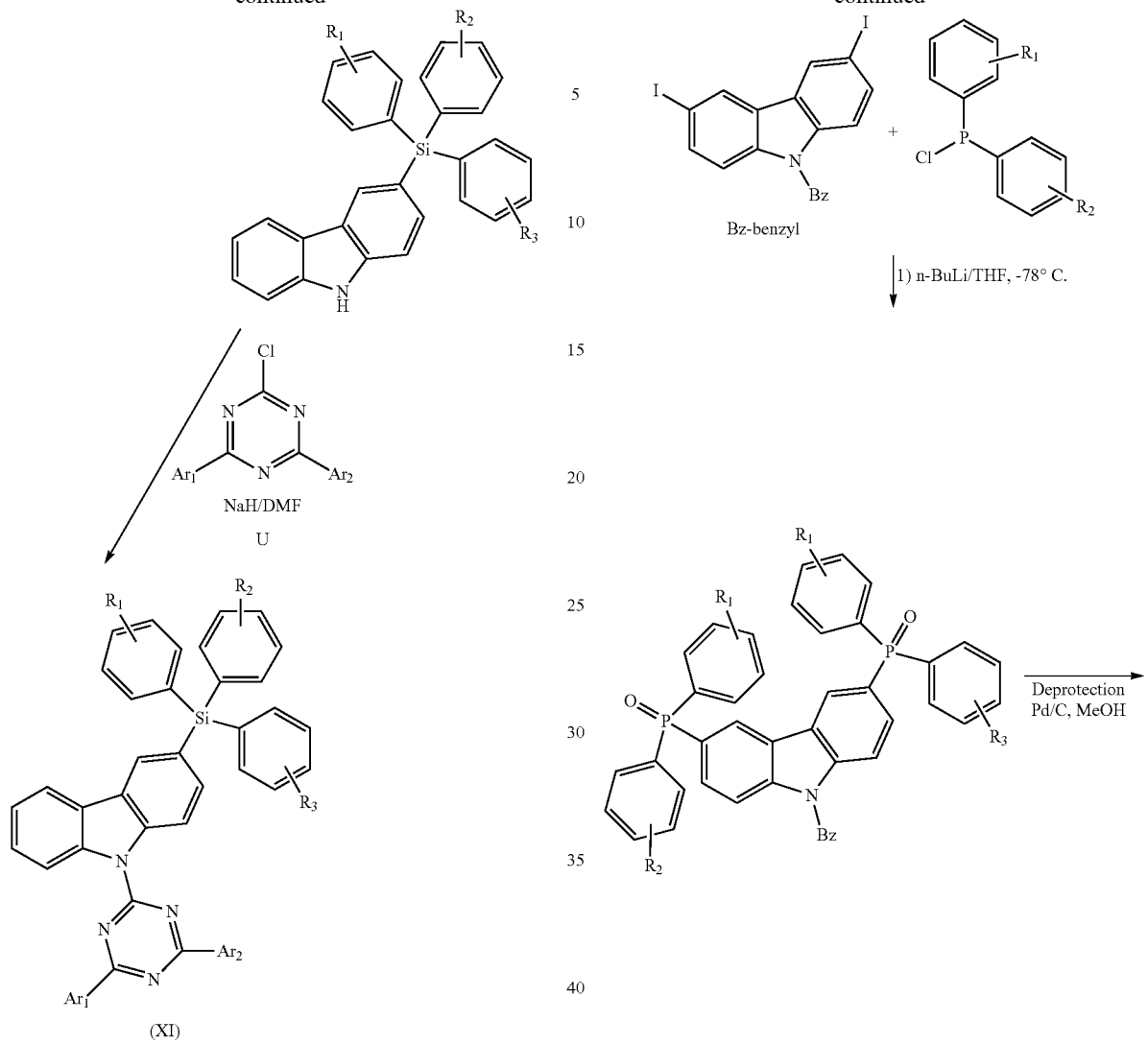
Exemplary compounds 8-1 to 8-7 represented by formula (XII) may be prepared by, but not limited to, a sequence of reactions shown in the scheme 11.
Scheme 11: Synthesis of compounds from 8-1 to 8-7
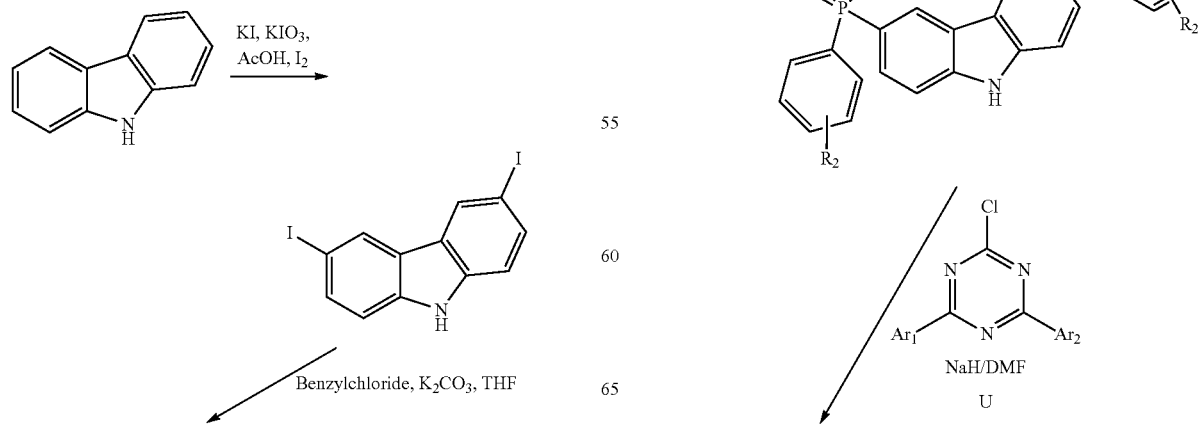

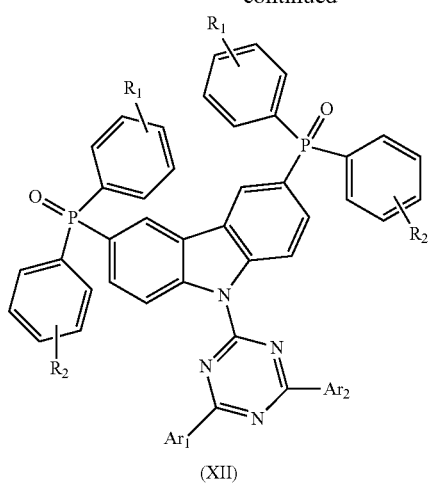

(XII)

Exemplary compounds 8-8 to 8-12 represented by formula (XIII) may be prepared by, but not limited to, a sequence of reactions shown in the scheme 12.

Scheme 12: Synthesis of compounds from 8-8 to 8-12

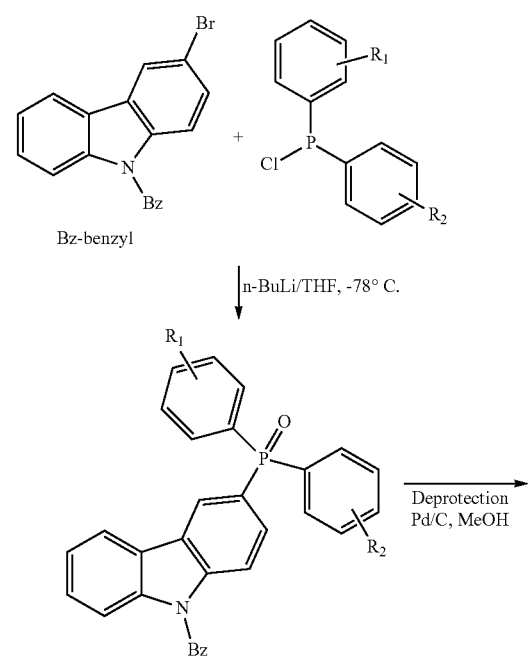

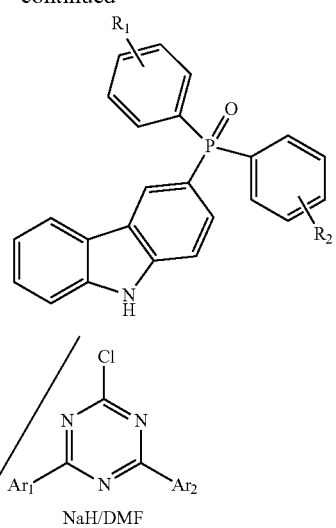

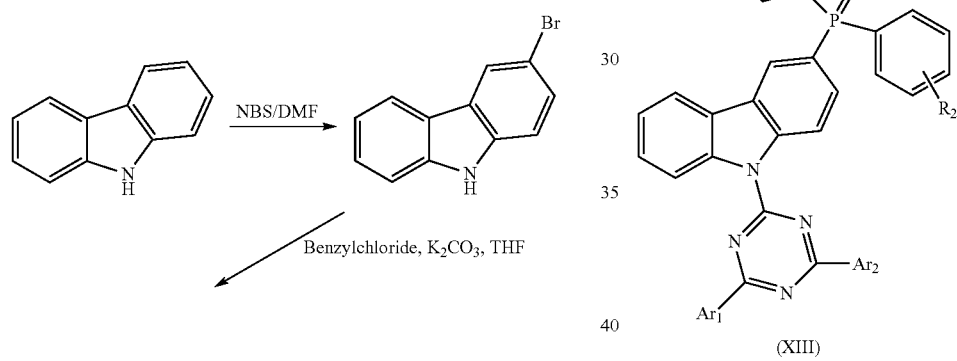

(XIII)

Specific examples of 2-chloro-4,6-diaryltriazines (U) used in the preparation of the above-mentioned compounds of formulae (I) to (XIII) are shown in, but not limited to, Table 11.

TABLE 11

| Example | Ar$_1$ | Ar$_2$ |
|---|---|---|
| U-1 | phenyl | phenyl |
| U-2 | 3-methylphenyl | 3-methylphenyl |

TABLE 11-continued

| Example | Ar₁ | Ar₂ |
|---|---|---|
| U-3 | 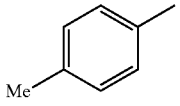 | 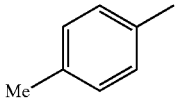 |
| U-4 | 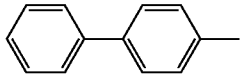 | 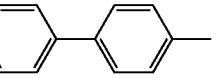 |
| U-5 | 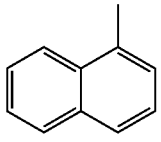 | 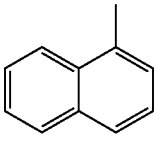 |
| U-6 | 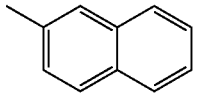 | 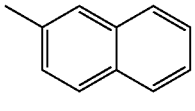 |
| U-7 | 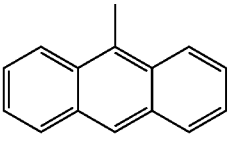 | 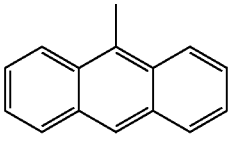 |
| U-8 | 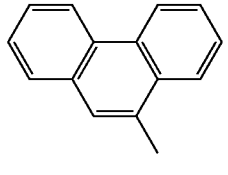 | 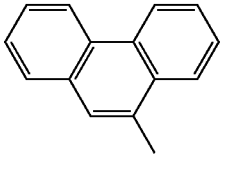 |
| U-9 | 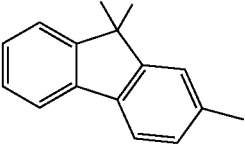 | 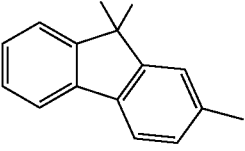 |

The aforementioned examples U-1 to U-9 can be readily prepared by known methods described in J. Org. Chem., 1969, No. 34, p. 4125; Chem. Ztg, 1912, No. 36, p. 738.

Specific examples of N-substituted-indolo[2,3-a]carbazoles (IC) used in the preparation of the above-mentioned compounds of formulae (I) to (XIII) are shown in, but not limited to, Table 12. Compounds IC-1 to IC-5 may be prepared by the well-known Hartwig-Buchwald amination using bis(dibenzylideneacetone)palladium in presence of sodium tert-butoxide and tri-tert-butylphosphine, described elsewhere. In the conventional procedures, compounds IC-6 and IC-8 may be prepared by alkylation with corresponding alkyl halides in presence of a base such as KOH.

TABLE 12

| Example | R₃ |
|---|---|
| IC-1 | 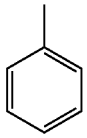 |
| IC-2 | 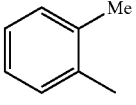 |
| IC-3 | 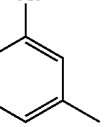 |
| IC-4 | 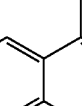 |
| IC-5 | 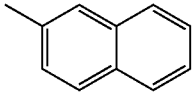 |
| IC-6 | ethyl |
| IC-7 | 2-ethylhexyl |
| IC-8 | isobutyl |

Various substituted derivatives of carbazole intermediates shown in the above schemes that are used in the synthesis of the compounds of formulae (I) to (XIII) in the present invention may be prepared by other conventional procedures.

The organic electroluminescent device of this invention has at least one light emitting layer disposed between an anode and a cathode piled one upon another on a substrate, and the light emitting layer includes a phosphorescent dopant and the aforementioned compound represented by any one of formulae (I) to (XIII) as a host material. It is preferable that a hole injecting/transporting layer is formed between the anode and the light emitting layer and an electron injecting/transporting layer is formed between the cathode and the light emitting layer. It is also preferable that either a hole blocking layer is formed between the light emitting layer and the electron injecting/transporting layer or an electron blocking layer is formed between the hole injecting/transporting layer and the light emitting layer.

Further, the compounds represented by any of formulae (I) to (XIII) may be used in the electron injecting/transporting layer or hole blocking layer and/or electron blocking layer.

Phosphorescent dopants to be used in the light emitting layer are preferably organic metal complexes containing at least one metal selected from ruthenium, rhodium, palladium, silver, rhenium, osmium, iridium, platinum, and gold. Such organic metal complexes are known in the aforementioned patent documents and elsewhere and a suitable complex can be selected from them and used in this invention.

Preferable phosphorescent dopants include complexes having a noble metal element such as Ir in the center, typically Ir(ppy)₃, complexes such as Ir(bt)₂(acac), FIrpic, and complexes such as PtOEt₃, but are not limited thereto.

The content of the aforementioned phosphorescent dopant in the light emitting layer is preferably in the range of 3 wt % to 10 wt % based on the total weight of the light emitting layer.

Preferred Embodiments of the Invention

The structure of the organic electroluminescent device of this invention will be explained with reference to the drawing, but not limited thereto.

FIG. 1 is a schematic view showing an organic light emitting device according to an embodiment of the present invention. An organic light emitting device 100 includes a substrate 110, an anode 120, a hole injection layer 130, a hole transport layer 140, an emissive layer 150, an electron transport layer 160, an electron injection layer 170, and a cathode 180. The organic light emitting device 100 may be fabricated by depositing the layers described in order.

Figure 2:
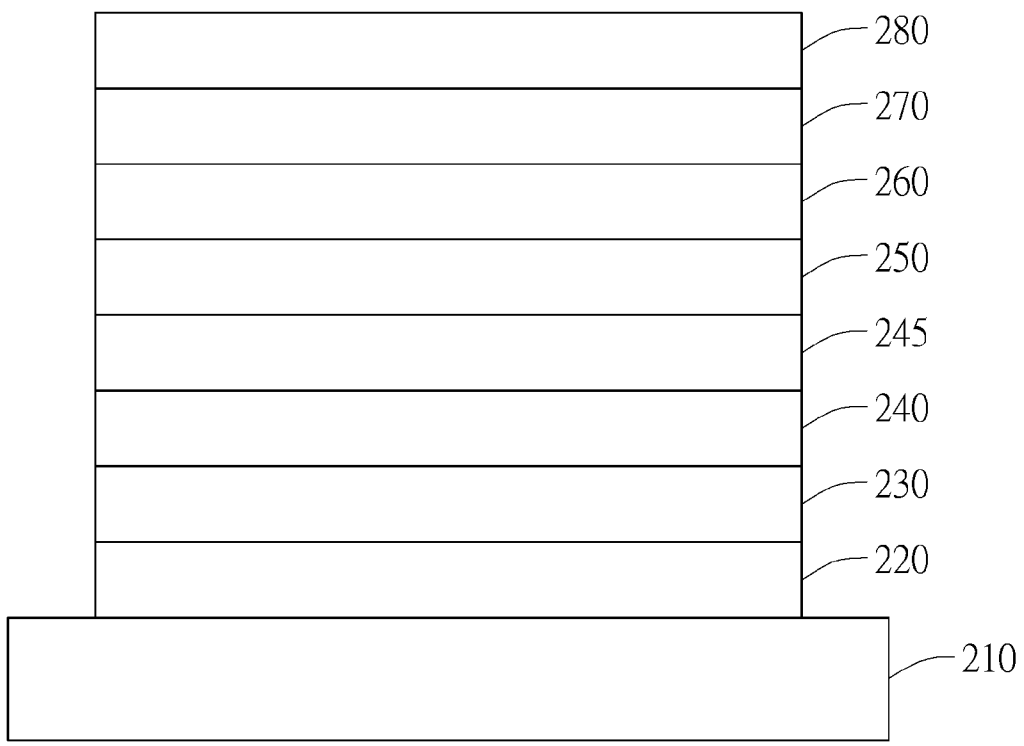
FIG. 2 is a cross-sectional view illustrating an organic light emitting device according to another embodiment of the present invention.

FIG. 2 is a schematic view showing an organic light emitting device according to another embodiment of the present invention. An organic light emitting device 200 includes a substrate 210, an anode 220, a hole injection layer 230, a hole transport layer 240, an exciton blocking layer 245, a light emitting layer 250, an electron transport layer 260, an electron injection layer 270, and a cathode 280.

Figure 3:
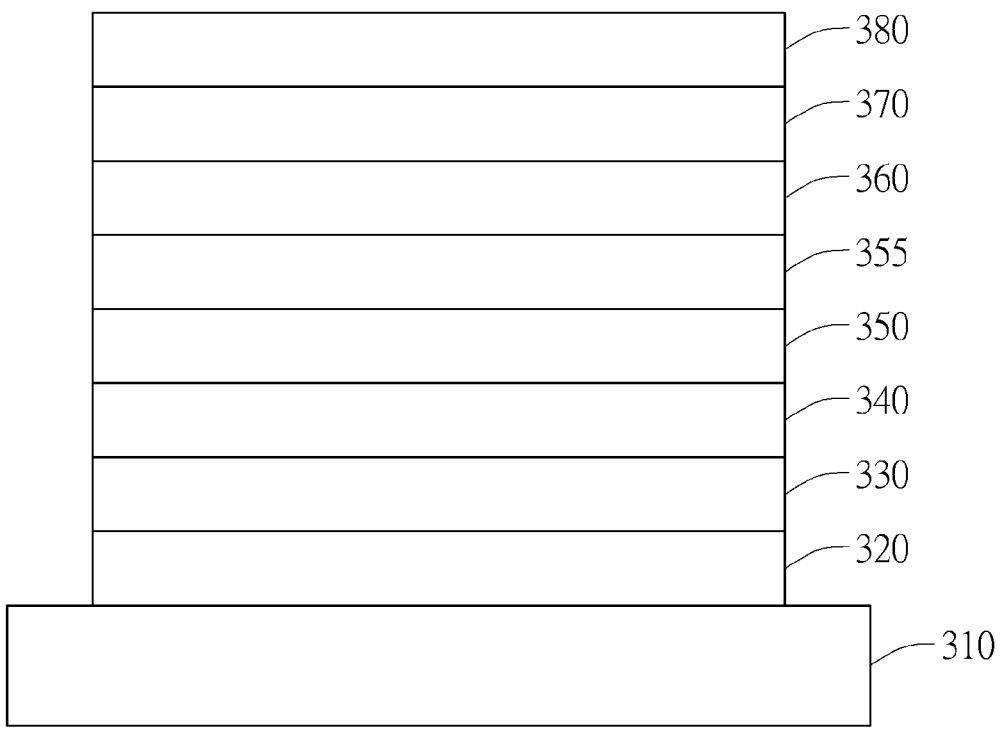
FIG. 3 is a cross-sectional view illustrating an organic light emitting device according to another embodiment of the present invention.

FIG. 3 is a schematic view showing an organic light emitting device according to another embodiment of the present invention. An organic light emitting device 300 includes a substrate 310, an anode 320, a hole injection layer 330, a hole transport layer 340, a light emitting layer 350, an exciton blocking layer 355, an electron transport layer 360, an electron injection layer 370, and a cathode 380.

It is possible to fabricate an organic light emitting device with a structure that is the reverse of the one shown in FIGS. 1-3. In this case of the reverse structure, a layer or layers may be added or omitted as needed.

Materials used in hole injection layer, hole transport layer, electron blocking layer, hole blocking layer, electron transport layer, electron injection layer may be selected from those reported in the literature cited elsewhere.

For example, an electron-transporting material forming the electron-transporting layer differs from the material forming the light emitting layer and has hole-transporting properties, so as to facilitate the hole mobility in the electron-transporting layer, and to prevent accumulation due to the difference in ionization potential between the light emitting layer and the electron-transporting layer can be prevented.

In addition, U.S. Pat. No. 5,844,363, which is incorporated by reference in its entirety, discloses a flexible and transparent substrate-anode combination. An example of a p-doped hole transport layer is m-MTDATA doped with $F_4$-TCNQ at a molar ratio of 50:1, as disclosed in US Patent Application Publication No. 20030230980, which is incorporated by reference in its entirety. An example of an n-doped electron transport layer is BPhen doped with Li at a molar ratio of 1:1, as disclosed in US Patent Application Publication No. 20030230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in U.S. Pat. No. 6,097,147 and US Patent Application Publication No. 20030230980, which are incorporated by reference in their entireties. Examples of injection layers are provided in US Patent Application Publication No. 20040174116, which is incorporated by reference in its entirety. A description of protective layers may be found in US Patent Application Publication No. 20040174116, which is incorporated by reference in its entirety.

Structures and materials not specifically described may also be used, such as OLEDs comprised of polymeric materials (PLEDs) such as disclosed in U.S. Pat. No. 5,247,190, which is incorporated by reference in its entirety. Further, OLEDs having a single organic layer may be used. OLEDs may be stacked as described in U.S. Pat. No. 5,707,745, which is incorporated by reference in its entirety.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102, which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with deposition methods such as ink-jet and OVJD. Certainly, other methods may be used. The materials to be deposited may be modified to make them compatible with a particular deposition method.

An organic electroluminescent device of this invention is applicable to a single device, a device with its structure arranged in array, or a device having the anode and the cathode arranged in an X-Y matrix. The present invention significantly improves luminous efficiency and driving stability of an organic electroluminescent device over the conventional devices, when used in combination of phosphorescent dopants in the light emitting layer, and furthermore the organic electroluminescent device of the present invention can perform better when applied to full-color or multicolor panels.

EXAMPLES

This invention will be described in more detail below with reference to the examples; however, it will not be limited to these examples and it can be reduced to practice in various modes unless such practice exceeds the substance of this invention.

3,6-diiodocarbazole and
9-acetyl-3,6-diiodocarbazole 3,6-diiodocarbazole and its 9-acetyl-3,6-diiodocarbazole were synthesized according to the procedure described in J. Chem. Soc. 1926, p. 546.

3-bromocarbazole and 9-acetyl-3-bromocarbazole 16 g of carbazole was dissolved in 80 ml of N,N'-dimethylformamide. To this was added 18 g of N-bromosuccinimide and allowed the reaction to stir at room temperature overnight. The reaction mixture was poured into water and the precipitated white solid was filtered, washed with methanol and dried under vacuum to obtain 20 g of 3-bromocarbazole.

It was further converted to its acetyl derivative by refluxing with acetic anhydride (3 vol) with traces of conc. sulfuric acid. Aqueous workup yielded an off-white solid, which was then washed with n-hexane and dried under vacuum to obtain 23 g 9-acetyl-3-bromocarbazole, quantitatively.

2,7-dibromocarbazole and
9-acetyl-2,7-dibromocarbazole 2,7-dibromocarbazole was prepared from 4,4'-dibromobiphenyl according to the procedure described in Macromol. Rapid commun. 2007, No. 28, p. 334.

It was further converted to its acetyl derivative by refluxing with acetic anhydride (3 vol) with traces of conc. sulfuric acid. Aqueous workup yielded a white solid, which was then washed with n-hexane and dried under vacuum to obtain 9-acetyl-2,7-dibromocarbazole.

9-benzyl-3-bromocarbazole 24 g of 3-bromocarbazole was dissolved in 100 ml of tetrahydrofuran. To this was added 14 g of potassium carbonate followed by 14 g of benzylchloride and allowed the reaction to stir at room temperature overnight. The reaction mixture was poured into water and the precipitated white solid was filtered, washed with methanol and dried under vacuum to obtain 30 g 9-benzyl-3-bromocarbazole (89%).

Synthesis Example 1

Synthesis of Compound 1-1

A mixture of 2.0 g of 9-acetyl-3,6-diiodocarbazole and 1.1 g of carbazole were stirred together in 20 ml N,N'-dimethylacetamide. To this was added 0.8 g of copper oxide and heated to 170° C. for 24 h. The reaction was quenched with water and the solid was filtered, washed with methanol, and dried under vacuum. The solid (3 g) was then taken up for further deprotection using 0.6 g KOH with THF (3 ml), methanol (6 ml) and water (6 ml) at reflux temperature. The reaction mixture was then extracted using ethyl acetate; and the organic layer was dried over anhydrous sodium sulfate and evaporated to dryness under vacuum. Subsequent silica gel column chromatography using toluene:hexane (1:2) as eluent, yielded 1.5 g of 3,6-dicarbazolylcarbazole.

The above obtained 3,6-di(9-carbazolyl)carbazole (1.5 g) was dissolved in 30 ml of dry N,N'-dimethylformamide under nitrogen. 0.15 g of sodium hydride was added and stirred at room temperature for 1 h. A solution of 2-chloro-4,6-diphenyl-1,3,5-triazine (U-1, 1.0 g) in dry N,N'-dimethylformamide (10 ml) was then added to the reaction mixture. The reaction was further allowed to stir for 3 h. The product was precipitated by pouring the reaction mixture into water. The solid thus obtained was then washed with methanol and dried under vacuum to obtain 1.6 g of 2,4-diphenyl-6-(3,6-di(9-carbazolyl)carbazole-9'-yl)-1,3,5-triazine, compound 1-1 (73%).

Compound 1-1 showed a melting point of 382° C. and a glass transition temperature of 193° C.

Figure 4:
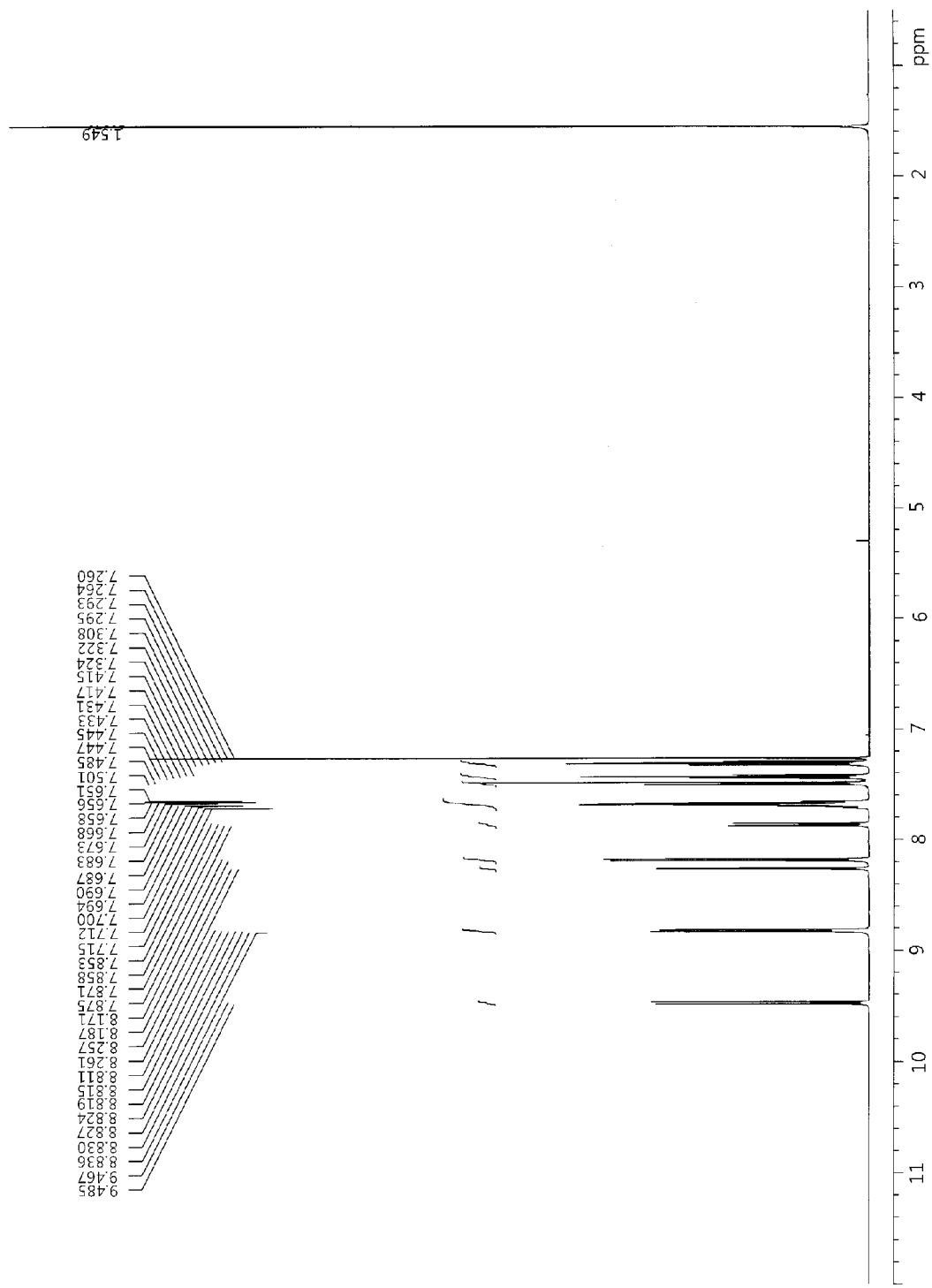
FIG. 4 shows the $^1$H-NMR spectrum of the compound No. 1-1 according to the present invention.

$^1$H-NMR is shown in FIG. 4. $^1$H NMR (CDCl3, δ): 9.46 (d, 2H); 8.82 (d, 4H); 8.28 (s, 2H); 8.17 (d, 4H); 7.82 (dd, 2H); 7.66 (m, 6H); 7.49 (d, 4H); 7.43 (t, 4H); 7.28 (t, 4H).

Synthesis Example 2

Synthesis of Compound 3-1

A mixture of 2.0 g of 9-acetyl-3,6-diiodocarbazole and 3.0 g of N-phenylindolo[2,3-a]carbazole (IC-1) were stirred together in 20 ml N,N'-dimethylacetamide. To this was added 0.8 g of copper oxide and heated to 170° C. for 24 h. The reaction was quenched with water and the solid was filtered, washed with methanol, and dried under vacuum. The solid (4.5 g) was then taken up for further deprotection using 0.8 g KOH with THF (4 ml), methanol (8 ml) and water (8 ml) at reflux temperature. The reaction mixture was then extracted using ethyl acetate; and the organic layer was dried over anhydrous sodium sulfate and evaporated to dryness under vacuum. Subsequent silica gel column chromatography using toluene:hexane (1:2) as eluent, yielded 2.8 g of 3,6-bis(N-phenylindolo[2,3-a]lcarbazolyl)carbazole as a yellow solid.

The above obtained 3,6-bis(N-phenylindolo[2,3-a]lcarbazolyl)carbazole (2.8 g) was dissolved in 50 ml of dry N,N'-dimethylformamide under nitrogen. 0.20 g of sodium hydride was added and stirred at room temperature for 1 h. A solution of 2-chloro-4,6-diphenyl-1,3,5-triazine (U-1, 1.3 g) in dry N,N'-dimethylformamide (15 ml) was then added to the reaction mixture. The reaction was further allowed to stir for 3 h. The product was precipitated by pouring the reaction mixture into water. The solid thus obtained was then washed with methanol, followed by n-hexane and dried under vacuum to obtain 3.1 g of 2,4-diphenyl-6-(3,6-bis(N-phenylindolo[2,3-a]carbazolyl)-carbazole-9'-yl)-1,3,5-triazine, compound 3-1 (86%).

Compound 3-1 showed a melting point of 354° C. and a glass transition temperature of 232° C.

Figure 5:
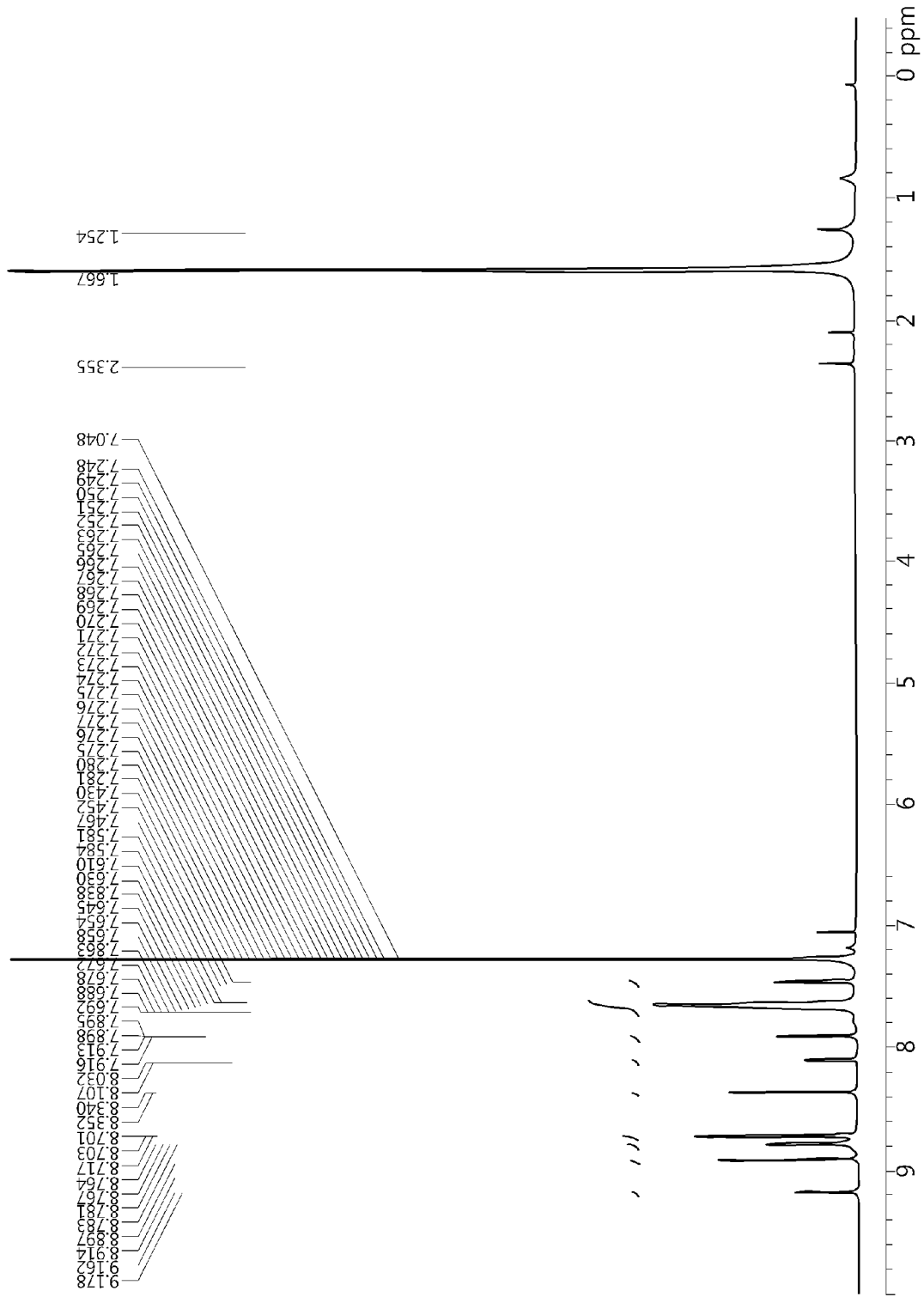
FIG. 5 shows the $^1$H-NMR spectrum of the compound No. 3-1 according to the present invention.

$^1$H-NMR is shown in FIG. 5. $^1$H NMR (CDCl3, δ): 9.16 (d, 2H); 8.89 (d, 2H); 8.78 (dd, 4H); 8.70 (d, 6H); 8.35 (s, 2H); 8.10 (d, 2H); 7.91 (d, 2H); 7.60 (m, 24H); 7.45 (m, 2H).

Synthesis Example 3

Synthesis of Compound 3-8

A mixture of 2.0 g of 9-acetyl-3-bromocarbazole prepared as described above and 2.4 g of N-phenylindolo[2,3-a]carbazole (IC-1) were stirred together in 20 ml N,N'-dimethylacetamide. To this was added 0.8 g of copper oxide and heated to 170° C. for 24 h. The reaction was quenched with water and the solid was filtered, washed with methanol, and dried under vacuum. The solid (4.5 g) was then taken up for further deprotection using 0.8 g KOH with THF (4 ml), methanol (8 ml) and water (8 ml) at reflux temperature. The reaction mixture was then extracted using ethylacetate; and the organic layer was dried over anhydrous sodium sulfate and evaporated to dryness under vacuum. Subsequent silica gel column chromatography using toluene:hexane (1:2) as eluent, yielded 2.9 g of 3-(N-phenylindolo[2,3-a]carbazolyl)carbazole as a light yellow solid.

The above obtained 3-(N-phenylindolo[2,3-a]lcarbazolyl)carbazole (2.9 g) was dissolved in 50 ml of dry N,N'-dimethylformamide under nitrogen. 0.40 g of sodium hydride was added and stirred at room temperature for 1 h. A solution of 2-chloro-4,6-diphenyl-1,3,5-triazine (U-1, 2.3 g) in dry N,N'-dimethylformamide (15 ml) was then added to the reaction mixture. The reaction was further allowed to stir for 3 h. The product was precipitated by pouring the reaction mixture into water. The solid thus obtained was then washed with methanol, followed by n-hexane and dried under vacuum to obtain 3.7 g of 2,4-diphenyl-6-(3,N-phenylindolo[2,3-a]carbazolyl) carbazole-9'-yl)-1,3,5-triazine, compound 3-8 (88%).

Figure 6:
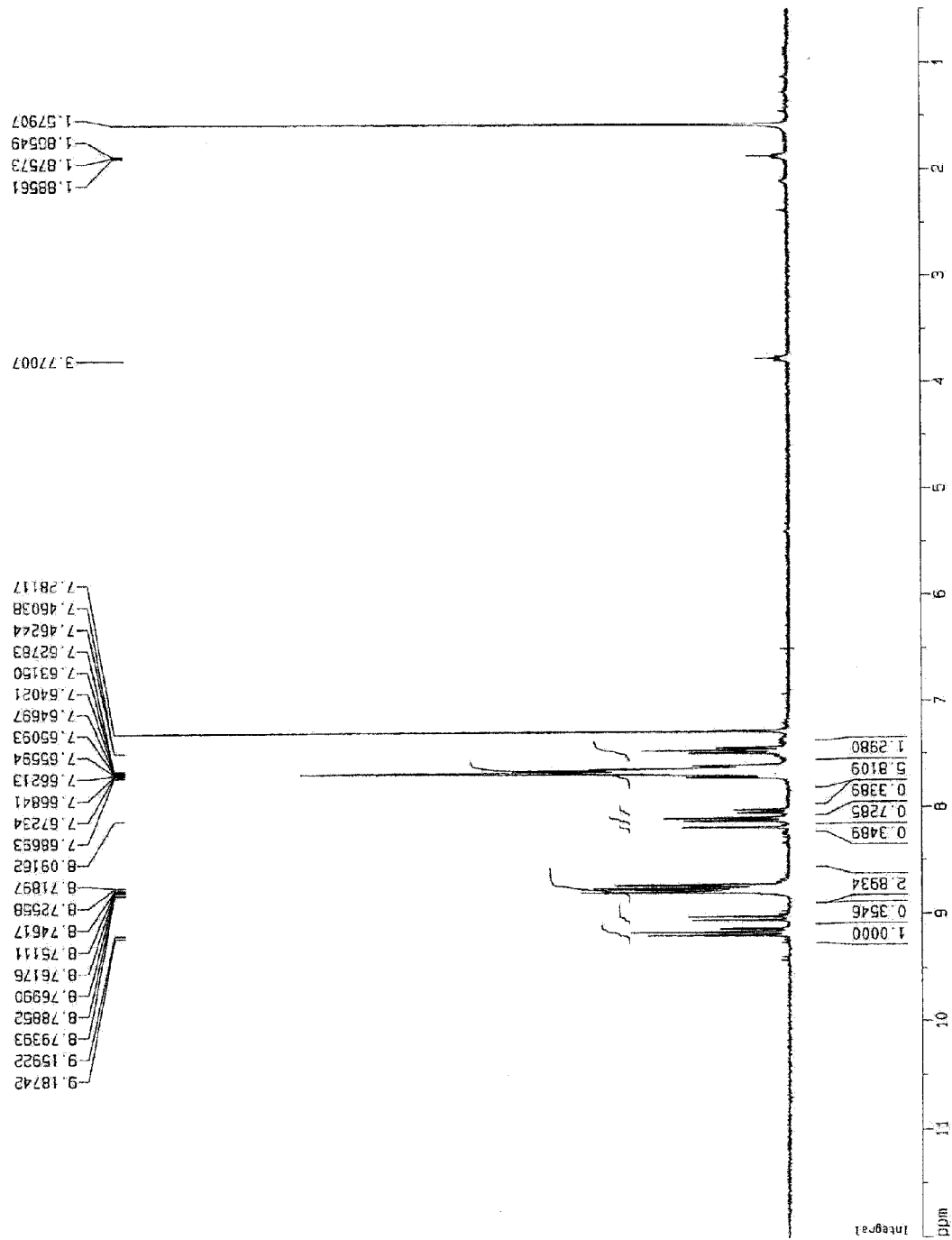
FIG. 6 shows the $^1$H-NMR spectrum of the compound No. 3-8 according to the present invention.

Compound 3-8 showed a melting point of 236° C. $^1$H-NMR is shown in FIG. 6. $^1$H NMR (CDCl3, δ): 9.16 (m, 3H); 9.03 (d, 1H); 8.77 (m, 8H); 8.18 (d, 1H); 8.11 (d, 2H); 8.02 (d, 1H); 7.65 (m, 12H); 7.47 (t, 4H).

Synthesis Example 4

Synthesis of Compound 2-1

A mixture of 4.0 g of 9-Acetyl-3-bromocarbazole prepared as described above and 2.8 g of carbazole were stirred together in 30 ml N,N'-dimethylacetamide. To this was added 0.8 g of copper oxide and heated to 170° C. for 24 h. The reaction was quenched with water and the solid was filtered, washed with methanol, and dried under vacuum. The solid (5.0 g) was then taken up for further deprotection using 1.2 g KOH with THF (6 ml), methanol (12 ml) and water (12 ml) at reflux temperature. The reaction mixture was then extracted using ethylacetate; and the organic layer was dried over anhydrous sodium sulfate and evaporated to dryness under vacuum. Subsequent silica gel column chromatography using toluene:hexane (1:2) as eluent, yielded 3.8 g of 3-(9-carbazolyl)carbazole as a white powder.

The above obtained 3-(9-carbazolyl)carbazole (3.8 g) was dissolved in 60 ml of dry N,N'-dimethylformamide under nitrogen. 0.7 g of sodium hydride was added and stirred at room temperature for 1 h. A solution of 2-chloro-4,6-diphenyl-1,3,5-triazine (U-1, 3.6 g) in dry N,N'-dimethylformamide (25 ml) was then added to the reaction mixture. The reaction was further allowed to stir for 3 h. The product was precipitated by pouring the reaction mixture into water. The solid thus obtained was then washed with methanol, followed by n-hexane and dried under vacuum to obtain 5.4 g of 2,4-diphenyl-6-(3-N-carbazolyl)carbazole-9'-yl)-1,3,5-triazine, compound 2-1 (84%).

Figure 7:
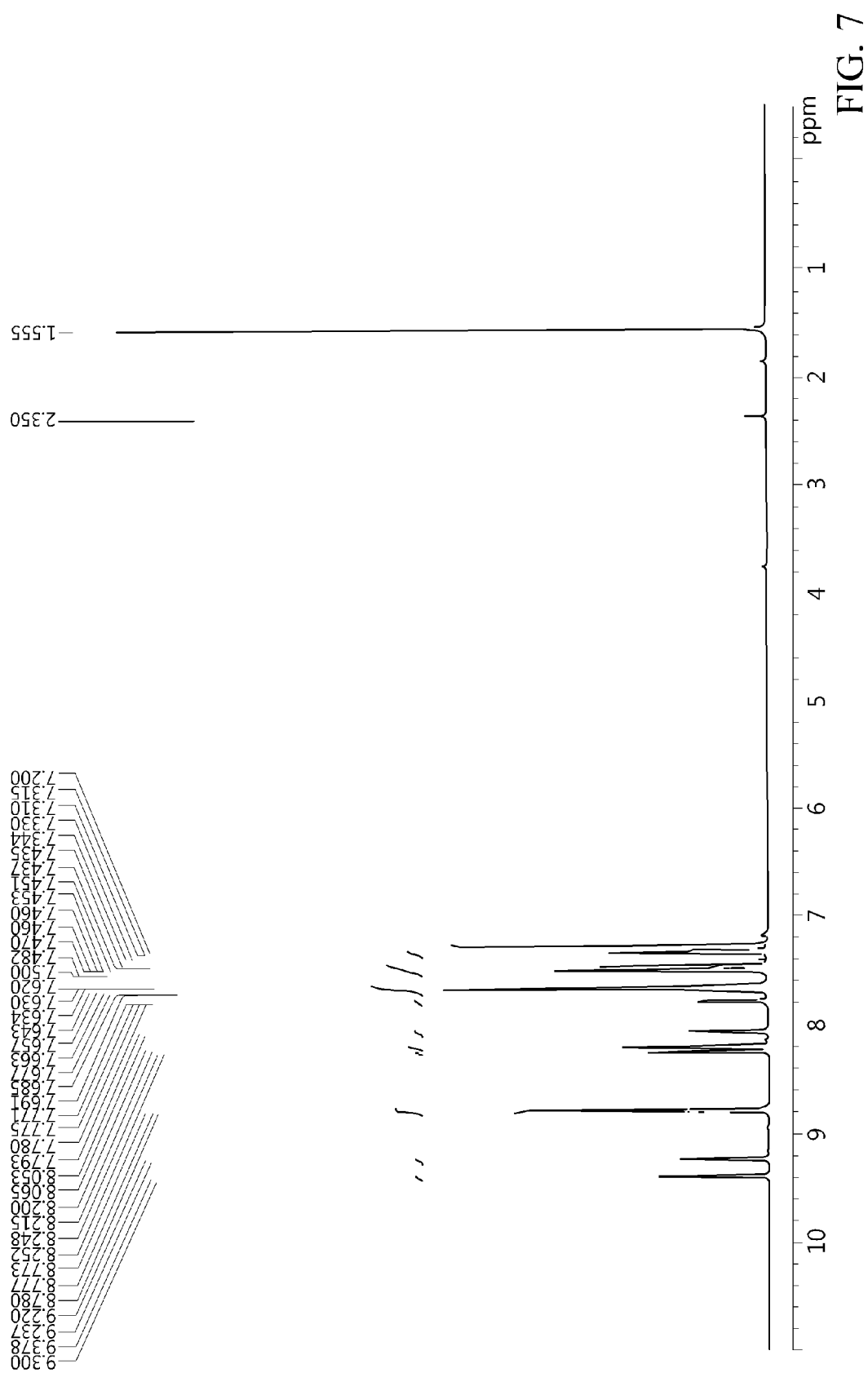
FIG. 7 shows the $^1$H-NMR spectrum of the compound No. 2-1 according to the present invention.

Compound 2-1 showed a melting point of 316° C. and a glass transition temperature of 130° C.
$^1$H-NMR is shown in FIG. 7. $^1$H NMR (CDCl3, δ): 9.37 (d, 1H); 9.22 (d, 1H); 8.77 (dd, 4H); 8.25 (s, 1H); 8.20 (d, 2H); 8.06 (d, 1H); 7.77 (dd, 1H); 7.62 (m, 7H); 7.43 (m, 5H); 7.31 (t, 2H).

Synthesis Example 5

Synthesis of Compound 3-14

Compound 3-14 was synthesized according to the procedure described in Synthesis Example 3, except N-ethylindolo[2,3-a]carbazole (IC-6) was used in place of N-phenylindolo[2,3-a]carbazole (IC-1).

Figure 8:
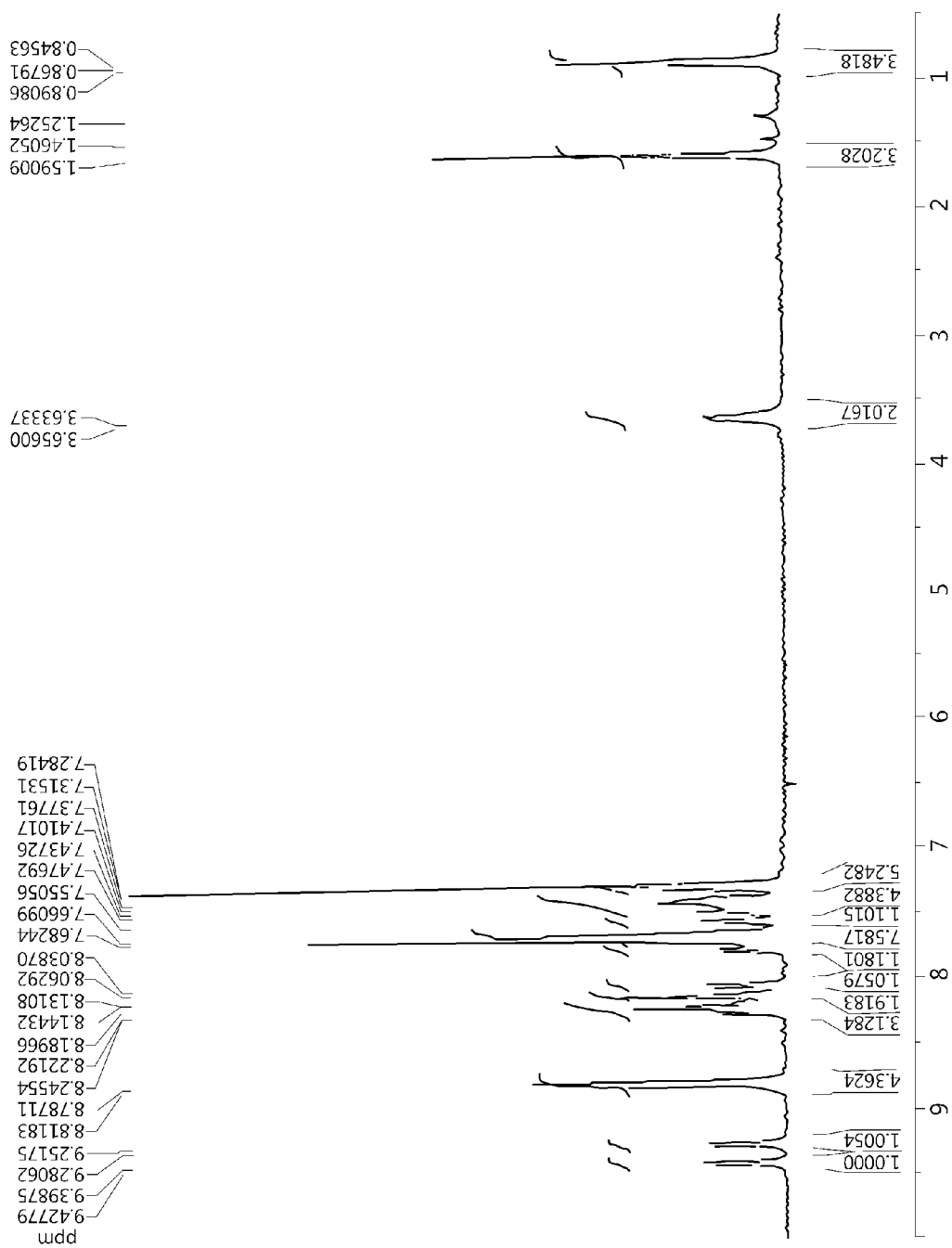
FIG. 8 shows the $^1$H-NMR spectrum of the compound No. 3-14 according to the present invention.

Compound 3-14 showed a melting point of 320° C.
$^1$H-NMR is shown in FIG. 8. $^1$H NMR (CDCl3, δ): 9.43 (d, 1H); 9.25 (d, 1H); 8.78 (d, 4H); 8.22 (m, 3H); 8.14 (m, 2H); 8.04 (d, 1H); 7.68 (m, 8H); 7.55 (d, 1H); 7.38 (m, 4H); 7.28 (m, 1H); 3.63 (m, 2H); 0.85 (m, 3H).

Synthesis Example 6

Synthesis of Compound 4-1

A mixture of 4.0 g of 9-acetyl-2,7-diiodocarbazole and 2.2 g of carbazole were stirred together in 20 ml N,N'-dimethylacetamide. To this was added 1.6 g of copper oxide and heated to 170° C. for 24 h. The reaction was quenched with water and the solid was filtered, washed with methanol, and dried under vacuum. The solid (6 g) was then taken up for further deprotection using 1.2 g KOH with THF (6 ml), methanol (12 ml) and water (12 ml) at reflux temperature. The reaction mixture was then extracted using ethyl acetate; and the organic layer was dried over anhydrous sodium sulfate and evaporated to dryness under vacuum. Subsequent silica gel column chromatography using toluene:hexane (1:2) as eluent, yielded 3.0 g of 2,7-dicarbazolylcarbazole.

The above obtained 2,7-di(9-carbazolyl)carbazole (3.0 g) was dissolved in 50 ml of dry N,N'-dimethylformamide under nitrogen. 0.30 g of sodium hydride was added and stirred at room temperature for 1 h. A solution of 2-chloro-4,6-diphenyl-1,3,5-triazine (U-1, 2.0 g) in dry N,N'-dimethylformamide (20 ml) was then added to the reaction mixture. The reaction was further allowed to stir for 3 h. The product was precipitated by pouring the reaction mixture into water. The solid thus obtained was then washed with methanol and dried under vacuum to obtain 3.5 g of 2,4-diphenyl-6-(2,7-di(9-carbazolyl)carbazole-9'-yl)-1,3,5-triazine, compound 4-1 (81%).

Figure 9:
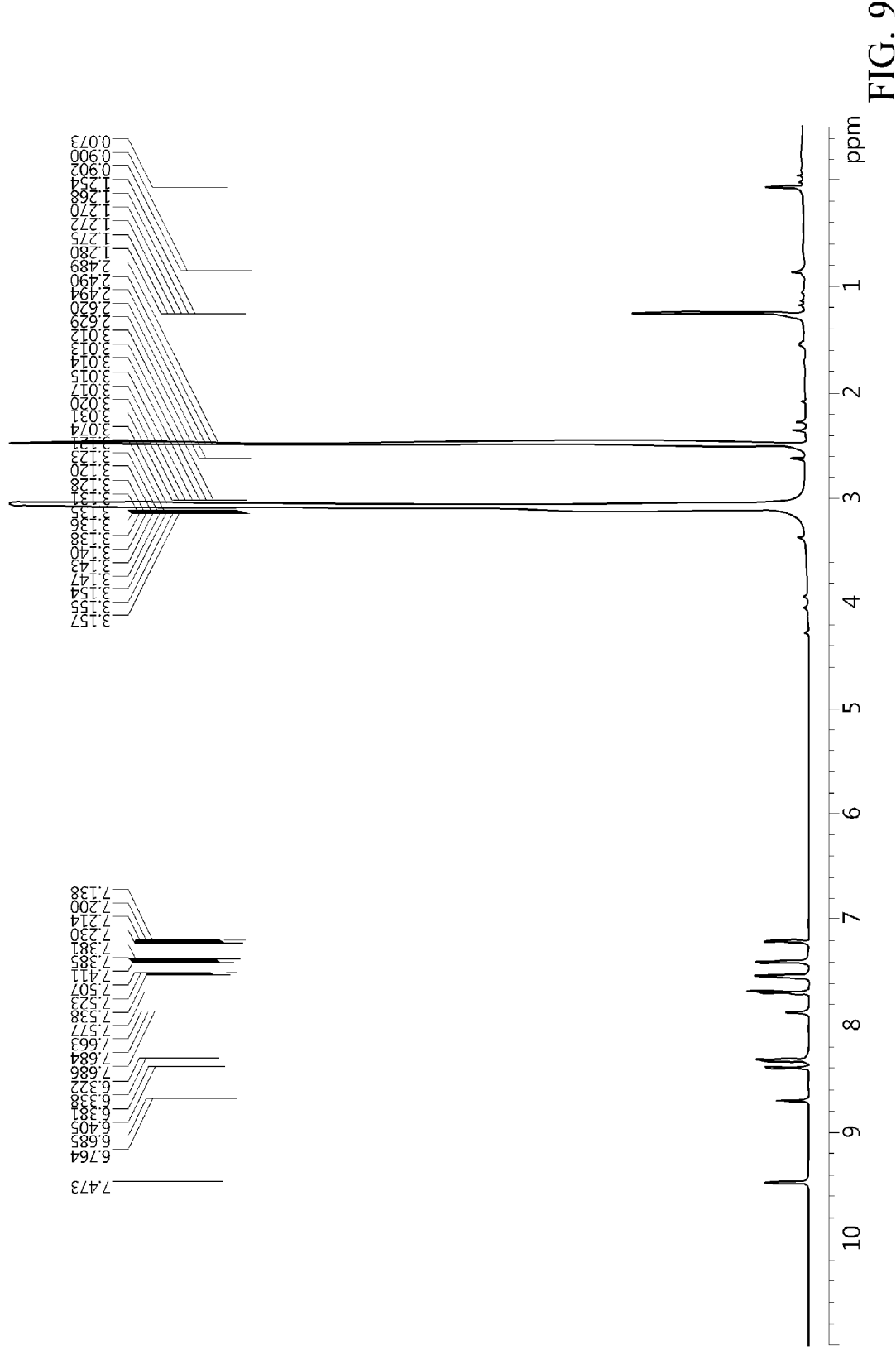
FIG. 9 shows the $^1$H-NMR spectrum of the compound No. 4-1 according to the present invention.

Compound 4-1 showed a melting point of 402° C. and a glass transition temperature of 177° C. $^1$H-NMR is shown in FIG. 9. $^1$H NMR (CDCl3, δ): 9.47 (s, 2H); 8.73 (d, 2H); 8.40 (d, 4H); 8.35 (d, 4H); 7.90 (d, 2H); 7.69 (d, 4H); 7.53 (m, 6H); 7.39 (t, 4H); 7.18 (t, 4H).

Synthesis Example 7

Synthesis of Compound 2-11

3-(9-carbazolyl)carbazole (3.8 g), prepared as in the synthesis example 4, was dissolved in 60 ml of dry N,N'-dimethylformamide under nitrogen. 0.7 g of sodium hydride was added and stirred at room temperature for 1 h. A solution of 2-chloro-4,6-di(3-methylphenyl)-1,3,5-triazine (U-2, 4.0 g) in dry N,N'-dimethylformamide (25 ml) was then added to the reaction mixture. The reaction was further allowed to stir for 3 h. The product was precipitated by pouring the reaction mixture into water. The solid thus obtained was then washed with methanol, followed by n-hexane and dried under vacuum to obtain 5.8 g of 2,4-di(3-methylphenyl)-6-(3-N-carbazolyl)carbazole-9'-yl)-1,3,5-triazine, compound 2-11 (89%).

Figure 10:
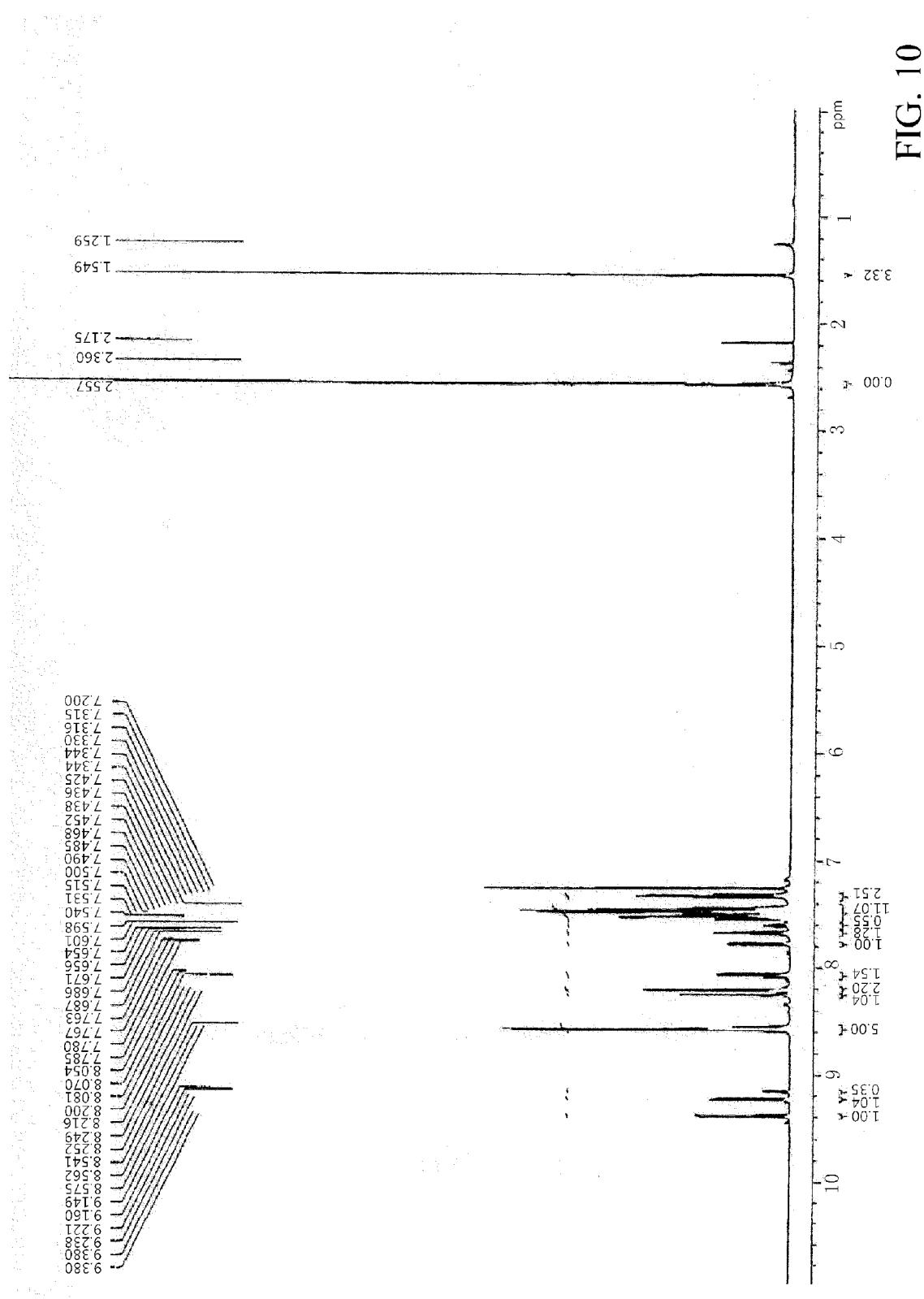
FIG. 10 shows the $^1$H-NMR spectrum of the compound No. 2-11 according to the present invention.

Compound 2-11 showed a glass transition temperature of 99° C.
$^1$H-NMR is shown in FIG. 10. $^1$H NMR (CDCl3, δ): 9.38 (d, 1H); 9.23 (d, 1H); 8.57 (m, 4H); 8.25 (s, 1H); 8.21 (d, 2H); 8.07 (d, 1H); 7.78 (dd, 1H); 7.68 (t, 1H); 7.54 (m, 9H); 7.34 (t, 2H); 2.55 (s, 6H).

Synthesis Example 8

Synthesis of Compound 8-8

A solution of 9-benzyl-3-bromocarbazole in dry tetrahydrofuran (15 g, 100 ml) was cooled to −78° C., added n-butyllithium (25 ml, 2.5M solution in hexane). After 3 h of stirring, added 10.8 g diphenylchlorophosphine and allowed the reaction to equilibrate to room temperature, overnight. The reaction mixture was quenched with 10% ammonium chloride solution and extracted with ethyl acetate. The ethyl acetate layer was thoroughly washed with water, dried over anhydrous sodium sulfate and evaporated under vacuum. A sticky residue (16 g) was obtained which was further dissolved in 50 ml dichloromethane and 50 ml of 30% aqueous hydrogen peroxide solution was added and stirred overnight at room temperature. After the completion of reaction, the dichloromethane layer was separated, washed with water, dried over anhydrous sodium sulfate and evaporated using a rotavac. The sticky mass obtained thus was further purified by a silica gel-column chromatography using dichloromethane as the solvent. This furnished 12 g of 9-benzyl-3-carbazolyl (diphenyl)phosphine oxide. This was further debenzylated using 0.1 g of activated palladium on charcoal in methanol (80 ml). The methanol layer was passed through a short celite column and the solvent was evaporated to dryness to yield 8 g of 9H-3-carbazolyl(diphenyl)phosphine oxide.

9H-3-carbazolyl(diphenyl)phosphine oxide (8 g), prepared as above, was dissolved in 120 ml of dry N,N'-dimethylformamide under nitrogen. 1.2 g of sodium hydride was added and stirred at room temperature for 1 h. A solution of 2-chloro-4,6-diphenyl-1,3,5-triazine (U-1, 7.0 g) in dry N,N'-dimethylformamide (50 ml) was then added to the reaction mixture. The reaction was further allowed to stir for 24 h. The product was precipitated by pouring the reaction mixture into water. The solid thus obtained was then washed with methanol, followed by n-hexane and dried under vacuum to obtain 9 g of 9-(4,6-diphenyl-1,3,5-triazin-2-yl)-9H-3-carbazolyl (diphenyl)phosphine oxide, compound 8-8 (71%).

Compound 8-8 showed a melting point of 255° C.

Figure 11:
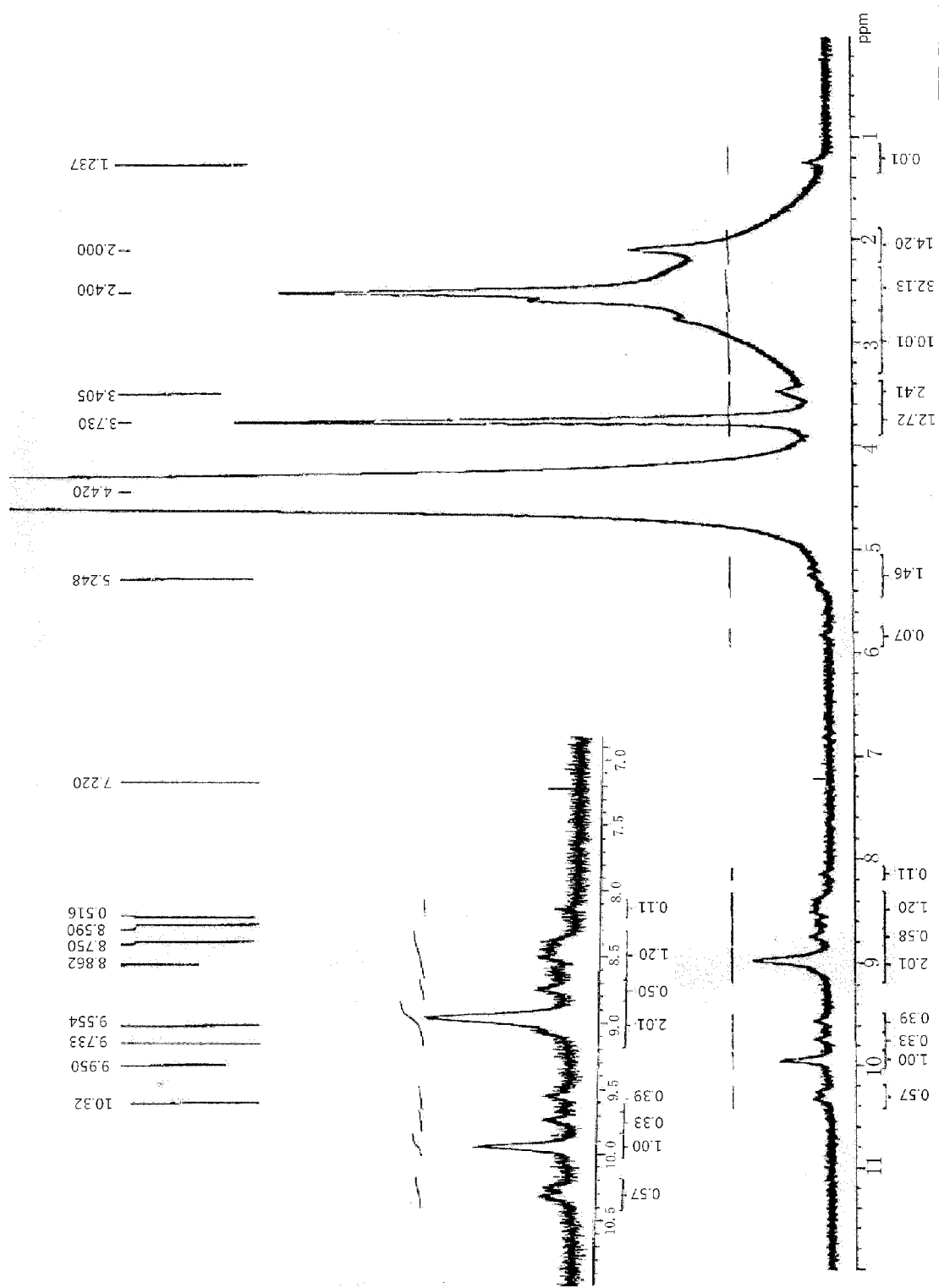
FIG. 11 shows the $^1$H-NMR spectrum of the compound No. 8-8 according to the present invention.

$^1$H-NMR is shown in FIG. 11. $^1$H NMR (DMSO-d$_6$, δ): 10.32 (d, 2H); 9.95 (s, 4H); 9.73 (m, 1H); 9.55 (m, 1H); 8.86 (m, 11H); 8.75 (m, 2H); 8.58 (m, 6H).

Example 1

Fabrication of Organic Electroluminescent Device

Prior to use, the substrate was degreased with solvents and cleaned in a UV ozone before it was loaded into the evaporation system. The substrate was then transferred into a vacuum deposition chamber for deposition of all other layers on top of the substrate. The following layers were deposited in the following sequence, as shown in FIG. 2, by evaporation from a heated boat under a vacuum of approximately $10^{-6}$ Torr:

a) a hole injection layer, EHI609 (from E-ray optoelectronics Tech Co Ltd, Taiwan);

b) a hole transport layer, 7 nm thick, including N,N-di-1-naphthyl-N,N'-diphenyl-4,4'-diaminobiphenyl (NPB);

c) an exciton-blocking layer, 5 nm thick, including 4,4',4'-tris(carbazol-9-yl)-triphenylamine (TCTA);

d) a light emitting layer, 30 nm thick, including compound 1-1 doped with 7% Ir(ppy)$_3$ by volume;

e) an electron transport layer, 40 nm thick, including tris-(8-hydroxyquinoline) aluminum (Alq$_3$);

f) an electron injection layer, 1 nm thick, LiF; and g) a cathode: approximately 150 nm thick, including Al.

The structure of the organic electroluminescent device may be denoted as: ITO/EHI609 (70 nm)/NPB (7 nm)/TCTA (5 nm)/compound 1-1:7% Ir(ppy)$_3$ (30 nm)/Alq$_3$ (30 nm)/LiF (1 nm)/Al (150 nm)

Figure 12:
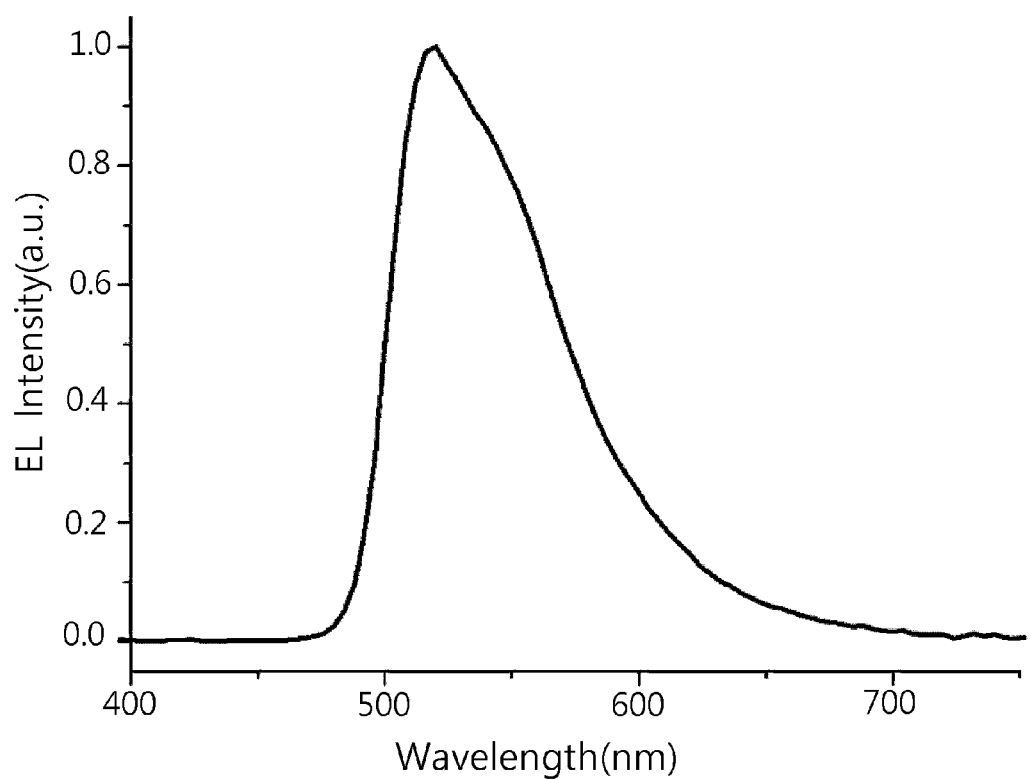
FIG. 12 shows the electroluminescent spectrum of the organic electroluminescent device of Example 2 according to the present invention.

After the deposition of these layers, the device was transferred from the deposition chamber into a dry box for encapsulation, and subsequently encapsulated by using a UV-curable epoxy, and a glass lid containing a moisture getter. The organic electroluminescent device has an emission area of 3 mm$^2$. The organic electroluminescent device thus obtained was connected to an outside power source, and upon applying direct current voltage, emission of light with the characteristics shown in Table 13 were confirmed. The electroluminescent spectrum of this device is shown in FIG. 12.

The EL characteristics of all the fabricated devices in the present invention were evaluated using a constant current source (KEITHLEY 2400 Source Meter, made by Keithley Instruments, Inc., Cleveland, Ohio) and a photometer (PHOTO RESEARCH SpectraScan PR 650, made by Photo Research, Inc., Chatsworth, Calif.) at room temperature.

Operational lifetime (or stability) of the devices were tested at the room temperature and at an initial luminance of 10,000 cd/m$^2$ by driving a constant current through the devices. The color was reported using Commission Internationale de l'Eclairage (CIE) coordinates.

Examples 2-4

Examples 2-4 are the electroluminescent devices fabricated using compounds 4-1, 3-14, 2-1, respectively, according to the device structure provided in Example 1.

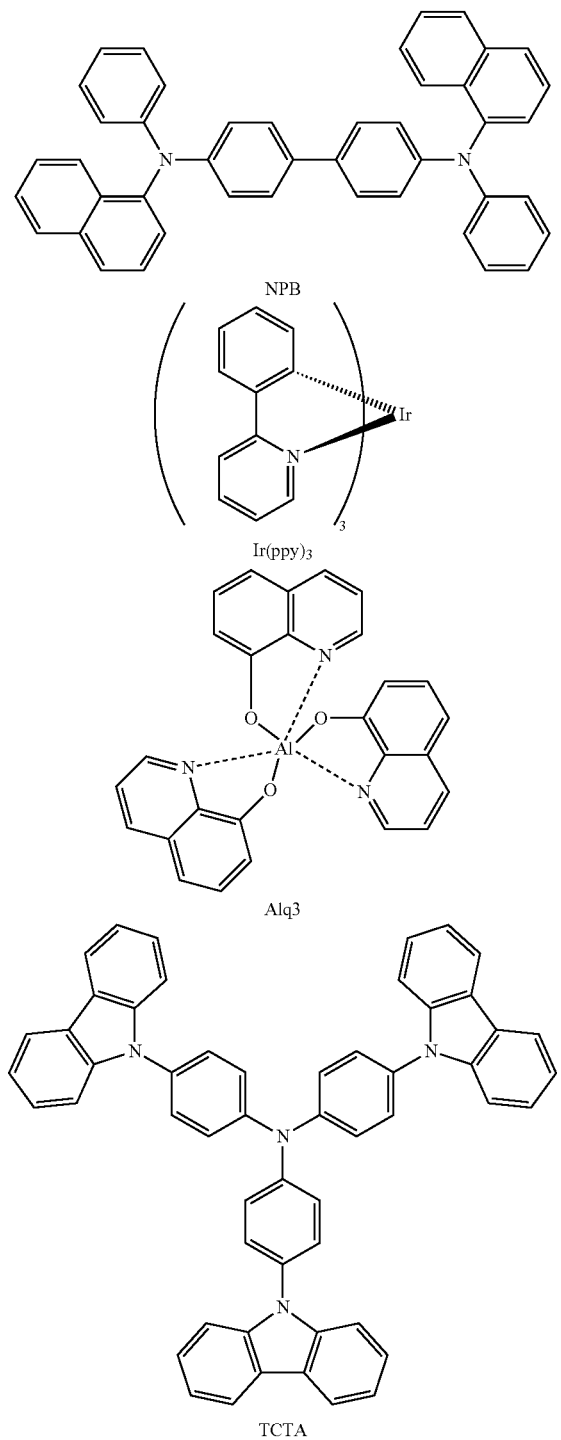

NPB

Ir(ppy)$_3$

Alq3

TCTA

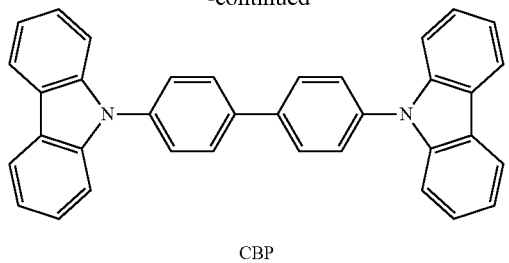

CBP

Comparative Example

Fabrication of Organic Electroluminescent Device

An organic phosphorescent electroluminescent device was fabricated as a structure similar to the layer structure as example 1 except that CBP was used in place of the compound 1-1 in the light emitting layer. The structure of the organic phosphorescent electroluminescent device may be denoted as: ITO/DNTPD (75 nm)/NPB (7 nm)/TCTA (5 nm)/CBP: 7% $Ir(ppy)_3$ (30 nm)/$Alq_3$ (30 nm)/LiF (1 nm)/Al (150 nm).

Figure 13:
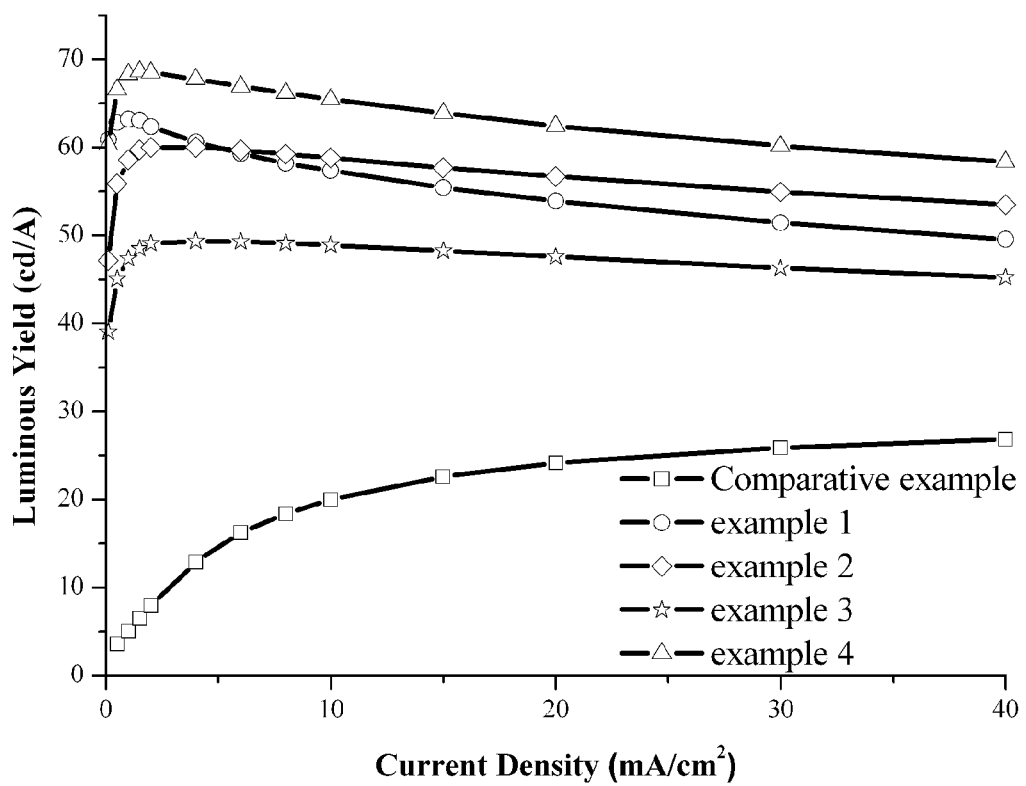
FIG. 13 shows the plot of luminance against current density of the electroluminescent devices according to the present invention.

The peak wavelength of emitted light, maximum luminous efficiency, and driving voltage of the organic electroluminescent devices fabricated in the examples are shown in Table 13. A plot of current density vs luminance is shown in FIG. 13.

TABLE 13

|  | Compound of Light Emitting Layer | Peak wavelength (nm) | Max. luminous efficiency (cd/A) @ 10 mA/cm² | Driving voltage (V) |
| --- | --- | --- | --- | --- |
| Example 1 | Compound 1-1 | 520 | 54.57 | 5.82 |
| Example 2 | Compound 3-1 | 520 | 58.80 | 6.32 |
| Example 3 | Compound 3-14 | 520 | 48.90 | 5.16 |
| Example 4 | Compound 2-1 | 516 | 65.47 | 6.11 |
| Comparative Example | CBP | 516 | 20.00 | 8.35 |

The invention shall not be limited to the above described embodiments, methods and examples.

INDUSTRIAL APPLICABILITY

As described above in detail, the organic electroluminescent device having the material for the organic electroluminescent device of the present invention has high luminous efficiency, high thermal stability, sufficiently low driving voltage and long lifetime.

Therefore, the organic electroluminescent device of this invention is applicable to flat panel displays, mobile phone displays, light sources utilizing the characteristics of planar light emitters, sign-boards and has a high technical value.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

The invention claimed is:

1. A compound of formula (I) for an organic electroluminescent device:

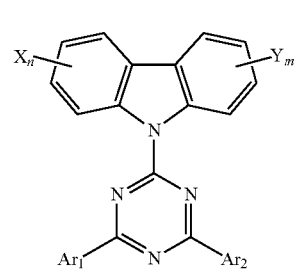

(I)

wherein X and Y are each independently selected for the group consisting of an alkyl substituted, aryl substituted or unsubstituted carbazole, indolocarbazole, triphenylsilyl, and diphenylphosphine oxide represented by formula (A), (B), (C), (D) or (E),

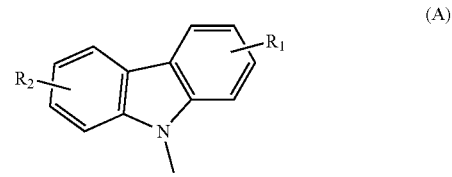

(A)

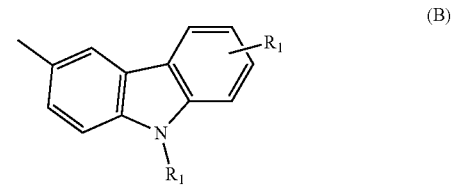

(B)

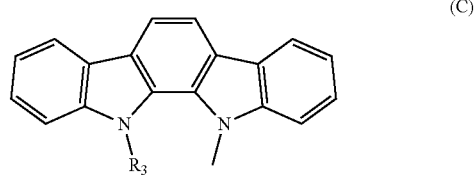

(C)

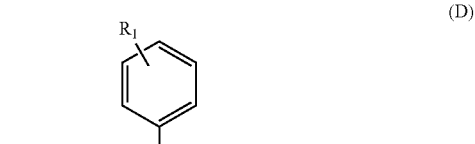

(D)

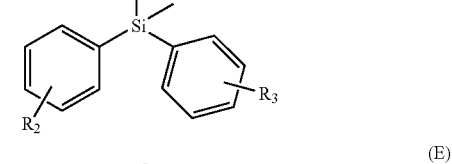

(E)

in which $R_1$, $R_2$, and $R_3$ are each independently selected from the group consisting of a hydrogen, an alkyl having 1 to 15 carbons atoms, an aryl group having 6 to 15 carbons atoms, an alkyl substituted, aryl substituted or unsubstituted triphenylsilyl and diphenylphosphine oxide represented by the formula (D) or (E); m and n are each independently 0 or 1, provided that m+n is 1 or more; and $Ar_1$ and $Ar_2$ are each independently selected from the group consisting of an alkyl substituted, aryl substituted or unsubstituted phenyl, tolyl, naphthyl, fluorenyl, anthracenyl, and phenanthryl.

2. The compound of claim 1, being one of compounds represented by formulae (II) to (XIII):

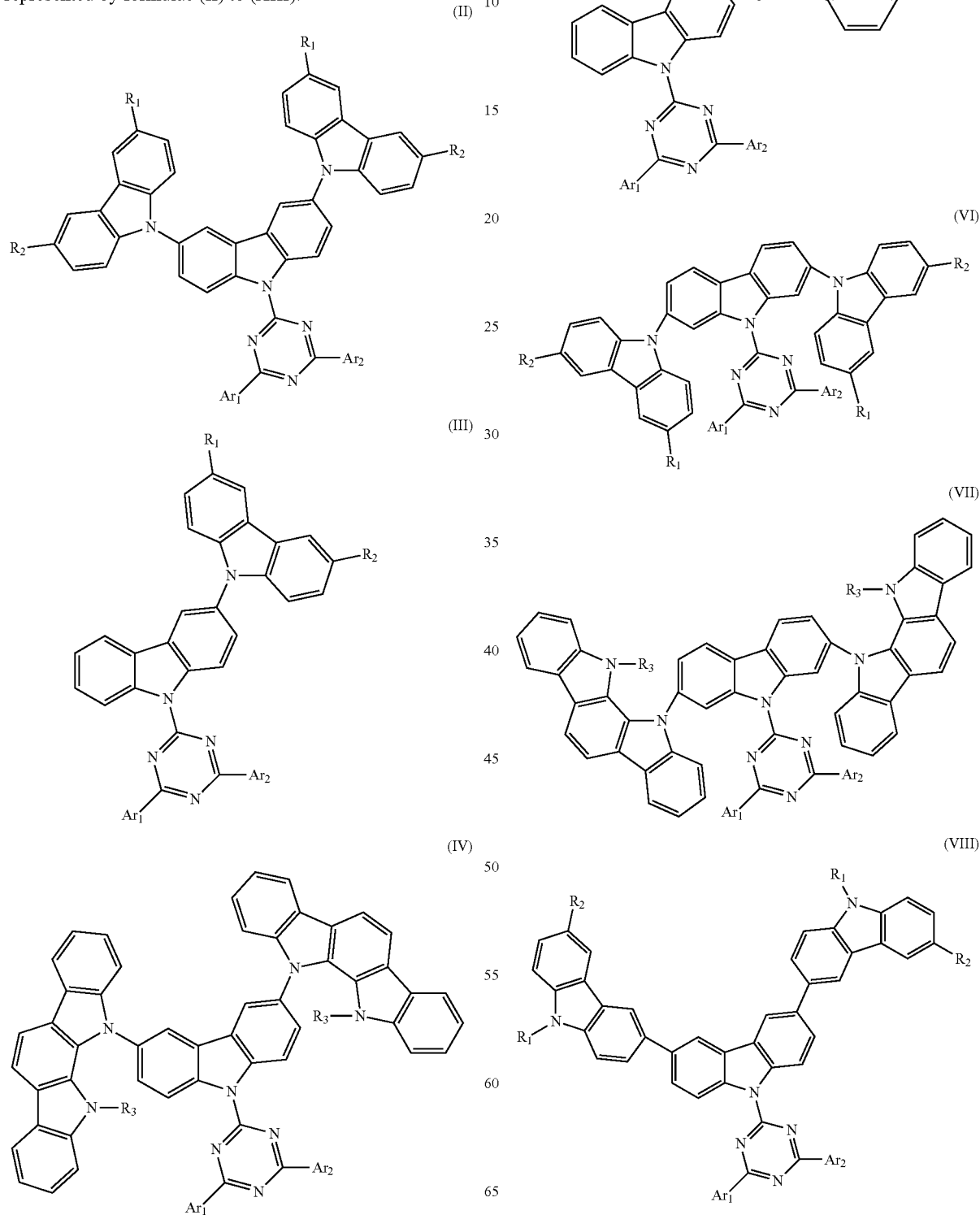

-continued (IX)

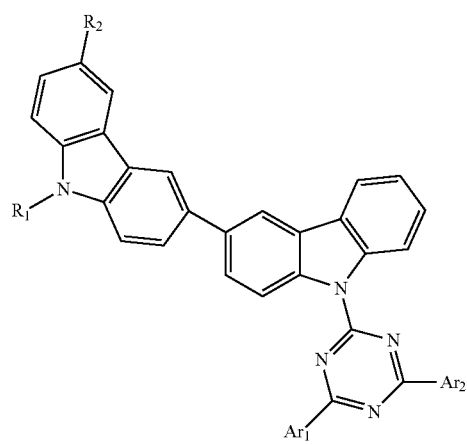

(X)

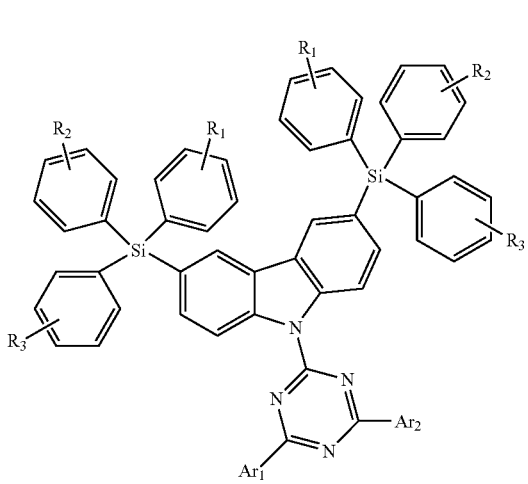

(XI)

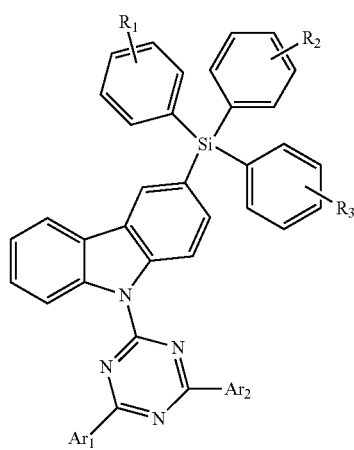

-continued (XII)

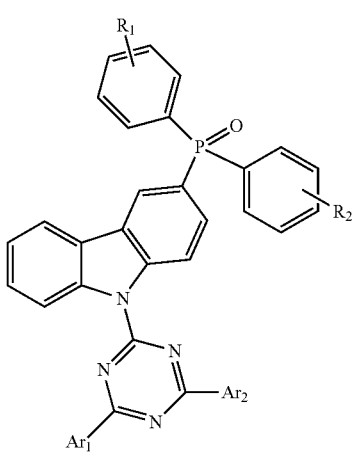

(XIII)

wherein $R_1$, $R_2$ and $R_3$ are each independently selected from the group consisting of a hydrogen, a substituted or unsubstituted alkyl group having 1 to 10 carbon atoms, a substituted or unsubstituted cycloalkyl group having 5 to 10 carbon atoms, a substituted or unsubstituted aralkyl group having 7 to 15 carbon atoms, a substituted or unsubstituted aromatic hydrocarbon group having 6 to 15 carbon atoms, an alkyl substituted, an aryl substituted or unsubstituted triphenylsilyl, and a diphenylphosphine oxide represented by the formula (D) or (E); m and n each independently represent 0 or 1, provided that m+n is 1 or more; and $Ar_1$ and $Ar_2$ are each independently selected from the group consisting of an alkyl substituted, aryl substituted or unsubstituted phenyl, tolyl, naphthyl, fluorenyl, anthracenyl, and phenanthryl.

3. A light emitting layer for an organic electroluminescent device, comprising:
a phosphorescent dopant; and
a compound of formula (I)

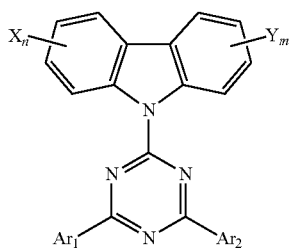

(I)

wherein X and Y are each independently selected for the group consisting of an alkyl substituted, aryl substituted or unsubstituted carbazole, indolocarbazole, triphenylsilyl, and diphenylphosphine oxide represented by formula (A), (B), (C), (D) or (E),

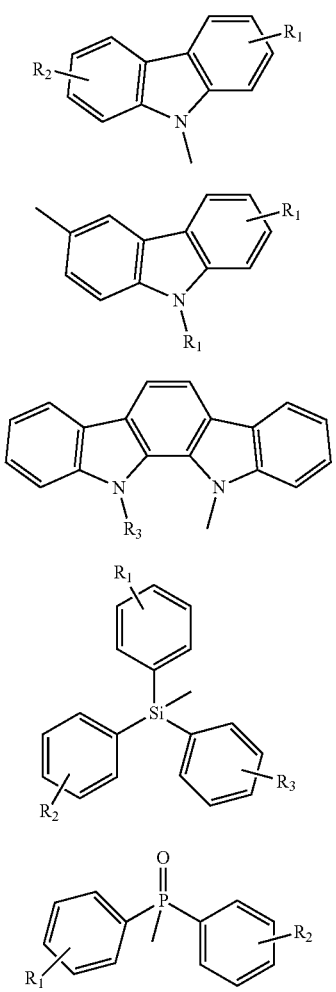

in which $R_1$, $R_2$, and $R_3$ are each independently selected from the group consisting of a hydrogen, an alkyl having 1 to 15 carbons atoms, an aryl group having 6 to 15 carbons atoms, an alkyl substituted, aryl substituted or unsubstituted triphenylsilyl, and diphenylphosphine oxide represented by the formula (D) or (E); m and n are each independently 0 or 1, provided that m+n is 1 or more; and $Ar_1$ and $Ar_2$ are each independently selected from the group consisting of an alkyl substituted, aryl substituted or unsubstituted phenyl, tolyl, naphthyl, fluorenyl, anthracenyl, and phenanthryl.

4. The light emitting layer of claim 3, wherein the compound is one of compounds represented by formulae (II) to (XIII):

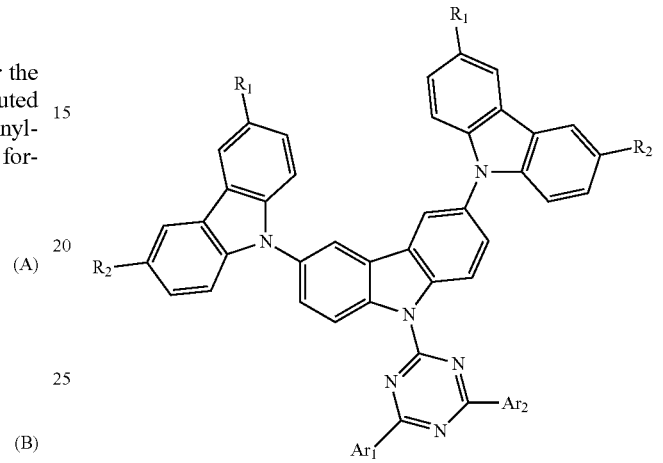

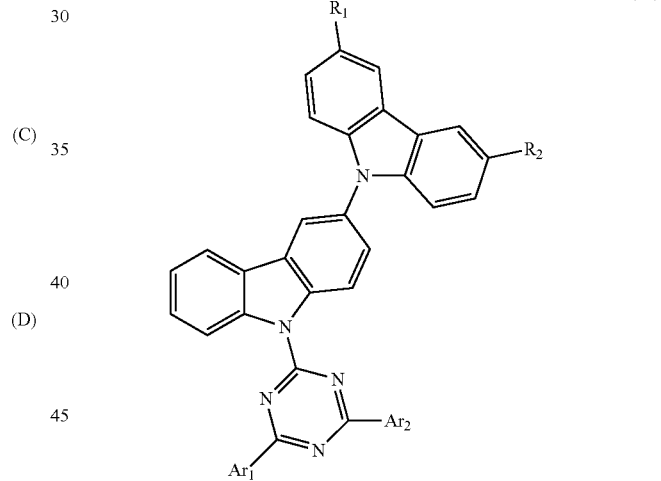

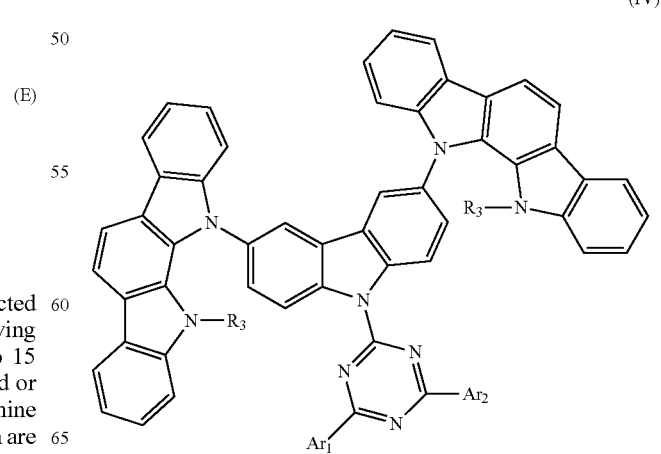

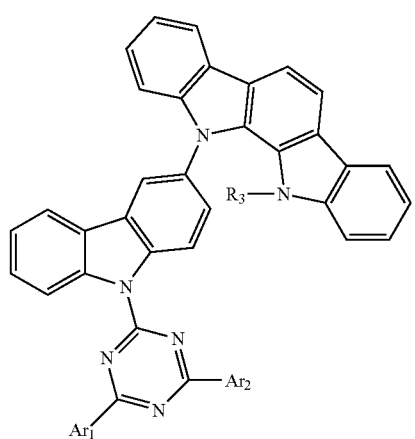
(V)
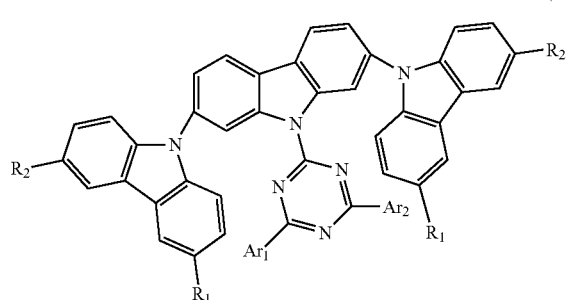
(VI)
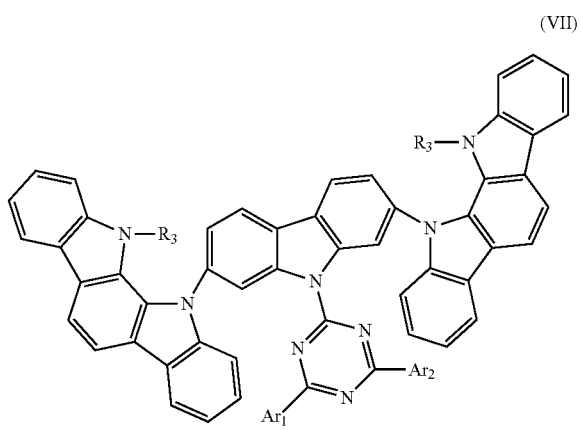
(VII)
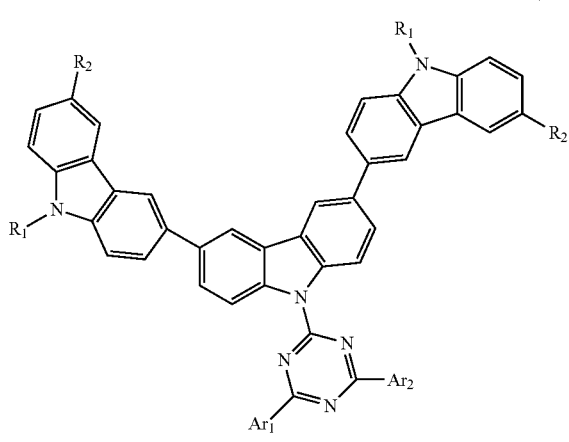
(VIII)
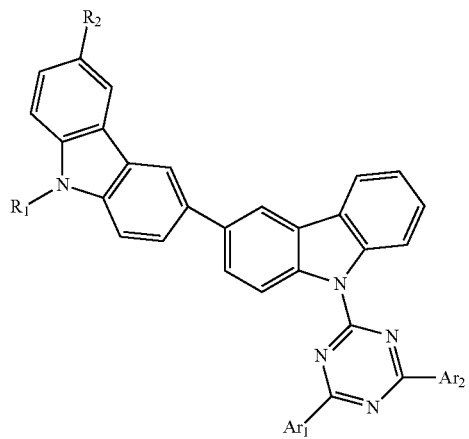
(IX)
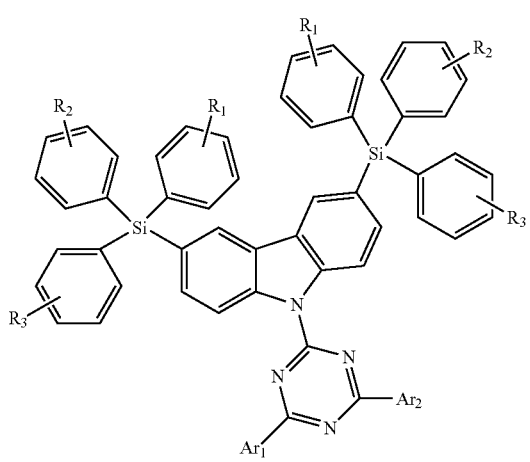
(X)
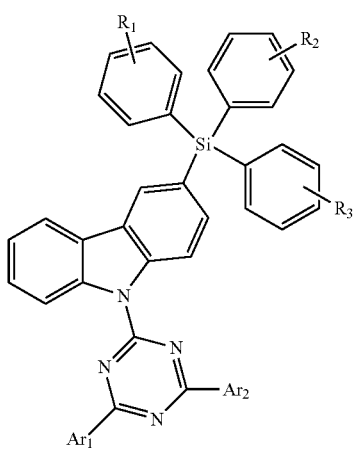
(XI)

(XII)

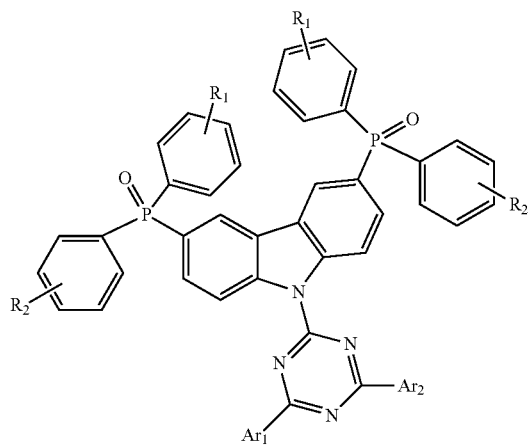

(XIII)

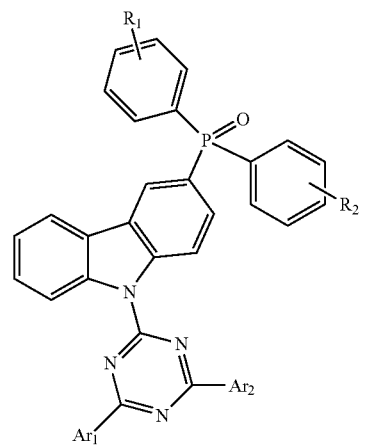

(II)

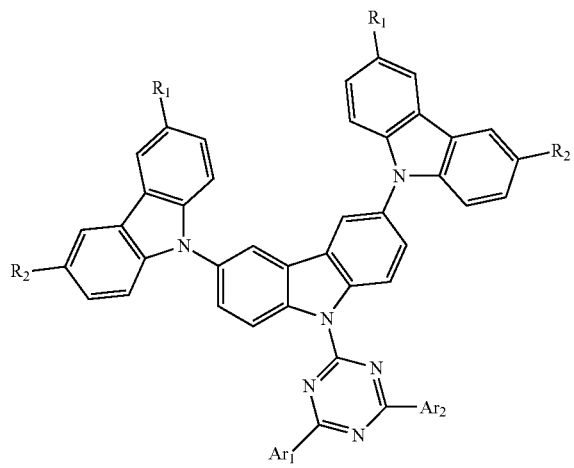

(III)

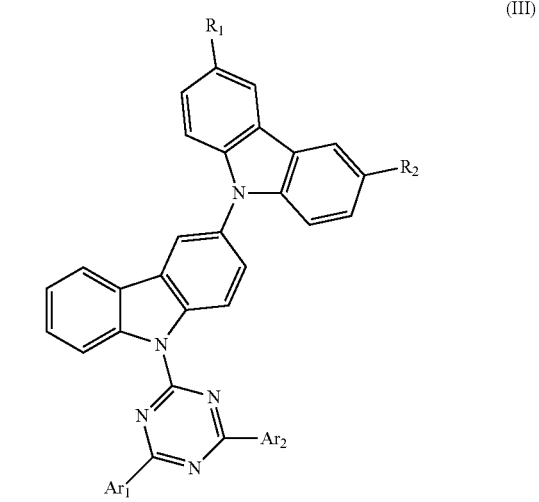

(IV)

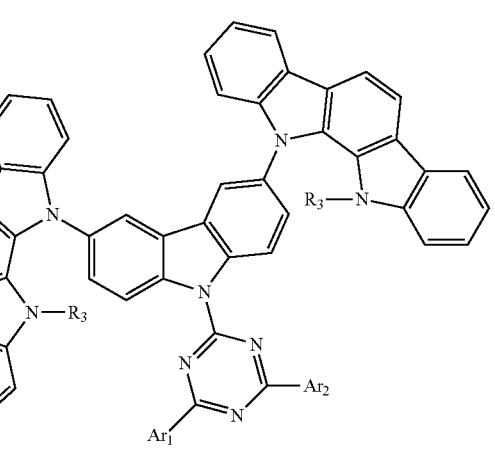

wherein $R_1$, $R_2$ and $R_3$ are each independently selected from the group consisting of a hydrogen, a substituted or unsubstituted alkyl group having 1 to 10 carbon atoms, a substituted or unsubstituted cycloalkyl group having 5 to 10 carbon atoms, a substituted or unsubstituted aralkyl group having 7 to 15 carbon atoms, a substituted or unsubstituted aromatic hydrocarbon group having 6 to 15 carbon atoms, an alkyl substituted, an aryl substituted or unsubstituted triphenylsilyl, and a diphenylphosphine oxide represented by the formula (D) or (E); m and n each independently represent 0 or 1, provided that m+n is 1 or more; and $Ar_1$ and $Ar_2$ are each independently selected from the group consisting of an alkyl substituted, aryl substituted or unsubstituted phenyl, tolyl, naphthyl, fluorenyl, anthracenyl, and phenanthryl.

5. The light emitting layer of claim 3, wherein the phosphorescent dopant is an organic metal complex comprising at least one metal selected from the group consisting of ruthenium, rhodium, palladium, silver, rhenium, osmium, iridium, platinum, and gold.

6. The light emitting layer of claim 3, wherein the phosphorescent dopant is one of $Ir(ppy)_3$, $Ir(bt)_2(acac)$, FIrpic, and $PtOEt_3$.

7. The light emitting layer of claim 3, wherein the phosphorescent dopant is in a range from 3 wt % to 10 wt % based on total weight of the light emitting layer.

8. An organic electroluminescent device, comprising:
a light emitting layer having a compound of a formula selected from formulae (II) to (XIII) and a phosphorescent dopant (V)
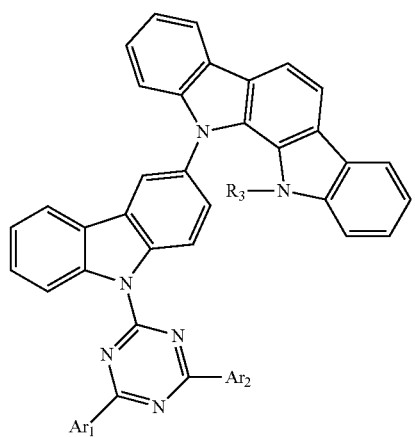
(VI)
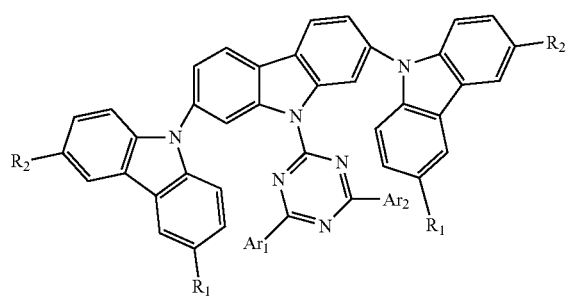
(VII)
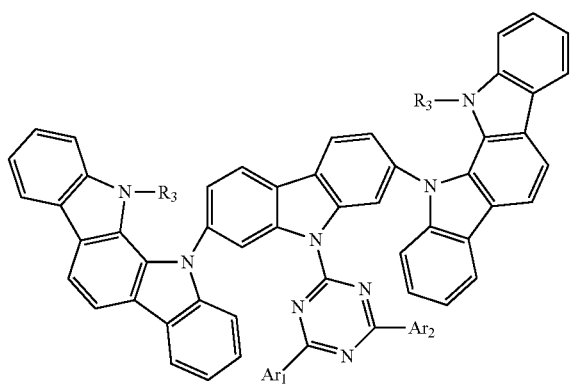
(VIII)
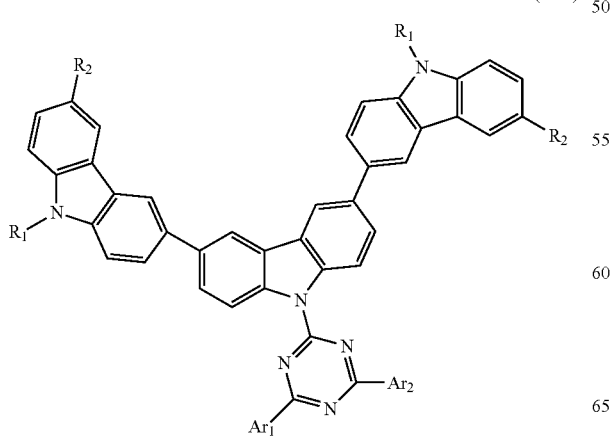
(IX)
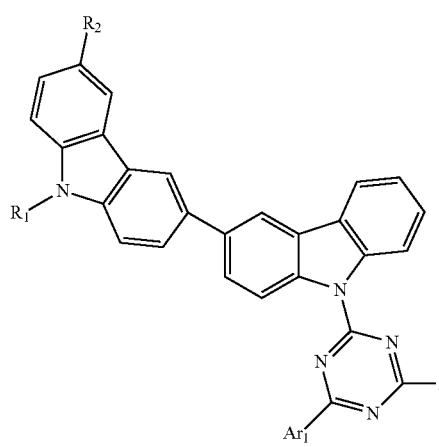
(X)
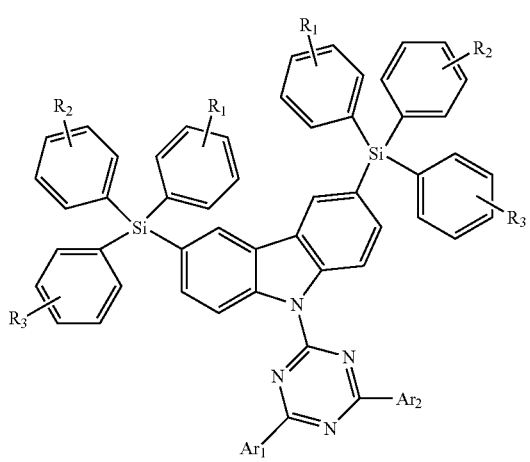
(XI)
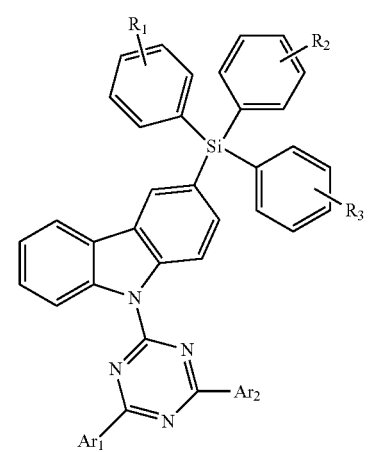

-continued

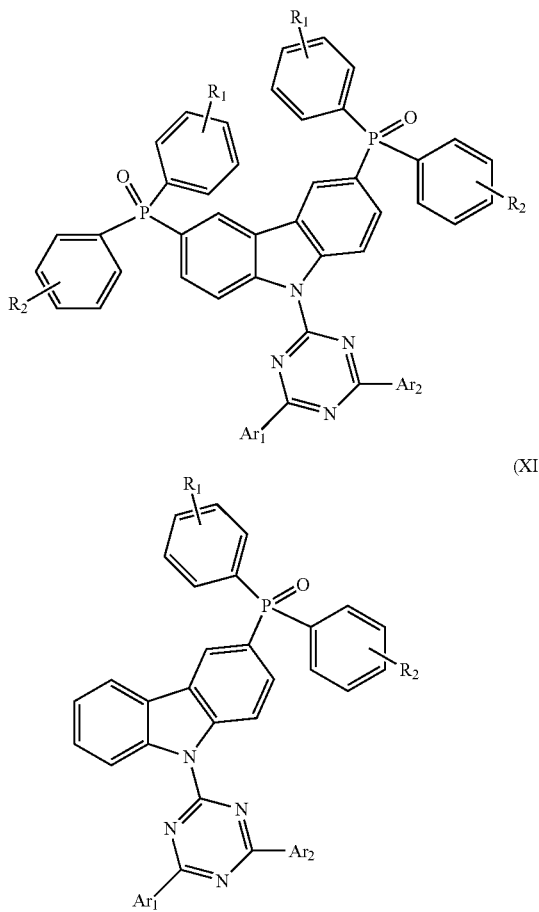

wherein $R_1$, $R_2$, and $R_3$ are each independently selected from the group consisting of a hydrogen, a substituted or unsubstituted alkyl group having 1 to 10 carbon atoms, a substituted or unsubstituted cycloalkyl group having 5 to 10 carbon atoms, a substituted or unsubstituted aralkyl group having 7 to 15 carbon atoms, a substituted or unsubstituted aromatic hydrocarbon group having 6 to 15 carbon atoms, an alkyl substituted, an aryl substituted or unsubstituted triphenylsilyl, and a diphenylphosphine oxide represented by the formula (D) or (E); m and n each independently represent 0 or 1, provided that m+n is 1 or more; and $Ar_1$ and $Ar_2$ are each independently selected from the group consisting of an alkyl substituted, aryl substituted or unsubstituted phenyl, tolyl, naphthyl, fluorenyl, anthracenyl, and phenanthryl.

9. The organic electroluminescent device of claim 8, wherein the phosphorescent dopant is an organic metal complex comprising at least one metal selected from the group consisting of ruthenium, rhodium, palladium, silver, rhenium, osmium, iridium, platinum, and gold.

10. The organic electroluminescent device of claim 8, wherein the phosphorescent dopant is one of $Ir(ppy)_3$, $Ir(bt)_2(acac)$, FIrpic, and $PtOEt_3$.

11. The organic electroluminescent device of claim 8, wherein the phosphorescent dopant is in a range from 3 wt % to 10 wt % based on the total weight of the light emitting layer.

12. An organic electroluminescent device, comprising:
an electron transport layer;
a hole block layer; and
an electron block layer,
wherein one of the electron transport layer, the hole block layer and the electron block layer comprises a compound of a formula selected from formulae (II) to (XIII)

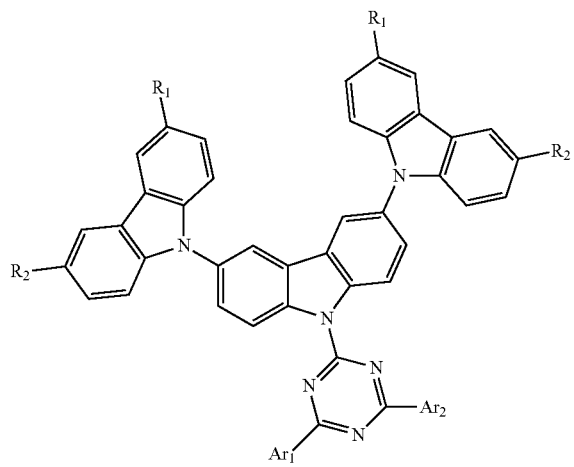

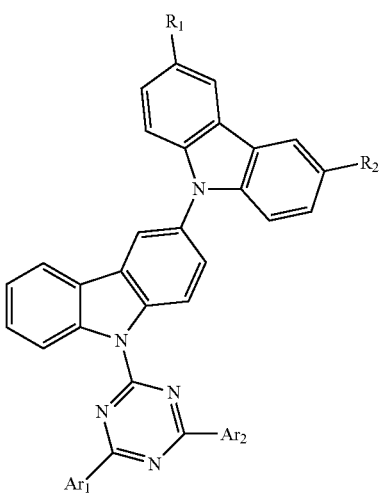

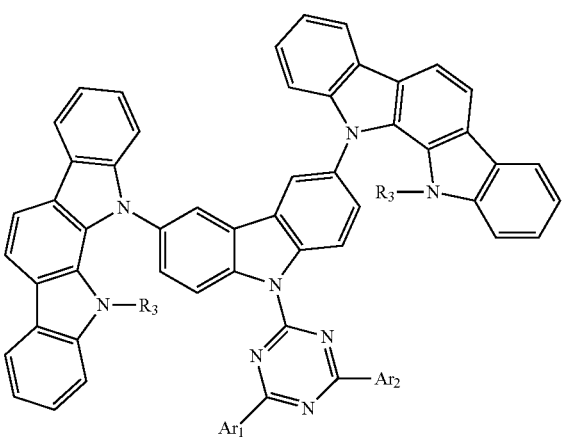

(V)
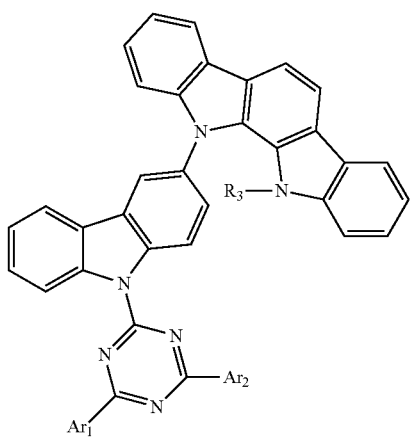
(IX)
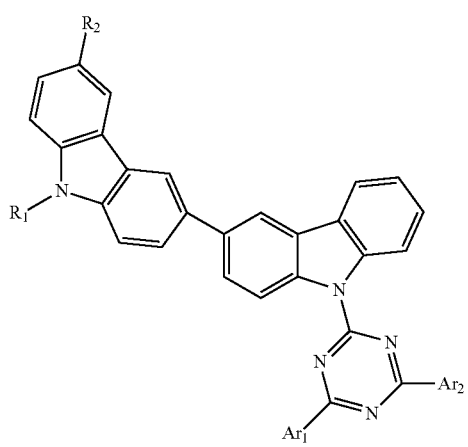
(VI)
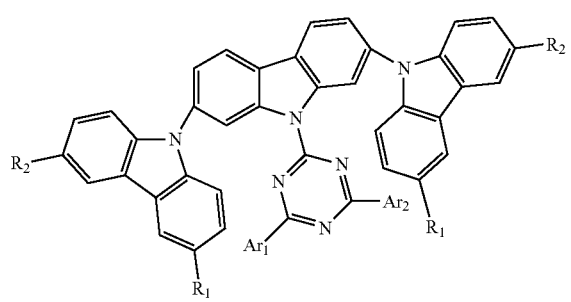
(VII)
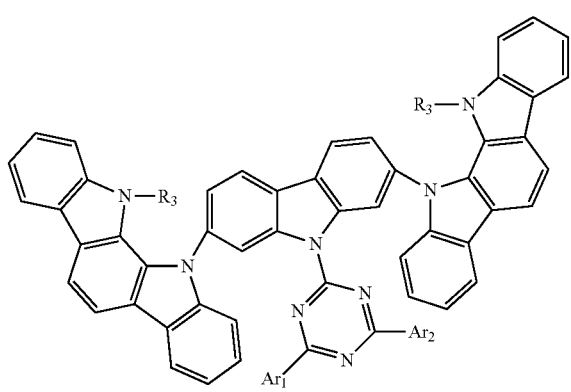
(X)
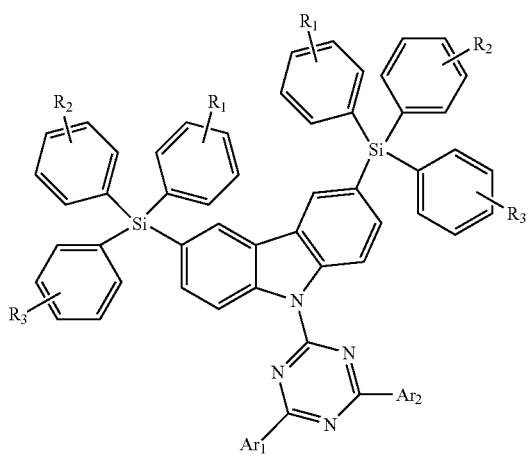
(VIII)
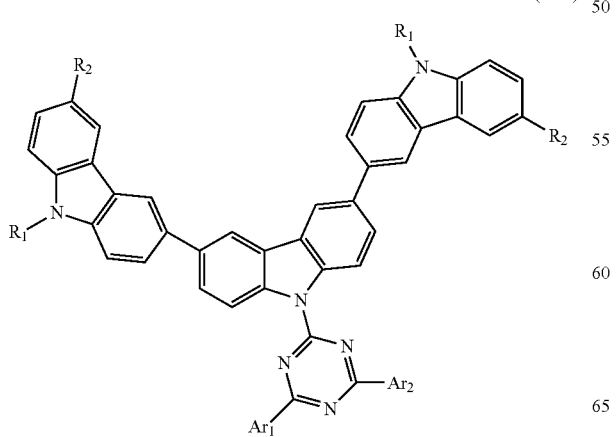
(XI)
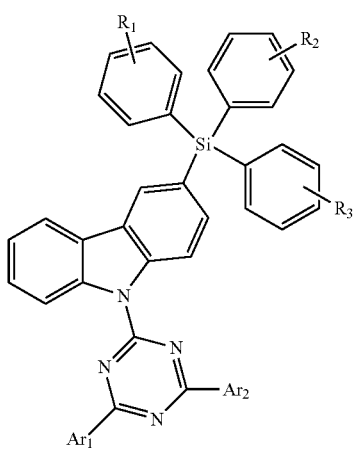

-continued (XII)
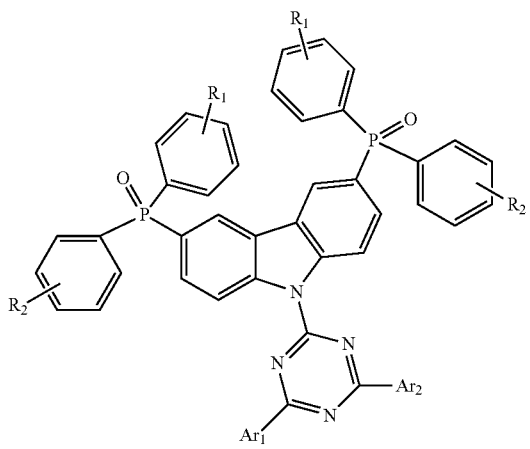

(XIII)
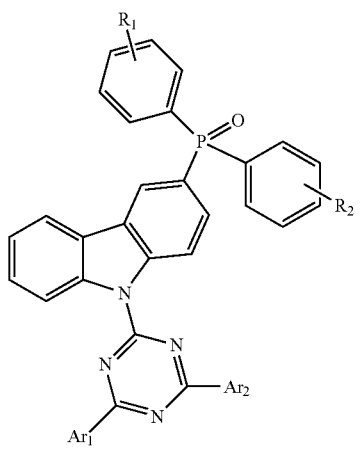

wherein R₁, R₂, and R₃ are each independently selected from the group consisting of a hydrogen, a substituted or unsubstituted alkyl group having 1 to 10 carbon atoms, a substituted or unsubstituted cycloalkyl group having 5 to 10 carbon atoms, a substituted or unsubstituted aralkyl group having 7 to 15 carbon atoms, a substituted or unsubstituted aromatic hydrocarbon group having 6 to 15 carbon atoms, an alkyl substituted, an aryl substituted or unsubstituted triphenylsilyl and a diphenylphosphine oxide represented by the formula (D) or (E); m and n each independently represent 0 or 1, provided that m+n is 1 or more; and Ar₁ and Ar₂ are each independently selected from the group consisting of an alkyl substituted, aryl substituted or unsubstituted phenyl, tolyl, naphthyl, fluorenyl, anthracenyl, and phenanthryl.

13. A method for forming an organic electroluminescent device, comprising the steps of:
providing a substrate;
forming a hole injection layer on the substrate;
forming a hole transport layer on the hole injecting layer; and
forming a light emitting layer on the hole transport layer having a phosphorescent dopant and a compound of a formula selected from formulae (II) to (XIII)

(II)
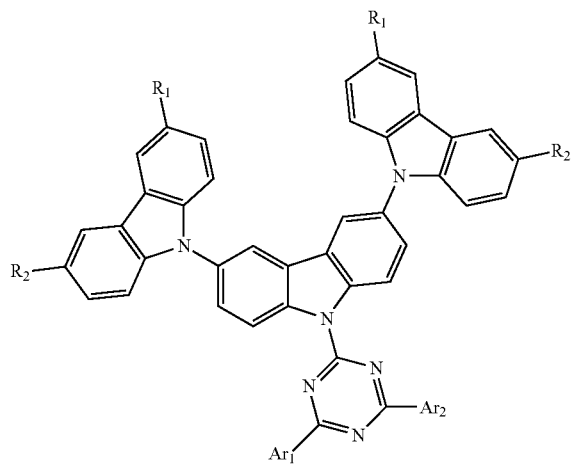

(III)
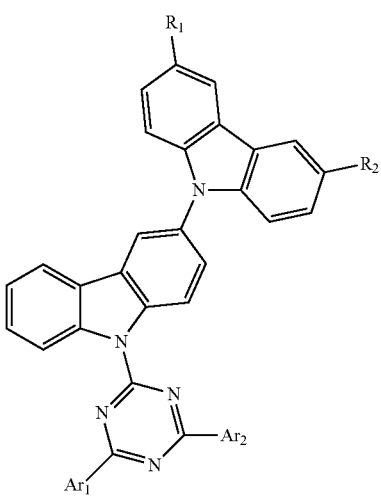

(IV)
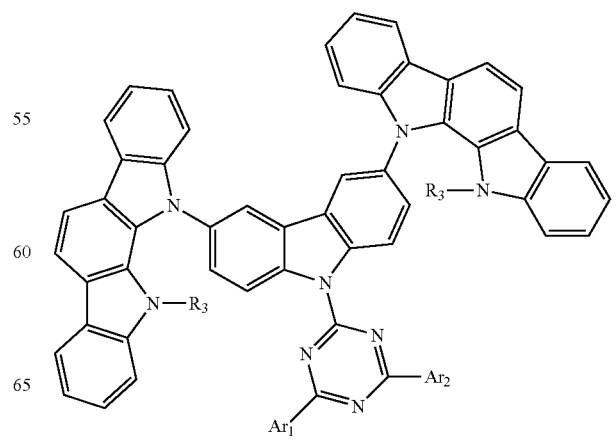

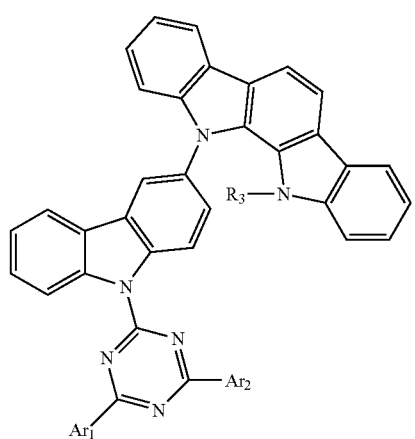
(V)
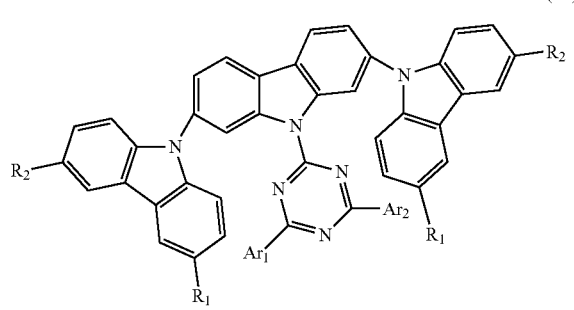
(VI)
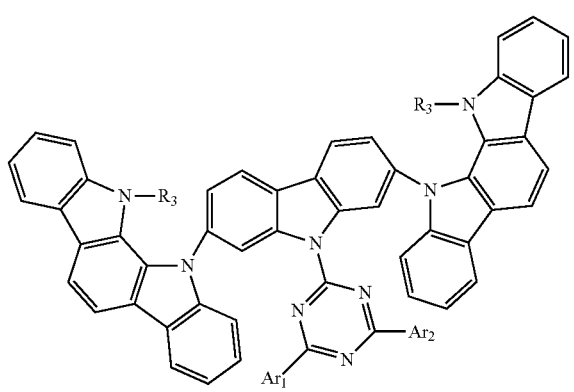
(VII)
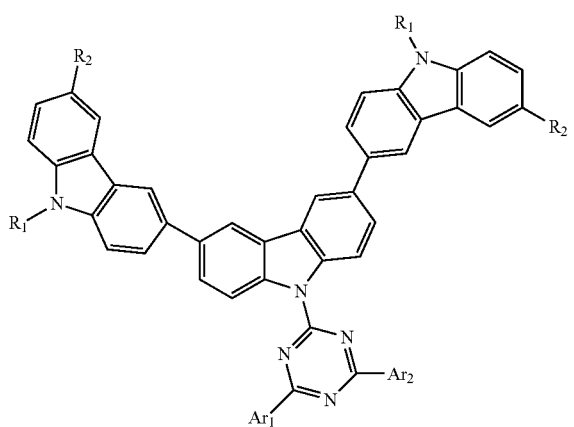
(VIII)
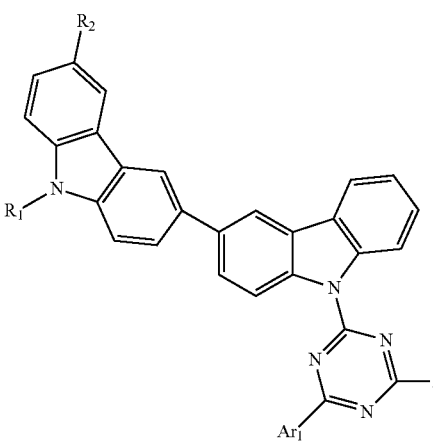
(IX)
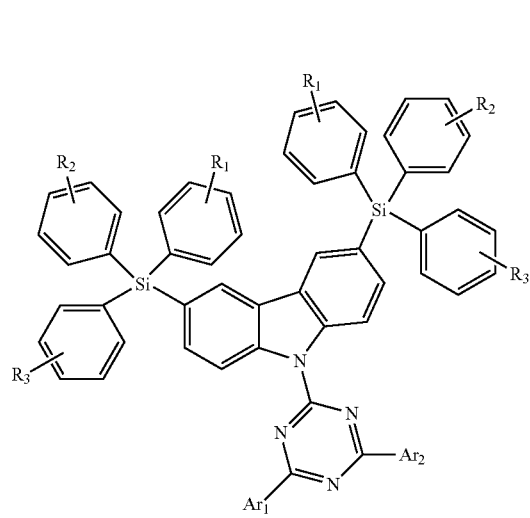
(X)
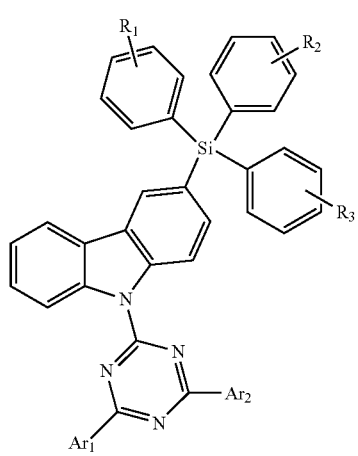
(XI)

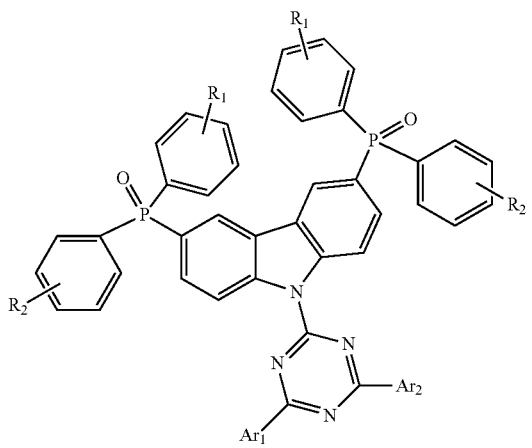

(XII)

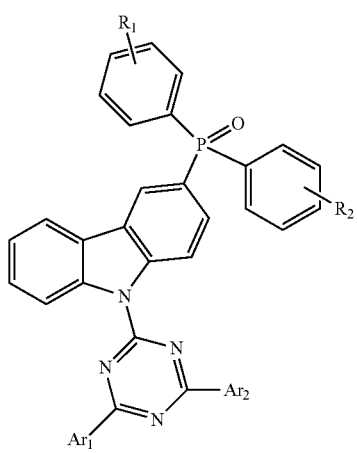

(XIII)

wherein $R_1$, $R_2$, and $R_3$ are each independently selected from the group consisting of a hydrogen, a substituted or unsubstituted alkyl group having 1 to 10 carbon atoms, a substituted or unsubstituted cycloalkyl group having 5 to 10 carbon atoms, a substituted or unsubstituted aralkyl group having 7 to 15 carbon atoms, a substituted or unsubstituted aromatic hydrocarbon group having 6 to 15 carbon atoms, an alkyl substituted, an aryl substituted or unsubstituted triphenylsilyl and a diphenylphosphine oxide represented by the formula (D) or (E); m and n each independently represent 0 or 1, provided that m+n is 1 or more; and $Ar_1$ and $Ar_2$ are each independently selected from the group consisting of an alkyl substituted, aryl substituted or unsubstituted phenyl, tolyl, naphthyl, fluorenyl, anthracenyl, and phenanthryl.

14. The method of claim 13, wherein the phosphorescent dopant is an organic metal complex comprising at least one metal selected from the group consisting of ruthenium, rhodium, palladium, silver, rhenium, osmium, iridium, platinum and gold.

15. The method of claim 14, wherein the phosphorescent dopant is one of $Ir(ppy)_3$, $Ir(bt)_2(acac)$, FIrpic, and $PtOEt_3$.

16. The method of claim 13, wherein the phosphorescent dopant is in a range from 3 wt % to 10 wt % of the light emitting layer.

* * * * *